(12) United States Patent
Arevalos et al.

(10) Patent No.: US 12,290,305 B2
(45) Date of Patent: May 6, 2025

(54) TRANSCATHETER DEVICE FOR INTERATRIAL ANASTOMOSIS

(71) Applicant: ALLEVIANT MEDICAL, INC., Austin, TX (US)

(72) Inventors: Christopher Alexander Arevalos, Austin, TX (US); Albertien Greijdanus, Austin, TX (US); Jacob Kriegel, Austin, TX (US); Avni Patel, Austin, TX (US)

(73) Assignee: Alleviant Medical, Inc., Austin, TX (US)

( * ) Notice: Subject to any disclaimer, the term of this patent is extended or adjusted under 35 U.S.C. 154(b) by 0 days.

(21) Appl. No.: 16/886,467

(22) Filed: May 28, 2020

(65) Prior Publication Data

US 2020/0289196 A1    Sep. 17, 2020

Related U.S. Application Data

(63) Continuation of application No. PCT/US2018/063439, filed on Nov. 30, 2018.
(Continued)

(51) Int. Cl.
*A61B 18/18* (2006.01)
*A61B 18/12* (2006.01)
(Continued)

(52) U.S. Cl.
CPC ...... *A61B 18/1492* (2013.01); *A61B 18/1206* (2013.01); *A61B 2017/003* (2013.01);
(Continued)

(58) Field of Classification Search
CPC ............ A61B 18/1492; A61B 18/1206; A61B 17/320725; A61B 2017/003;
(Continued)

(56) References Cited

U.S. PATENT DOCUMENTS 5,403,311 A * 4/1995 Abele ............... A61B 18/1492
606/49
5,462,545 A * 10/1995 Wang ............... A61B 18/1492
606/41
(Continued)

FOREIGN PATENT DOCUMENTS

CN    103635226 A    3/2014
EP    3 579 907 A1   12/2019
(Continued)

OTHER PUBLICATIONS

International Search Report mailed on Feb. 5, 2019, for PCT Application No. PCT/US2018/063439, filed on Nov. 30, 2018, 3 pages.
(Continued)

*Primary Examiner* — Michael F Peffley
*Assistant Examiner* — Amanda L Zink
(74) *Attorney, Agent, or Firm* — Cooley LLP

(57) ABSTRACT

The present disclosure relates to a device assembly and a method for treating heart failure by normalizing elevated blood pressure in the left atrium of a heart of a mammal Disclosed herein is a RF energy-based transcatheter interatrial septum excision device configured to create a sized interatrial aperture between the right and left atria of a heart for the relief of elevated left atrial pressure. The device assembly comprises a delivery catheter, a tissue stabilizer attached to a tissue stabilizer catheter, a tissue cutter attached to a tissue cutter catheter, a remotely located RF generator connected to an RF cathode and anode of the device assembly.

21 Claims, 22 Drawing Sheets

Related U.S. Application Data

(60) Provisional application No. 62/715,922, filed on Aug. 8, 2018, provisional application No. 62/592,630, filed on Nov. 30, 2017.

(51) Int. Cl.

| | |
|---|---|
| *A61B 18/14* | (2006.01) |
| *A61B 17/00* | (2006.01) |
| *A61B 17/11* | (2006.01) |
| *A61B 17/32* | (2006.01) |
| *A61B 17/3207* | (2006.01) |
| *A61B 18/00* | (2006.01) |
| *A61B 90/00* | (2016.01) |
| *A61M 25/09* | (2006.01) |

(52) U.S. Cl.
CPC .......... *A61B 2017/00867* (2013.01); *A61B 2017/1107* (2013.01); *A61B 2017/320069* (2017.08); *A61B 17/320725* (2013.01); *A61B 2018/00023* (2013.01); *A61B 2018/00261* (2013.01); *A61B 2018/00351* (2013.01); *A61B 2018/00601* (2013.01); *A61B 2018/00791* (2013.01); *A61B 2018/00875* (2013.01); *A61B 2018/1407* (2013.01); *A61B 2090/3966* (2016.02); *A61M 25/09* (2013.01); *A61M 2205/3331* (2013.01); *A61M 2230/205* (2013.01)

(58) Field of Classification Search
CPC .. A61B 2017/00867; A61B 2017/1107; A61B 2017/320069; A61B 2018/00023; A61B 2018/00351; A61B 2018/00601; A61B 2018/00791; A61B 2018/00875; A61B 2018/1407; A61B 17/3478; A61B 17/32002; A61B 17/32053; A61B 17/320068; A61B 2017/00247; A61B 2017/22044; A61B 2017/3488; A61B 2018/00357; A61B 2018/0212; A61B 17/11; A61B 2017/00986; A61B 2017/1139; A61B 2017/3425; A61B 17/3209; A61B 17/34; A61B 18/02; A61B 2017/320052; A61B 2017/32113; A61B 2018/00261; A61B 2090/3966; A61B 2017/22061; A61B 2017/320064; A61B 17/320016; A61B 2018/00267; A61B 2018/0038; A61B 2018/1435; A61B 2090/376; A61M 25/09; A61M 25/0108; A61M 25/06; A61M 2205/3331; A61M 2230/205
See application file for complete search history.

(56) References Cited

U.S. PATENT DOCUMENTS

| | | | | |
|---|---|---|---|---|
| 5,492,119 | A * | 2/1996 | Abrams | A61N 1/0573 600/377 |
| 5,891,138 | A * | 4/1999 | Tu | A61N 1/06 606/49 |
| 5,971,983 | A * | 10/1999 | Lesh | A61B 18/1492 606/41 |
| 6,471,709 | B1 * | 10/2002 | Fawzi | A61B 10/0266 600/562 |
| 6,689,119 | B1 | 2/2004 | Di Caprio et al. | |
| 11,992,232 | B2 * | 5/2024 | Nguyen | A61B 17/2202 |
| 2001/0001314 | A1 * | 5/2001 | Davison | A61B 18/1206 606/41 |
| 2006/0079873 | A1 * | 4/2006 | Scopton | A61B 18/1482 604/22 |
| 2006/0247617 | A1 * | 11/2006 | Danek | A61B 18/1492 606/41 |
| 2008/0125754 | A1 * | 5/2008 | Beer | A61L 29/14 427/2.24 |
| 2011/0213231 | A1 * | 9/2011 | Hall | A61B 5/0036 600/373 |
| 2012/0259263 | A1 * | 10/2012 | Celermajer | A61M 25/1002 604/509 |
| 2014/0228843 | A1 * | 8/2014 | O'Donnell | A61B 18/1492 606/48 |
| 2014/0277045 | A1 * | 9/2014 | Fazio | A61B 17/320016 606/170 |
| 2015/0094711 | A1 * | 4/2015 | Geisel | A61B 18/082 606/49 |
| 2016/0073960 | A1 * | 3/2016 | Jung | A61B 5/6858 600/374 |
| 2016/0270810 | A1 * | 9/2016 | Vardi | A61B 17/32053 |
| 2017/0354461 | A1 * | 12/2017 | Rothman | A61B 18/1492 |
| 2019/0336727 | A1 * | 11/2019 | Yang | A61B 17/221 |

FOREIGN PATENT DOCUMENTS

| | | |
|---|---|---|
| JP | 2014-512869 A | 5/2014 |
| WO | WO-2017/118920 A1 | 7/2017 |
| WO | WO-2018/148456 A1 | 8/2018 |

OTHER PUBLICATIONS

Written Opinion of the International Searching Authority mailed on Feb. 5, 2019, for PCT Application No. PCT/US2018/063439, filed on Nov. 30, 2018, 8 pages.

Extended European Search Report mailed on Nov. 5, 2021, for EP Application No. 18 884 167.0, filed on Nov. 30, 2018, 9 pages.

* cited by examiner

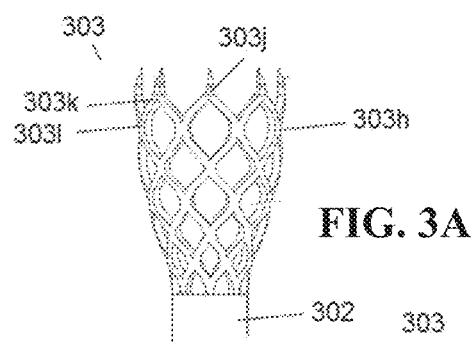
FIG. 3A
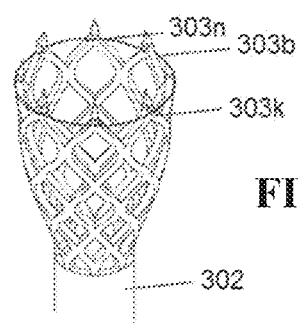
FIG. 3B
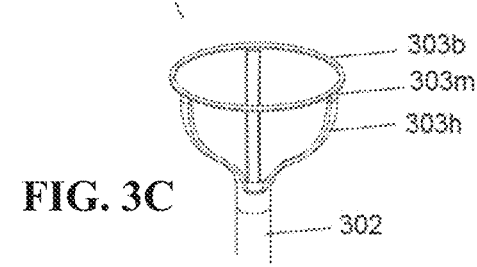
FIG. 3C
FIG. 4A
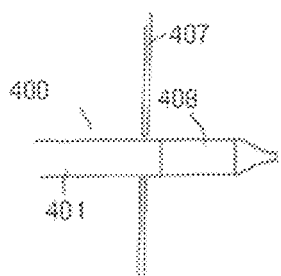
FIG. 4B
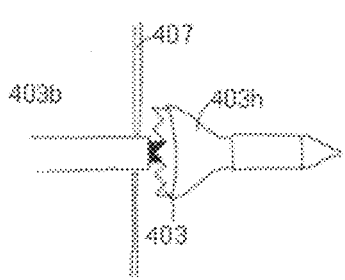
FIG. 4C
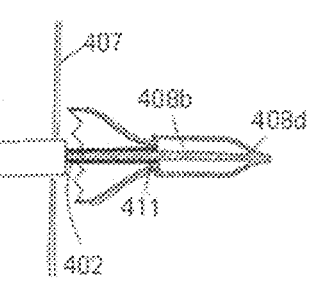
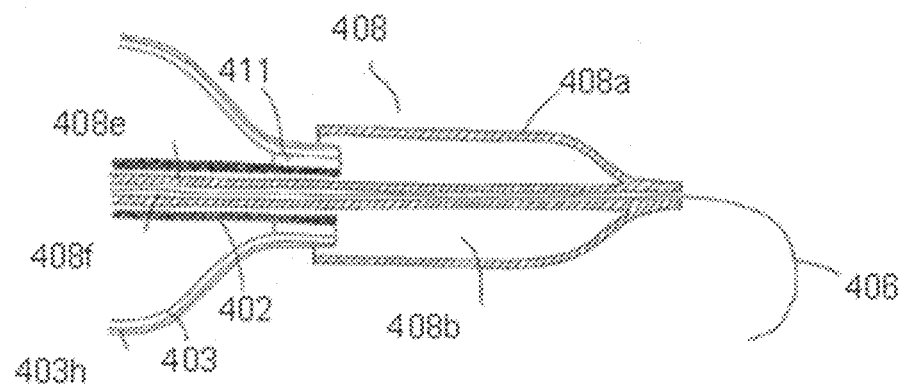
FIG. 4D

FIG. 6A
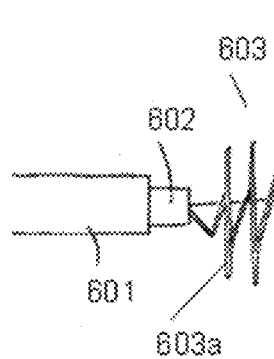
FIG. 6B
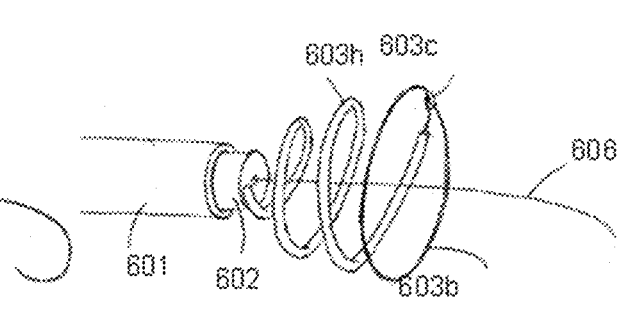
FIG. 7A
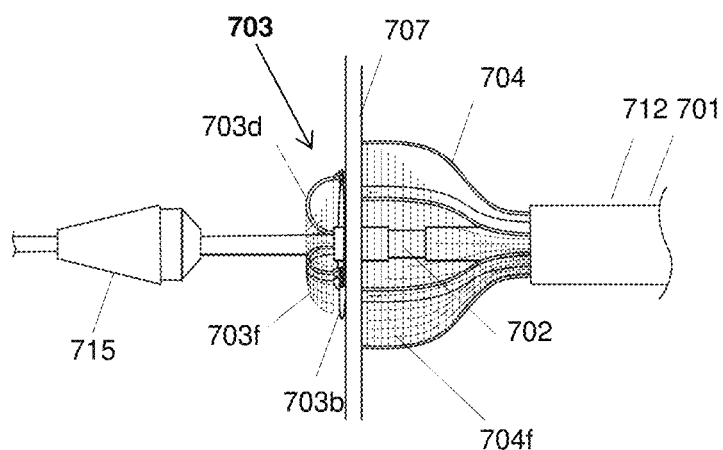
FIG. 7B
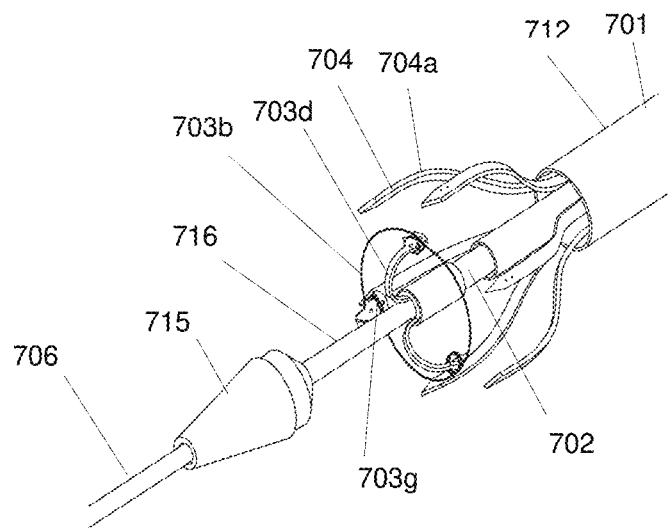
FIG. 8

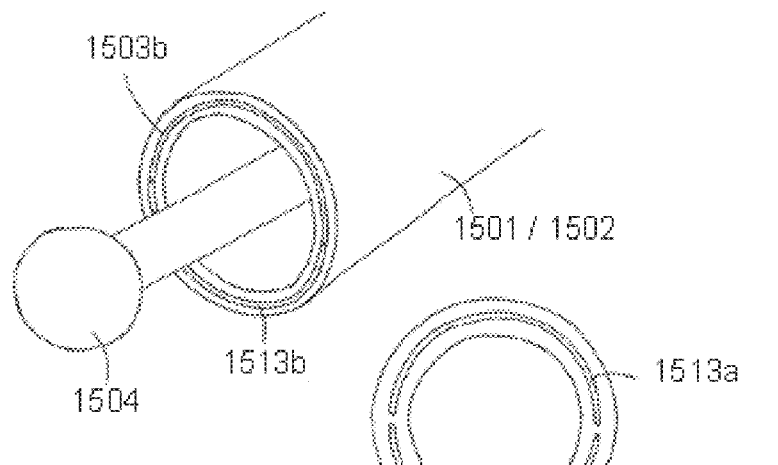
FIG. 15A
FIG. 15B
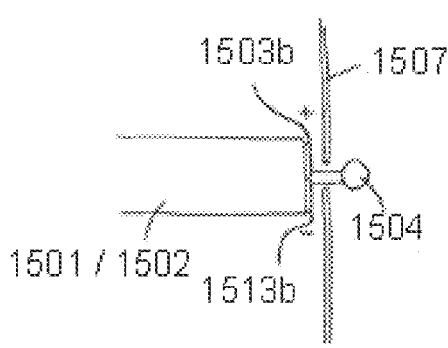
FIG. 15C
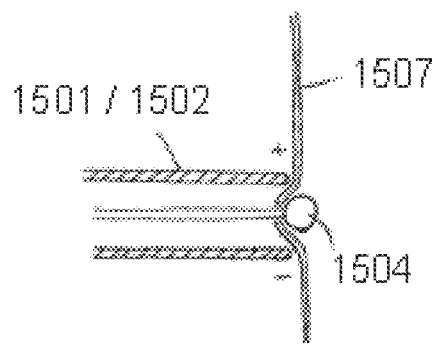
FIG. 15D
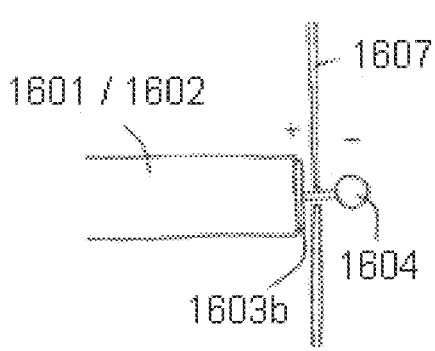
FIG. 16A
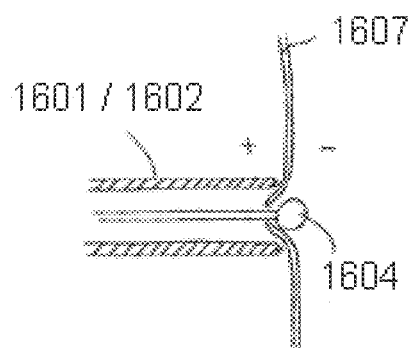
FIG. 16B

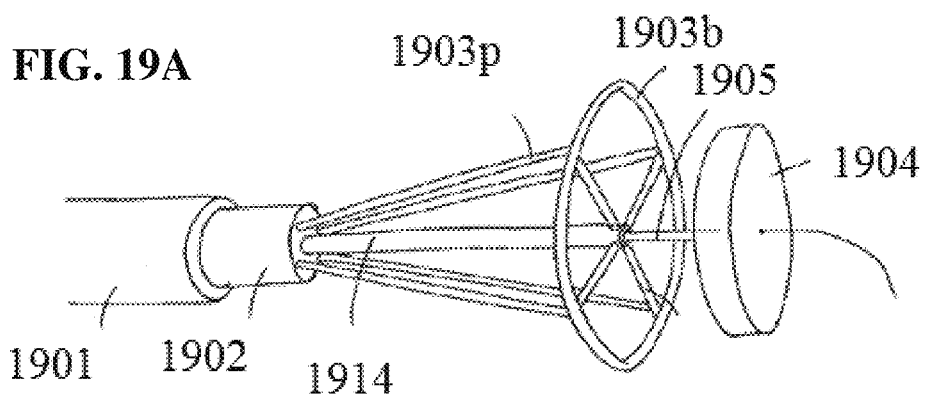
FIG. 19A
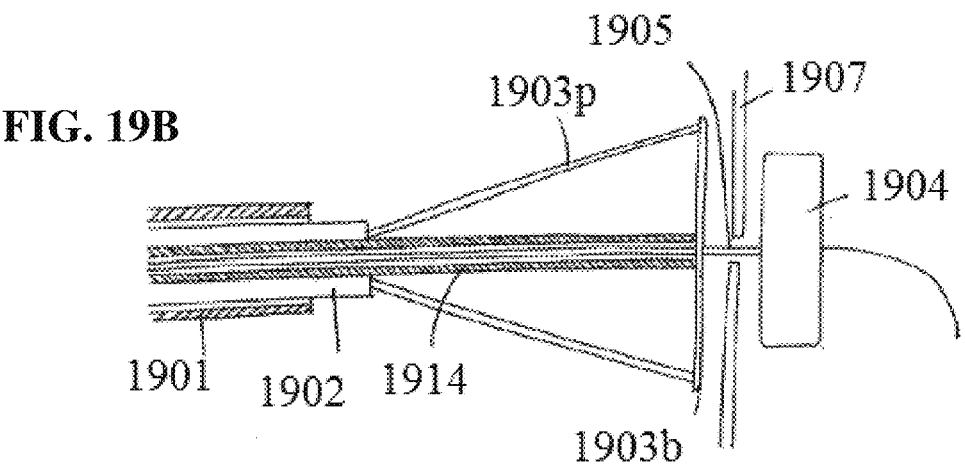
FIG. 19B
FIG. 20A
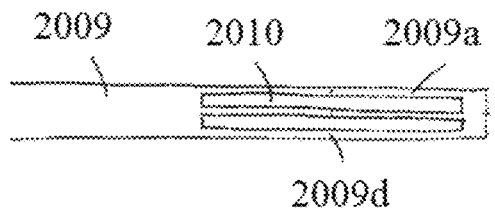
FIG. 20B
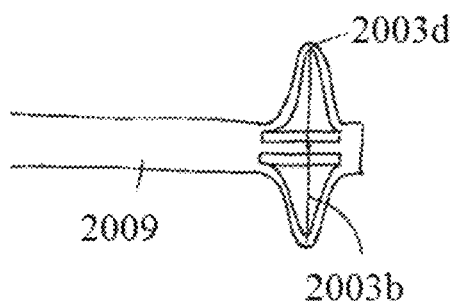

Section A-A

TRANSCATHETER DEVICE FOR INTERATRIAL ANASTOMOSIS

CROSS-REFERENCE TO RELATED APPLICATIONS

This application is a continuation filed under 35 U.S.C. § 120 of International Patent Application No. PCT/US2018/063439, filed on Nov. 30, 2018, which claims priority to U.S. Provisional Patent Application No. 62/592,630, filed Nov. 30, 2017 and to U.S. Provisional Patent Application No. 62/715,922, filed Aug. 8, 2018, the content of each of which is hereby incorporated by reference in its entirety.

BACKGROUND

Congestive heart failure (CHF) is a chronic condition affecting 6 million people in the US and 23 million people worldwide. Incidence is expected to rise in the next 10 years with 650,000 new cases diagnosed annually in the US. Heart failure is the most common cause of U.S. hospital admission in patients over 65 and accounts for almost 1 million hospitalizations annually with this number set to rise substantially. Thus, heart failure remains a major epidemic with significant associated healthcare costs.

SUMMARY

Described herein, in some embodiments, are device assemblies and methods that create a specifically-sized/prescribed aperture between the right and left atria of the heart of a mammal for the relief of elevated left atrial pressure. Disclosed herein, in some embodiments, are transcatheter interatrial septum excision device assemblies and methods configured to create a sized interatrial aperture between the right and left atria of a heart for the relief of elevated left atrial pressure. Disclosed herein, in some embodiments, are device assemblies for treating heart failure, for example, congestive heart failure. Disclosed herein, in some embodiments, are device assemblies and methods for interatrial anastomosis that achieve tissue excision using an energy-based tissue cutter. In some embodiments, the energy is in the range of radio frequency (RF) spectrum. In some embodiments, the energy is of any one or more electromagnetic wave frequencies (e.g., infrared frequencies). In some embodiments, the energy is thermal and/or laser energy. In some embodiments, such energy-based tissue cutters advantageously facilitates more efficient, accurate, controllable tissue cutting than traditional mechanical tissue cutting, thus greatly simplifies the surgical procedure and increases the success rate of interatrial anastomosis.

Overview

In some embodiments, the device assemblies disclosed herein comprise one or more of a delivery catheter, a tissue stabilizer (or equivalently herein, a tissue retention element) attached to a tissue stabilizer catheter (or equivalently herein, a tissue retention catheter) having a lumen and a penetrating tip that permits passage of a guidewire, an expandable tissue cutter (or equivalently herein, a tissue cutter) attached to a tissue cutter catheter (or equivalently herein, a tissue cutter catheter) having another lumen that permits passage of the tissue stabilizer catheter. In some embodiments, the device assemblies disclosed herein comprise one or more of a (third) catheter having a central lumen that permits passage of one or more of the components herein to and from the right atrium. In some embodiments, the tissue stabilizer catheter has a lumen that permits passage of an additional dilator catheter with a penetrating tip that has another lumen that permits passage of a guidewire. In some embodiments, the tissue stabilizer catheter has a lumen that permits passage of the tissue cutter catheter and the tissue cutter catheter has another lumen that permits passage of the dilator catheter or a guidewire. In some embodiments, the tip of the tissue stabilizing catheter penetrates the tissue so that its lumen permits passage to a guidewire.

In some embodiments, disclosed herein are device assemblies that include a guidewire, which is a part of the device assemblies or a separate 'off the shelf' component which enables use of the device assembly.

In some embodiments, the device assemblies disclosed herein include a guide catheter (catheter 1) which features a pre-bent shape, steerability, or deflectability to orient other components of the assembly at a substantially perpendicular angle with respect to the interatrial septum. In some embodiments, the guide catheter serves the role of constraining and delivering a tissue stabilizer. In some embodiments, no such guide catheter is needed.

In some embodiments, the device assembly disclosed herein includes a tissue stabilizer, which is attached to the guidewire, guide catheter (catheter 1), tissue stabilizer catheter (catheter 2), or tissue cutter catheter (catheter 3), and has a collapsed state of a first diameter and a deployed state of a second greater diameter; this component is used as a mechanism for tissue retention or stabilization to ensure the excised tissue is retained by the device. In some embodiments, the radio frequency (RF) cathode or anode is incorporated into the tissue stabilizer, while the other of the RF cathode or anode is incorporated into other element of the device assembly or external to the device assembly but in contact with the body of the mammal.

In some embodiments, the device assembly disclosed herein includes a tissue cutter, or equivalently, a tissue cutter, attached to a catheter (catheter 3, equivalent as 'tissue cutter catheter'), which is made of a conductive material and connected to an RF generator by a conductive wire.

In some embodiments, the device assembly disclosed herein includes an RF energy supply or RF cathode. In some embodiments, an RF cathode, or RF supply is incorporated in the tissue cutter.

In some embodiments, the device assembly disclosed herein includes an RF energy sink (RF anode, or RF return) to draw RF energy from the RF cathode out of the body, thus defining the field across which RF energy is transmitted. In some embodiments, the RF energy sink is placed within the body and connected to wires which leave the body and travel back to the RF generator, or a pad that is placed on the surface of the body and connected to wires that travel back to the RF generator. In some embodiments, the RF cathode or anode is incorporated into the tissue stabilizer.

In some embodiments, the device assembly disclosed herein includes a delivery catheter (catheter 4), which houses all other device components and their respective catheters prior to deployment.

In some embodiments, the device assembly disclosed herein includes an RF generator, which is stationed outside of the sterile field and connected to the RF cathode and anode through a sterile connector that crosses the sterile field and transmits RF energy to and from the RF anode and cathode, respectively.

Disclosed herein, in some embodiments, are device assemblies for interatrial anastomosis of a mammal for treating congestive heart failure, the device assemblies comprising: a delivery catheter, the delivery catheter having a delivery lumen and being steerable or bendable; a radio frequency (RF) generator, the RF generator being remotely located from the delivery catheter; and an expandable tissue cutter enclosed within the delivery lumen, the expandable tissue cutter attached to a tissue cutter catheter and configured to expand when outside the delivery lumen, wherein the expandable tissue cutter is electrically connected to the RF generator, the tissue cutter catheter coaxial to and slidable within the delivery catheter, and the tissue cutter catheter comprising a first lumen. In some embodiments, the expandable tissue cutter comprises one or more conductive materials. In some embodiments, the expandable tissue cutter is connected to the RF generator by a conductive wire.

Disclosed herein, in some embodiments, are device assemblies for interatrial anastomosis of a mammal for treating congestive heart failure, the device assembly comprising: a delivery catheter, the delivery catheter having a delivery lumen and being steerable or bendable; a radio frequency (RF) generator, the RF generator being remotely located from the delivery catheter;

Disclosed herein, in some embodiments, is an expandable tissue cutter enclosed within the delivery lumen, the expandable tissue cutter attached to a tissue cutter catheter and configured to expand when outside the delivery lumen, wherein the expandable cutter is electrically connected to the RF generator, the tissue cutter catheter coaxial to and slidable within the delivery catheter, and the tissue cutter catheter comprising a first lumen; and an expandable tissue stabilizer enclosed within the delivery lumen, the expandable tissue stabilizer attached to a tissue stabilizer catheter at or near a distal end and configured to expand when outside the delivery catheter or the tissue cutter catheter, the tissue stabilizer catheter coaxial to and slidable within the first lumen and the tissue stabilizer catheter comprising a second lumen. In some embodiments, the tissue cutter catheter is coaxial to and slidable within the second lumen of the tissue stabilizer catheter, and the expandable tissue cutter is configured to expand when outside the delivery catheter of the tissue stabilizing catheter.

Disclosed herein, in some embodiments, is a device assembly to create a sized aperture in the septum between the right and left atria of the heart of a mammal for treating congestive heart failure, the device assembly comprising: a) a delivery catheter, the delivery catheter having a delivery lumen; b) a first connector and a second connector to a radio frequency (RF) generator; the RF generator being remotely located from the delivery catheter; c) an expandable tissue cutter enclosed within the delivery lumen, the expandable tissue cutter attached to a tissue cutter catheter comprising an expanded configuration outside of the delivery lumen, wherein the expandable tissue cutter comprises a cathode electrically coupled to the first connector for the RF generator, the tissue cutter catheter coaxial to and slidable within the delivery catheter; and d) an expandable tissue stabilizer enclosed within the delivery lumen, the expandable tissue stabilizer attached to a tissue stabilizer catheter and adjacent to the tissue cutter catheter, wherein the expandable tissue stabilizer comprises an expanded configuration outside of the delivery lumen, the tissue stabilizer catheter coaxial to and slidable within the delivery catheter; wherein the tissue cutter catheter is distal to the tissue stabilizer catheter in the delivery catheter. In some embodiments, the expandable tissue cutter comprises one or more conductive materials. In some embodiments, the expandable tissue cutter is connectable to the first connector for the RF generator by a conductive wire. In some embodiments, the conductive wire is at least partly within a wall of the tissue cutter catheter or at least partly along the tissue cutter catheter. In some embodiments, the expandable tissue cutter comprises an RF cathode. In some embodiments, the device assembly further comprises an RF skin patch anode connectable to the second connector of the RF generator. In some embodiments, the expandable tissue stabilizer comprises an RF anode. In some embodiments, the RF generator generates RF energy from the RF cathode through tissue of the mammal to the RF anode. In some embodiments, the RF cathode is in contact with a body of the mammal. In some embodiments, a distance between the RF anode and the RF cathode is within a range of about 1 mm to about 2 meters. In some embodiments, the expandable tissue cutter comprises an RF anode. In some embodiments, the RF generator generates RF energy from an RF cathode through tissue of the mammal to the RF anode. In some embodiments, the distance between the RF anode and the RF cathode is within a range of about 1 mm to about 2 meters. In some embodiments, the RF cathode is a ring-shaped electrode. In some embodiments, the RF anode is ring-shape. In some embodiments, the device assembly further comprising a guide catheter, a dilator catheter, a dilator lumen to permit translation over the guidewire, a distal dilator shaft comprising a lumen, a dilator tip coaxial to the guide catheter, a tissue stabilizer strut, and a tissue cutter strut. In some embodiments, the RF generator generates alternating current with an alternating frequency within a range of about 300 kHz to about 3 MHz or a power within a second range of about 1 Watt to about 500 Watts. In some embodiments, the expandable tissue cutter and the expandable tissue stabilizer comprise superelastic shape memory alloy. In some embodiments, the expandable tissue cutter assumes a generally planer ring-like configuration when deployed and unconstrained outside of the tissue cutter catheter. In some embodiments, the expandable tissue stabilizer assumes a generally planar ring-like configuration when deployed and unconstrained outside of the tissue stabilizer catheter. In some embodiments, an expanded cross-sectional profile of the cutting portion of the expandable tissue cutter comprises a non-circular cross-sectional profile, such as an oval, triangle, square, hexagon, octagon, or other polygon. In some embodiments, an expanded cross-sectional profile of the stabilizing portion of the expandable tissue stabilizer comprises a non-circular cross-sectional profile, such as an oval, triangle, square, hexagon, octagon, or other polygon. In some embodiments, the generally planer cutting portion of the expandable tissue cutter comprises an expanded dimension between 4.0 mm and 12.0 mm at the widest dimension. In some embodiments, the generally planer contacting portion of the expandable tissue stabilizer comprises an expanded dimension between 5.0 mm and 18.0 mm at the widest dimension. In some embodiments, a cutting dimension of the expandable tissue cutter is adjustable. In some embodiments, a dimension of the contacting portion of the expandable tissue stabilizer is adjustable. In some embodiments, the expandable tissue cutter and the expandable tissue stabilizer comprise one or more conductive materials.

Disclosed herein, in some embodiments, are methods of operating a device assembly to create a sized aperture in the septum between the right and left atria of the heart of a mammal for treating congestive heart failure, the method comprising: a) delivering the device assembly to the right atria of the heart in proximity to a center of an interatrial septum, the device assembly comprising: a delivery catheter, the delivery catheter having a delivery lumen; a distal dilator catheter with a distal dilator tip; a first connector and a second connector to a radio frequency (RF) generator; the RF generator being remotely located from the delivery catheter; an expandable tissue cutter enclosed within the delivery lumen, the expandable tissue cutter attached to a tissue cutter catheter, wherein the expandable tissue cutter comprises a cathode electrically coupled to the first connector for the RF generator, the tissue cutter catheter coaxial to and slidable within the delivery catheter; and an expandable tissue stabilizer enclosed within the delivery lumen, the expandable tissue stabilizer attached to a tissue stabilizer catheter and adjacent to the tissue cutter catheter, the tissue stabilizer catheter coaxial to and slidable within the delivery catheter, wherein the tissue cutter catheter is distal to the tissue stabilizer catheter in the delivery catheter; b) advancing the distal dilator tip of the assembly across the interatrial septum such that the distal dilator catheter is positioned within the left atrium with the remaining half of the delivery catheter residing within the right atrium; c) advancing the distal dilator catheter with respect to all other components to unsheath and deploy, fully expand and lock in place the expandable tissue cutter, support struts, and tissue cutter cathode; d) withdrawing the tissue cutter catheter proximally such that tissue cutter cathode of the expandable tissue cutter is brought into contact with the left atrial face of the septum; e) retracting the tissue stabilizer catheter with respect to all other device components to unsheath, deploy, fully expand and lock in place the tissue stabilizer, support struts, and stabilizing portion of the tissue stabilizer within the right atrium; f) advancing the deployed tissue stabilizer proximally such that the stabilizing portion of the tissue stabilizer is brought into contact with the right atrial face of the septum opposing the tissue cutter cathode of the expandable tissue cutter; g) providing an anode to a surface of the mammal comprising a connector to electrically coupled to the second connector for the RF generator; h) coupling the cathode to the first connector for the RF generator; i) coupling the anode to the second connector for the RF generator; j) energizing the cathode using the RF generator causing the tissue cutter to cut a coin of tissue forming an anastomosis in the atrial septum; k) retracting the excised tissue coin, the tissue cutter, the tissue stabilizer and a portion of the distal dilator catheter proximally into the right atrium; l) advancing the tissue cutter catheter and distal dilator catheter distally such that the excised tissue coin is collapsed within the struts of the tissue cutter; m) capturing the excised tissue coin and end of the tissue cutter within a cage formed by the tissue stabilizer struts and the stabilizing portion of the tissue stabilizer and withdrawing proximally, first, into the tissue stabilizer catheter, then into the delivery catheter; and n) completely withdrawing the device from the septum and atrium.

Disclosed herein, in some embodiments, are methods for excision of an interatrial septum of a mammal for treating congestive heart failure using a transcatheter device assembly, the methods comprising: advancing an expandable tissue cutter over a guidewire and across the interatrial septum to a left atrium, the expandable tissue cutter in a compressed state; expanding and moving the tissue cutter to provide tensioning to the interatrial septum in the left atrium; translating the tissue cutter to be in contact with the interatrial septum; transmitting RF power between an RF cathode and an RF anode across the interatrial septum thereby creating an aperture, wherein the RF cathode or the RF anode is located on the expandable tissue cutter and the other of the RF cathode or the RF anode is located on a delivery catheter or in contact with tissue of the mammal; and resheathing the expandable tissue cutter into the delivery catheter with the cut interatrial septum. In some embodiments, an expandable tissue stabilizer is deployed on the opposite side of the interatrial septum to provide tissue stabilization prior to transmitting RF power across the interatrial septum, thereby creating an aperture.

Disclosed herein, in some embodiments, are methods for excision of an interatrial septum for treating congestive heart failure using a transcatheter device assembly, the methods comprising: puncturing through a fossa ovalis of an interatrial septum and advancing a guidewire to a left atrium; advancing an expandable tissue stabilizer over the guidewire and across the interatrial septum, the expandable tissue stabilizer in a compressed state; deploying and moving the tissue stabilizer to provide tensioning to the interatrial septum in the left atrium; delivering an expandable tissue cutter to a right atrium, the expandable tissue cutter in a second compressed state housed in a delivery catheter of the device assembly; expanding the expandable tissue cutter in the right atrium; translating the cutter forward to be in contact with the interatrial septum thereby sandwiching the interatrial septum between the expandable tissue cutter and the expandable tissue stabilizer; transmitting RF power between an RF cathode and an RF anode across the interatrial septum thereby creating an aperture, wherein the RF cathode or the RF anode is located on the expandable tissue stabilizer; and resheathing the expandable tissue cutter and the expandable tissue stabilizer into the delivery catheter with the cut interatrial septum.

BRIEF DESCRIPTION OF THE DRAWINGS

The novel features of the device assemblies herein are set forth with particularity in the appended claims. A better understanding of the features and advantages of the present disclosure will be obtained by reference to the following detailed description that sets forth illustrative embodiments, in which the principles of the device assemblies herein are utilized, and the accompanying drawings of which:

FIGS. 3A-3C show an exemplary embodiment of the RF energy-based device assemblies for interatrial anastomosis; in this case, a tissue cutter of the device assemblies;

FIGS. 4A-4D show an exemplary embodiment of the RF energy-based device assemblies for interatrial anastomosis;

FIGS. 6A-6B show an exemplary embodiment of the RF energy-based device assemblies for interatrial anastomosis; in this case, a tissue cutter of the device assemblies;

FIGS. 7A-7B show an exemplary embodiment of the RF energy-based device assemblies for interatrial anastomosis; in this case, a tissue cutter of the device assemblies; a tissue stabilizer of the device assemblies; a fine mesh of the tissue cutter to facilitate retention of excised tissue within the device assemblies post-cutting; a fine mesh of the tissue stabilizer to facilitate retention of excised tissue within the device assemblies post-cutting; a dilator tip to facilitate passage of the device assemblies across the interatrial septum;

FIGS. 15A-15D show an exemplary embodiment of the RF energy-based device assemblies for interatrial anastomosis; in this case, the RF cathode and anode of the device assemblies;

FIGS. 16A-16B show an exemplary embodiment of the RF energy-based device assemblies for interatrial anastomosis;

FIGS. 19A-19B show an exemplary embodiment of the RF energy-based device assemblies for interatrial anastomosis; in this case; a tissue cutter of the device assemblies;

FIGS. 20A-20D show an exemplary embodiment of the RF energy-based device assemblies for interatrial anastomosis; in this case; a tissue cutter of the device assemblies;

DETAILED DESCRIPTION

Figure 1:
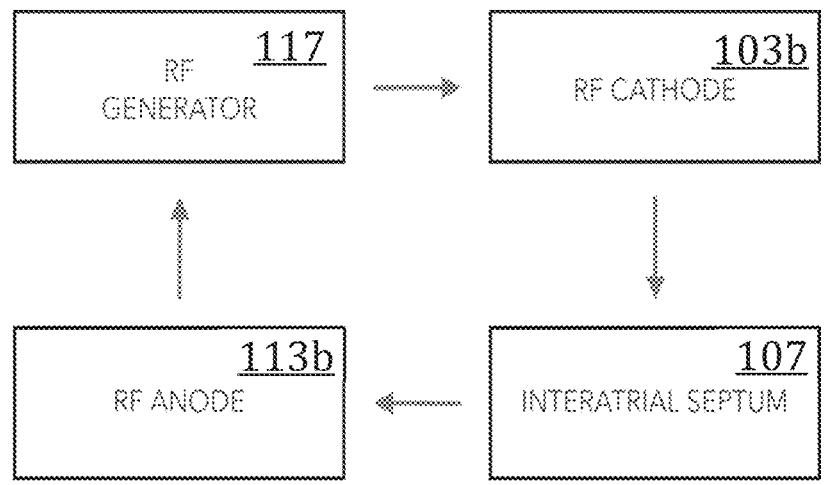
FIG. 1 is a schematic diagram of an exemplary embodiment of the RF energy-based device assemblies for interatrial anastomosis; in this case, the RF generator, cathode, and anode of the device assemblies.

CHF is marked by declining function of the heart muscle, either due to a weakening of its pumping ability, known as heart failure with reduced ejection fraction (HFrEF), or a stiffening of the muscle with decreased ability to fill with blood prior to ejection, known as heart failure with preserved ejection fraction (HFpEF). Inability of the heart to eject or fill with blood leads to symptoms of shortness of breath, fatigue, and significant functional limitation. Prevalence of HFrEF and HFpEF are roughly equal though rates of HFpEF are rising faster than HFrEF. With poor flow of blood from the heart to vital organs, the renin-angiotensin-aldosterone system (RAAS) is activated which signals the body to retain fluid, thereby increasing pressure in the heart chambers. In particular, as the left atrial pressure (LAP) rises, fluid backs up into the pulmonary circulation leading to pulmonary edema and severe shortness of breath. While LAP in normal adults ranges from 10-15 mmHg, patients with heart failure frequently have LAP in the 30-40 mmHg range, which, in some embodiments, spikes during periods of increased heart demand.

Existing pharmacologic treatments for heart failure attempt to remove excess fluid in the body through renal excretion (diuretics), neurohormonal blockade, or dilation of peripheral blood vessels in order to reduce the stress-load on a failing heart. These pharmacologic therapies offer some symptomatic relief and have shown slight mortality benefit in treating HFrEF, but importantly have not been shown to improve survival for those with HFpEF.

There are limited device-based therapies for heart failure. Mechanical circulatory support, in which a motorized pump is surgically implanted and takes over the function for the failing heart, is highly invasive and is reserved for end-stage progression of disease. Percutaneous mechanical pumps are used in an acute setting but are only approved for short-term use. Similarly, intra-aortic balloon pumps, which decrease cardiac afterload and improve coronary perfusion, are used only in the acute inpatient settings. Finally, cardiac resynchronization therapies, in which an implantable pacemaker improves coordinated contraction of failing ventricles, has shown good results for improving mortality for patients with heart failure and concomitant electrical conduction abnormalities.

Experimental therapies have sought to reduce elevated left atrial pressure by implanting a metal stent within the interatrial septum which creates a shunt between the high-pressure left atrium towards the low-pressure right atrium. Since the right atrium and the venous reservoir are highly compliant, left-to-right blood shunting, in some embodiments, effectively lower left atrial pressure without a significant elevation of right atrial pressure, thereby relieving symptoms and improving cardiac mechanics. Early human data from these interatrial shunts are showing promise with improved functional status and hemodynamic parameters.

The optimal size for these interatrial shunts is unknown, though it has been approximated using simulation data and early animal studies. Importantly, the size of the interatrial aperture must be large enough to allow effective left atrial offloading, without allowing too much blood to flow to the right side such that undue stress is placed on the right atrium and ventricle. It is widely accepted among clinicians that individuals presenting with congenital atrial septal defects warrant closure if the defect size results in a shunt fraction greater than 50%. Accordingly, sizing an interatrial shunt such that no more than 50% of left atrial blood is shunted is important to reduce long-term adverse effects.

Implantable interatrial shunts have a number of disadvantages. Since a foreign body is left within the heart chambers and makes contact with blood, clotting and thrombosis is a risk that will likely require pharmacologic anticoagulation, either long-term or until endothelialization of the device's surface occurs. The implant also carries the risk of device-fracture, dislodgement, or embolization. The implanted stent in some embodiments also makes it difficult for subsequent transseptal procedures as it could limit the degree of freedom for a catheter to move within the left atrium. Finally, should closure ever become desirable, a bulky stent, in some embodiments, adds to the difficulty of sealing off the interatrial shunt.

Balloon atrial septostomy is a procedure with an associated medical device which attempts to create an interatrial aperture to allow mixing of blood between the left and right sides of the heart. This device is used in the pediatric population to treat congenital heart lesions prior to definitive surgical correction. A deflated balloon, with or without blades attached, is introduced via the venous system across the interatrial septum and into the left atrium. The balloon is subsequently inflated and pulled proximally thereby tearing the septum and opening an interatrial aperture. This device generates an interatrial aperture that is not reproducible from patient to patient. Since the septum is torn, the resultant tissue flaps remain in place and eventually fuse back together. The aperture created by these device assemblies uniformly close over a period of months. The temporary nature of these interatrial apertures makes them suitable for the short-term treatment of congenital birth defects but they are not useful in the adult heart failure population where a more durable therapy is desired.

Thus, a device that is capable of creating a sized atrial aperture for the relief of atrial pressure, without requiring an implant and in a manner which ensures "long-term" patency, is advantageous. Using such a device would achieve the equivalent physiology to an implantable stent without the negative sequelae of a leave-behind device. It is desirable to create a precisely-sized aperture that could remain patent for the duration of a desired therapeutic benefit. Since this therapy would most likely be beneficial for a patient population with high burden of comorbidities, creating such an aperture through a minimally invasive procedure is also advantageous. It is therefore the goal of this device to enable the creation of a precisely-sized aperture through a small (<18 Fr, <6.0 mm, <0.236 in.) percutaneous puncture.

In some embodiments, "distal" herein refers to a location, a part, or an element, e.g. of the device assembly herein, that is situated further away from the operator of the device assembly, and "proximal" herein refers to a location, a part, or an element that is situated nearer to the operator of the device assembly. For example, the tip of the guidewire in FIG. 4D is distal to the delivery catheter or the distal tip of the delivery catheter.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

As used in this specification and the appended claims, unless otherwise stated, the term "coapt" refers to the action of mating or bringing two things together.

The present disclosure relates to RF energy-based device assemblies and methods for treating heart failure by reducing elevated blood pressure in the left atrium of a heart of a mammal. Disclosed herein, in some embodiments, are transcatheter interatrial septum excision device assemblies configured to create a sized atrial aperture between the right and left atria of a heart for the relief of left elevated atrial pressure to allow shunting of no more than 50% of the left atrium blood to the right atrium of the heart. Instead of using mechanical tissue cutters, disclosed herein, in some embodiments, are transcatheter interatrial septum excision device assemblies that utilize RF energy-based tissue cutters. In some embodiments, such RF energy-based tissue cutters advantageously facilitate more efficient, accurate, controllable tissue cutting than traditional mechanical tissue Disclosed herein, in some embodiments, are device assemblies for interatrial anastomosis of a mammal for treating congestive heart failure, the device assemblies comprising: a delivery catheter, the delivery catheter having a delivery lumen and being steerable or bendable; a radio frequency (RF) generator, the RF generator being remotely located from the delivery catheter; and an expandable tissue cutter enclosed within the delivery lumen, the expandable tissue cutter attached to a tissue cutter catheter and configured to expand when outside the delivery lumen, wherein the expandable tissue cutter is electrically connected to the RF generator, the tissue cutter catheter coaxial to and slidable within the delivery catheter, and the tissue cutter catheter comprising a first lumen. In some embodiments, the expandable tissue cutter comprises one or more conductive materials. In some embodiments, the expandable tissue cutter is connected to the RF generator by a conductive wire. In some embodiments, the conductive wire is at least partly within a wall of the tissue cutter catheter or at least partly along the tissue cutter catheter.

In some embodiments, the expandable tissue cutter comprises an RF anode, and the RF generator is configured to generate RF energy from an RF cathode through tissue of the mammal to the RF anode. In some embodiments, the RF cathode is in contact with a body of the mammal. In some embodiments, a distance between the RF anode and the RF cathode is within a range of about 1 mm to about 2 meters. In some embodiments, the expandable tissue cutter comprises an RF cathode, and the RF generator is configured to generate RF energy from the RF cathode through tissue of the mammal to an RF anode. In some embodiments, the distance between the RF anode and the RF cathode is within a range of about 1 mm to about 2 meters. In some embodiments, the RF anode is in contact with a body of the mammal. In some embodiments, the RF cathode is a single-point electrode, a patch electrode, or a ring electrode. In some embodiments, the device assemblies comprise an RF anode, wherein the RF anode is located on a guidewire, a guide catheter, or the delivery catheter. In some embodiments, the RF anode is a single-point electrode, a patch electrode, or a ring electrode. In some embodiments, the RF generator is configured to generate alternating current with an alternating frequency within a range of about 300 kHz to about 3 MHz or a power within a second range of about 1 Watt to about 500 Watts. In some embodiments, the RF generator is configured to output a constant voltage, power, or current during at least part of operation of the device assembly. In some embodiments, the RF generator is configured to output a current, voltage, or power having at least a part of a sine wave. In some embodiments, the RF generator comprises a monitor that is configured to monitor a parameter at the tissue cutter. In some embodiments, the RF generator comprises an adjuster configured to adjust an output of the RF generator based on the monitored parameter. In some embodiments, the RF generator comprises a pump configured to circulate a cooling agent to the tissue cutter thereby regulate a temperature of the tissue cutter. In some embodiments, the expandable tissue cutter is at least partly insulated or at least partly non-conductive. In some embodiments, at least a part of a distal cutting edge of the tissue cutter is not insulated or non-conductive. In some embodiments, the device assemblies comprise a centralizer mounted outside of the tissue cutter catheter and slidably engaged with the delivery catheter. In some embodiments, said centralizer is configured to provide centralization between the tissue cutter and the delivery catheter. In some embodiments, the tissue cutter is configured to be deployed within a left atrium of the mammal and pulled toward a right atrium of the mammal, thereby provides tissue stabilization and retention during operation of the device assembly. In some embodiments, the device assemblies comprise a guidewire. In some embodiments, the guidewire is configured to extend from a distal end of the delivery lumen and pass through an initial puncture site in an interatrial septum between a right atrium and a left atrium of the mammal at approximately a fossa ovalis to provide a working track for the device assembly into the left atrium. In some embodiments, the guidewire is coaxially located and slidably engaged with the first lumen. In some embodiments, the device assemblies comprise a guide catheter, wherein the guide catheter is coaxially located within the first lumen, and wherein the guide catheter comprises a second lumen within which the guidewire is configured to slide. In some embodiments, excised tissue by the tissue cutter from an interatrial septum is captured and maintained at least by the tissue cutter. In some embodiments, the tissue cutter is configured to be withdrawn into the delivery lumen collapsed, wherein the tissue stabilizer is simultaneously fully collapsed inside the tissue cutter, capturing an excised tissue therein. In some embodiments, a cutting dimension of the expandable tissue cutter is adjustable. Disclosed herein, in some embodiments, are device assemblies for interatrial anastomosis of a mammal for treating congestive heart failure, the device assembly comprising: a delivery catheter, the delivery catheter having a delivery lumen and being steerable or bendable; a radio frequency (RF) generator, the RF generator being remotely located from the delivery catheter; an expandable tissue cutter enclosed within the delivery lumen, the expandable tissue cutter attached to a tissue cutter catheter and configured to expand when outside the delivery lumen, wherein the expandable cutter is electrically connected to the RF generator, the tissue cutter catheter coaxial to and slidable within the delivery catheter, and the tissue cutter catheter comprising a first lumen; and an expandable tissue stabilizer enclosed within the delivery lumen, the expandable tissue stabilizer attached to a tissue stabilizer catheter at or near a distal end and configured to expand when outside the delivery catheter or the tissue cutter catheter, the tissue stabilizer catheter coaxial to and slidable within the delivery lumen or first lumen; the tissue stabilizer catheter comprising a second lumen that is slidably engaged and coaxial to the tissue cutter catheter or the dilator tip catheter. In some embodiments, the expandable tissue cutter comprises one or more conductive materials. In some embodiments, the expandable tissue cutter is connected to the RF generator by a conductive wire. In some embodiments, the conductive wire is at least partly within a wall of the tissue cutter catheter or at least partly along the tissue cutter catheter.

In some embodiments, the expandable tissue cutter comprises an RF anode, and the RF generator is configured to generate RF energy from an RF cathode through tissue of the mammal to the RF anode. In some embodiments, the RF cathode is in contact with a body of the mammal. In some embodiments, the distance between the RF anode and the RF cathode is within a range of about 1 mm to about 2 meters. In some embodiments, the expandable tissue cutter comprises an RF cathode, and the RF generator is configured to generate RF energy from the RF cathode through tissue of the mammal to an RF anode. In some embodiments, a distance between the RF anode and the RF cathode is within a range of about 1 mm to about 2 meters. In some embodiments, the RF anode is in contact with a body of the mammal. In some embodiments, the device assemblies comprise an RF anode, wherein the RF anode is located on a guidewire, a guide catheter, the tissue stabilizer catheter, the tissue stabilizer, or the delivery catheter. In some embodiments, the RF generator is configured to generate alternating current with an alternating frequency within a range of about 300 kHz to about 3 MHz or a power within a second range of about 1 Watt to about 500 Watts. In some embodiments, the RF generator is configured to output a constant voltage, power, or current for at least part of operation of the device assembly. In some embodiments, the RF generator is configured to output a current, voltage, or power having at least a portion of a sine wave. In some embodiments, the RF generator comprises a monitor that is configured to monitor a parameter at the tissue cutter. In some embodiments, the RF generator comprises an adjuster configured to adjust an output of the RF generator based on the monitored parameter. In some embodiments, the RF generator comprises a pump configured to circulate a cooling agent to the tissue cutter thereby regulate a temperature of the tissue cutter. In some embodiments, the tissue cutter is at least partly insulated or at least partly non-conductive. In some embodiments, at least a part of a distal cutting edge of the tissue cutter is not insulated or non-conductive. In some embodiments, the device assemblies comprise a centralizer mounted outside of the tissue cutter catheter and slidably engaged with the delivery catheter. In some embodiments, said centralizer is configured to provide centralization between the tissue cutter and the delivery catheter. In some embodiments, the tissue cutter is configured to be deployed within a left atrium of the mammal and pulled toward a right atrium of the mammal, thereby providing tissue stabilization and retention during operation of the device assembly. In some embodiments, the device assemblies comprise a guidewire. In some embodiments, the guidewire is configured to extend from a distal end of the delivery lumen and pass through an initial puncture site in an interatrial septum between a right atrium and a left atrium of the mammal at approximately a fossa ovalis to provide a working track for the device assembly into the left atrium. In some embodiments, the guidewire is coaxially located and slidably engaged within the first lumen. In some embodiments, the device assemblies comprise a guide catheter, wherein the guide catheter is coaxially located within the first lumen, and wherein the guide catheter comprises a second lumen within which the guidewire is configured to slide. In some embodiments, excised tissue by the tissue cutter from an interatrial septum is captured and maintained, at least by the tissue cutter. In some embodiments, the tissue cutter comprises a self-expandable stent with a distal edge that is blunt, rounded, squared, or hexagonal shaped so that the distal edge does not puncture an interatrial septum before any RF energy is applied to the interatrial septum. In some embodiments, the tissue cutter comprises a self-expandable stent and a flexible metal loop attached at or near a distal end of the stent. In some embodiments, the tissue cutter comprises one or more of: a flexible metal loop; a self-expandable coil; a self-expandable stent; a self-expandable metal wire; a rolled sheet; one or more self-expandable posts; a hinged strut; a balloon; a self-expandable mesh; a mechanically-actuated jaw; or a combination thereof. In some embodiments, the expandable tissue cutter is configured to be expanded by one or more energy biasing element. In some embodiments, the expandable tissue cutter is configured to be expanded by mechanical actuation, e.g., via an umbrella mechanism. In some embodiments, the expandable tissue cutter is configured to be self-expanding such that it assumes full expansion from its collapsed state upon unsheathing/unconstraining the tissue cutter. In some embodiments, the tissue cutter comprises a mesh, the mesh configured to help retain excised tissue within the tissue cutter. In some embodiments, the tissue cutter is configured to be withdrawn into the delivery lumen collapsed, wherein the tissue stabilizer is simultaneously fully collapsed inside the tissue cutter, capturing an excised tissue therein. In some embodiments, a cutting dimension of the expandable tissue cutter is adjustable and wherein a dimension of the expandable tissue stabilizer is adjustable. In some embodiments, a distal end of the tissue stabilizer catheter is configured to extend along a track of a guidewire and pass through an initial puncture site such that the tissue stabilizer also extends past an interatrial septum into a left atrium. In some embodiments, the tissue stabilizer is coaxially expanded within a left atrium such that a dimension thereof is large enough to prevent the tissue stabilizer from pulling back through an initial puncture site and such that the tissue stabilizer provides a supporting, tensioning effect on an interatrial septum around the initial puncture site. In some embodiments, the expandable cutter is configured to be slidably advanced and coaxially expanded to a cutting dimension greater than an expanded dimension of the tissue stabilizer. In some embodiments, the tissue cutter catheter is configured to extend distally until an fully expanded tissue cutter engages a right atrial side of an interatrial septum at or about the fossa ovalis, such that the tissue cutter pierces and cuts completely through an interatrial septum, thereby creating an interatrial pressure relief opening in the interatrial septum, wherein the interatrial pressure relief opening is sufficiently large to allow blood flow through the interatrial pressure relief opening from the left atrium to the right atrium such that no more than 50% of left atrial blood is shunted to the right atrium, and wherein the interatrial pressure relief opening is sufficiently large, and/or of such shape, in order to slow a natural healing process of the tissue to maintain patency of the interatrial pressure relief opening in the interatrial septum without implanting a stent or valve therein. In some embodiments, the tissue stabilizer is configured to be partially collapsed and the tissue stabilizer catheter is configured to be retracted until the excised tissue is captured and at least a portion of the partially collapsed tissue stabilizer is pulled into an opening of the tissue cutter, with the tissue cutter being at least partially expanded. In some embodiments, the tissue stabilizer or the tissue cutter comprises: an inflatable balloon; expanding tines; an expanding mesh; at least one curved wire; an expanding plate; an expanding disc; an expanding fan; a spring coil; at least one strut; at least one hinged arm; an umbrella stretcher; or a combination thereof. In some embodiments, a tissue stabilizer material for anything other than an inflatable balloon comprises a shape memory alloy comprising: nitinol; nickel-titanium; copper-aluminum-nickel; or zinc-gold-copper. In some embodiments, a tissue cutter material comprises a shape memory alloy comprising: nitinol; nickel-titanium; stainless steel; copper-aluminum-nickel; zinc-gold-copper; or a combination thereof. In some embodiments, the tissue cutter comprises: a wire mesh; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, an expanded dimension of the tissue stabilizer is greater than an expanded dimension of the tissue cutter. In some embodiments, an expanded dimension of the tissue cutter is between about 1% and about 50% smaller than the expanded dimension of the tissue stabilizer. In some embodiments, the tissue cutter is configured to cut an aperture or hole that is: circular in shape; oval in shape; triangular in shape; squared shaped; rectangular in shape; or polygon in shape; or a combination thereof. In some embodiments, an expanded dimension of the tissue stabilizer is less than an expanded dimension of the tissue cutter. In some embodiments, an expanded dimension of the tissue cutter is between about 1% and about 50% larger than the expanded dimension of the tissue stabilizer. In some embodiments, an expanded dimension of the tissue stabilizer is greater than an expanded dimension of the tissue cutter. In some embodiments, an expanded dimension of the tissue stabilizer is between about 1% and about 50% larger than the expanded dimension of the tissue cutter. In some embodiments, the device assemblies comprise a hydrophilic coating on the guidewire. In some embodiments, the device assemblies comprise a hydrophobic coating on the guidewire. In some embodiments, the device assemblies comprise a force/pressure sensor incorporated into the distal tip of the guidewire. In some embodiments, the device assemblies comprise an oxygen saturation detection sensor incorporated into the guidewire. In some embodiments, a sensor or several sensors are incorporated into any one or more of the catheters of the device. In some embodiments, a sensor or several sensors are incorporated into the tissue cutter. In some embodiments, a sensor or several sensors are incorporated into the tissue stabilizer. In some embodiments, the device assemblies comprise a cutting point or edge incorporated into a distal tip of the guidewire. In some embodiments, the device assemblies comprise a curved or shaped end incorporated into a distal tip of the guidewire. In some embodiments, the tissue stabilizer comprises radiopaque marker bands at strategic locations so as to: orient device positioning within a body, orient its relationship to other system components, and to permit visibility and confirmation of its deployment state. In some embodiments, the tissue stabilizer and/or tissue cutter provides embolic protection by ensuring that any excised tissue is captured and retained within the device assembly. In some embodiments, the tissue stabilizer comprising the inflatable balloon comprises a protective skirt that protects proximal edges of the inflated balloon. In some embodiments, the protective skirt expands and collapses relative to a state of the balloon. In some embodiments, the tissue stabilizer and/or the tissue cutter comprises: an expanding mesh; an expanding plate; an expanding disc; an expanding fan; expanding posts or tines; or an expanding coil; wherein the tissue stabilizer and/or the tissue cutter is fabricated from a shape memory alloy that expands in an outward direction to assume an orientation at an approximately 90° angle with respect to the interatrial septum after completely passing through an interatrial septum, and is configured to be pulled back to engage the septum, to stabilize it prior to and after engagement with the tissue stabilizer or tissue cutter, and wherein, following engagement of the tissue cutter, the tissue stabilizer is collapsed in the same direction from which it opened, capturing an excised portion of tissue cut from the septum as the tissue cutter is resheathed such that the excised tissue and tissue stabilizer collapse into the delivery catheter. In some embodiments, the tissue stabilizer and/or tissue cutter comprises: at least one strut; at least one hinged arm; or an umbrella stretcher; wherein the tissue stabilizer expands in an outward direction to assume an orientation at an approximately 90° angle with respect to the interatrial septum after completely passing through an interatrial septum, and is configured to be pulled back to engage the septum, to stabilize it prior to and after engagement with the tissue stabilizer or tissue cutter; and wherein following activation of the tissue cutter, the tissue stabilizer is collapsed back in the same direction from which it opened, capturing an excised tissue cut from the septum as the tissue cutter is resheathed such that the excised tissue and tissue stabilizer collapse into the delivery catheter. In some embodiments, the tissue stabilizer comprises: at least one curved wire; or a spring coil; wherein the tissue stabilizer is fabricated from a shape memory alloy that is configured to expand after completely passing through the septum, in an outward direction transverse to a proximal-distal axis and having a radial dimension that is greater than or less than a tissue cutter dimension and is configured to be pulled back to engage the septum, to stabilize it prior to and after engagement with the tissue cutter; and wherein following activation of the tissue cutter, the tissue stabilizer is collapsed in the same direction from which it opened, capturing an excised portion of tissue cut from the septum as the tissue cutter is resheathed such that the excised tissue and tissue stabilizer fit into the delivery catheter. In some embodiments, the expandable tissue stabilizer is self-expanding when unsheathed. In some embodiments, the expandable tissue cutter is self-expanding when unsheathed. In some embodiments, the delivery catheter is wire-reinforced or braided. In some embodiments, the delivery catheter comprises a reinforced distal tip. In some embodiments, the delivery catheter includes a bend radius of about 0.5 inches to about 4 inches. In some embodiments, the guide catheter is configured to bend in a predetermined manner towards an interatrial septum. In some embodiments, the expandable cutter, after expansion, is configured to create a plurality of perforations in an interatrial septum. In some embodiments, the expandable tissue cutter is configured to translate through the interatrial septum, thereby creating a complete cut at the interatrial septum following expansion. In some embodiments, the tissue cutter comprises a proximal edge and a distal edge. In some embodiments, the proximal edge does not expand when the tissue cutter is fully expanded. In some embodiments, the tissue stabilizer comprises more than one expandable mesh discs, at least one of the more than one expandable mesh discs expands when proximal to an interatrial septum and in a right atrium. In some embodiments, two of the plural expandable mesh discs sandwich the interatrial septum in between discs when expanded. In some embodiments, two of the plural expandable mesh discs contact and sandwich the interatrial septum in between discs when expanded. In some embodiments, the tissue stabilizer comprises more than one expandable mesh discs, one of the plural expandable mesh discs is configured to plug a distal opening of the tissue cutter or a distal opening of the delivery catheter when the tissue stabilizer is resheathed. In some embodiments, one of the plural expandable mesh discs is configured to capture a distal end of the tissue cutter when the tissue stabilizer is resheathed. In some embodiments, the one of the plural expandable mesh discs includes a width that is greater than a width of a distal end of the tissue cutter. In some embodiments, the plural expandable mesh discs comprise shape memory alloy or metal. In some embodiments, the tissue cutter comprises a stent. In some embodiments, the tissue cutter comprises one or more of: a plurality of stent cells formed by struts, a plurality of struts that are optionally distally connected, a metal loop, and a fine mesh. In some embodiments, the metal loop is flexible and the plurality of struts is radially-distributed and connected to the tissue cutter catheter. In some embodiments, the metal loop is at least partly conductive or at least partly non-conductive. In some embodiments, the metal loop comprises shape memory material or non-shape memory material. In some embodiments, the plurality of struts comprises shape memory material, rigid material, energy biasing material, or a combination thereof. In some embodiments, the plurality of struts is at least partly conductive or at least partly non-conductive. In some embodiments, the fine mesh is configured to facilitate retention of excised tissue within the device assemblies post-cutting. In some embodiments, the tissue cutter comprises shape memory material, energy biasing material, or both. In some embodiments, the delivery catheter further comprises a split sheath catheter configured to enable sheathing and unsheathing of the tissue cutter. In some embodiments, the delivery catheter further is a split sheath catheter configured to enable sheathing and unsheathing of the tissue cutter. In some embodiments, the tissue stabilizer comprises a fine mesh configured to facilitate retention of excised tissue within the device assemblies post-cutting. In some embodiments, the device assembly further comprises a dilator tip configured to facilitate passage of the device assembly over a guidewire and/or across an interatrial septum.

Disclosed herein, in some embodiments, are methods for excision of an interatrial septum of a mammal for treating congestive heart failure using a transcatheter device assembly, the methods comprising: advancing an expandable tissue cutter over a guidewire and across the interatrial septum to a left atrium, the expandable tissue cutter in a compressed state; expanding and moving the tissue cutter to provide tensioning to the interatrial septum in the left atrium; translating the tissue cutter to be in contact with the interatrial septum; transmitting RF power between an RF cathode and an RF anode across the interatrial septum thereby creating an aperture, wherein the RF cathode or the RF anode is located on the expandable tissue cutter and the other of the RF cathode or the RF anode is located on a delivery catheter or in contact with tissue of the mammal; and resheathing the expandable tissue cutter into the delivery catheter with the cut interatrial septum. In some embodiments, an expandable tissue stabilizer is deployed on the opposite side of the interatrial septum to provide tissue stabilization prior to transmitting RF power across the interatrial septum, thereby creating an aperture.

Disclosed herein, in some embodiments, are methods for excision of an interatrial septum for treating congestive heart failure using a transcatheter device assembly, the methods comprising: advancing an expandable tissue stabilizer across the interatrial septum, the expandable tissue stabilizer in a compressed state; deploying and moving the tissue stabilizer to provide tensioning to the interatrial septum in the left atrium; delivering an expandable tissue cutter to a right atrium, the expandable tissue cutter in a second compressed state housed in a delivery catheter of the device assembly; expanding the expandable tissue cutter in the right atrium; translating the tissue cutter forward to be in contact with the interatrial septum, thereby sandwiching the interatrial septum between the expandable tissue cutter and the expandable tissue stabilizer; transmitting RF power between an RF cathode and an RF anode across the interatrial septum, thereby creating an aperture, wherein the RF cathode or the RF anode is located on the expandable tissue stabilizer; and resheathing the expandable tissue cutter and the expandable tissue stabilizer into the delivery catheter with the excised tissue. In some embodiments, the methods comprise allowing vascular access of the device assembly through a femoral vein. In some embodiments, the method comprises puncturing through a fossa ovalis of an interatrial septum and advancing a guidewire to a left atrium. In some embodiments, the tissue stabilizer and/or the tissue cutter is advanced over a guidewire. In some embodiments, no guidewire is required, and the device (any device described herein) is advanced across the septum without pre-puncture by a guidewire, and without being guided by a guidewire. In some embodiments, expanding the expandable cutter in the right atrium comprises translation of the delivery catheter relative to the tissue cutter. In some embodiments, the guidewire remains in the left atrium following transseptal puncture. In some embodiments, the excised tissue comprises at least a portion of the interatrial septum. In some embodiments, deploying the tissue stabilizer comprises deploying more than one tissue stabilizing disc simultaneously or at different time points. In some embodiments, one of said tissue stabilizing discs is deployed in the left atrium. In some embodiments, one of said tissue stabilizing discs is deployed in the right atrium. In some embodiments, the methods comprise removing the resheathed device assembly from the subject. In some embodiments, advancing the guide catheter over the guidewire to the interatrial septum comprises advancing the guide catheter out of the delivery catheter. In some embodiments, puncturing through a fossa ovalis of an interatrial septum is performed using an off-the-shelf transseptal kit. In some embodiments, resheathing of the tissue cutter and the tissue stabilizer comprises plugging a distal opening of the delivery catheter with the tissue stabilizer. In some embodiments, resheathing of the tissue cutter and the tissue stabilizer comprises plugging a distal opening of the tissue cutter with the tissue stabilizer during resheathing. In some embodiments, the methods comprise removing the resheathed device assembly from the subject.

In some embodiments, off-the-shelf transseptal puncture kits are configured for use with the transcatheter interatrial septum excision device assemblies herein, thus simplifying the design of the transcatheter interatrial septum excision device by removing the penetrating tip and guidewire from the main device assembly, and thereby reducing complexity and cost. An example of such an off-the-shelf transseptal puncture kits is the Swartz™ Braided Transseptal Guiding Introducers LAMP™ Series, model number 407366, with a 180 cm length with a 0.035 inch diameter. In some embodiments, an off-the-self vascular access sheath is used to deploy the device assembly into the femoral vein.

Guidewire

In some embodiments, a guidewire is placed across the interatrial septum using standard transseptal puncture techniques and provides a working track along which the device assembly is advanced. In some embodiments, individual components of the device are translated along the guidewire in relation to one another and the interatrial septum. In some embodiments, a guidewire is included in the device assembly. In some embodiments, a guidewire is not included in the device assembly. In some embodiments, the guidewire features an expandable element at its distal end to act as a tissue stabilizer and tissue retention element.

Guide Catheter

In some embodiments, a rigid guide catheter with a pre-bent shape to guide the tissue cutter towards the septum at a substantially perpendicular orientation is included in the device assemblies herein. In some embodiments, this alignment is also accomplished using a steerable or deflectable catheter. In some embodiments, the guide catheter has a central lumen, through which the guidewire passes. In some embodiments, a guide catheter is not required at all; in these embodiments, a pre-bent shape, steerability or deflectability is incorporated as a feature of the guidewire, catheter 1, catheter 2, catheter 3, catheter 4, or their combinations.

(Expandable) Tissue Stabilizer/Tissue Retention Element

In some embodiments, a tissue stabilizer provides counter tension to the interatrial septum during activation of the tissue cutter so as to minimize any unintended tissue deformation, rotation, or displacement due to unbalanced forces. In some embodiments, the tissue stabilizer also provides tension to the interatrial septum so as to minimize wall motion as the heart beats. In some embodiments, the tissue stabilizer also doubles as a tissue retention element to prevent the excised tissue from inadvertently coming free from the device assembly, and permits translation and packing of the excised tissue into the delivery catheter prior to removal of the device assembly from the body. In some embodiments, the tissue stabilizer includes one or more of: a balloon, a self-expanding mesh, a coil, and manually actuated flexible struts. In some embodiments, the tissue stabilizer is connected to catheter 2 (e.g., the tissue stabilizer catheter), which features a central lumen that permits internal translation/passage of the guidewire and/or guide catheter. In some embodiments, the tissue stabilizer is connected to the guidewire and is made of a self-expanding mesh that is constrained within a separate catheter prior to delivery to the left atrium. In some embodiments, this self-expanding mesh resides in a collapsed state within the guide catheter (catheter 1) prior to deployment. In some embodiments, the RF anode is incorporated into the tissue stabilizer. In some embodiments, a distinct tissue stabilizer is not needed, as these functions are performed by the tissue cutter. In some embodiments, the tissue cutter is deployed within the left atrium and pulled backwards, thereby dually serving the purpose of tissue stabilization and retention.

(Expandable) Tissue Cutter/Cutting Element

In some embodiments, an RF electrosurgery tissue cutter, or equivalently herein, an RF electrosurgery tissue cutter, includes an expanding structure that features an exposed conductive surface area. In some embodiments, the tissue cutter is delivered to the septum and, upon deployment/expansion, energization and actuation, excises a portion of tissue to yield a prescribed aperture. In some embodiments, the tissue cutter is connected, by conductive wire that runs along the length of catheter 3 (tissue cutter catheter), to the RF generator, and acts as the RF cathode directing energy into tissue. In some embodiments, this conductive wire is embedded within the walls of catheter 3 or alternatively run within or along the length of other catheters in the device assembly. In some embodiments, it is advantageous for the tissue cutter to have a very small surface area of exposed conductive material such that energy density immediately adjacent to the tissue cutter is concentrated highly enough to achieve a desired tissue effect. In some embodiments, the very small surface area of exposed conductive material is in the range of about 0.01% to about 50% percent of the total surface area of the tissue cutter. In some embodiments, the very small surface area of exposed conductive material is in the range of about 0.01% to about 1% percent of the total surface area of the tissue cutter. In some embodiments, the very small surface area of exposed conductive material is in the range of about 0.1% to about 1% percent of the total surface area of the tissue cutter. In some embodiments, the very small surface area of exposed conductive material is in the range of about 0.1% to about 5% percent of the total surface area of the tissue cutter. In some embodiments, the very small surface area of exposed conductive material is in the range of about 0.1% to about 10% percent of the total surface area of the tissue cutter. In some embodiments, the very small surface area of exposed conductive material is in the range of about 1% to about 15% percent of the total surface area of the tissue cutter. In some embodiments, it is desirable to selectively energize discrete portions of the tissue cutter in rapid succession to maintain high energy density surrounding the energized portion of the tissue cutter without the need to energize the entire tissue cutter at once. In some embodiments, it is also advantageous to maintain a small, defined gap between the tissue cutter and the interatrial septum during energy application to permit electric arcing and minimize any undesired thermal effects to the tissue. In some embodiments, such gap is maintained through methods of device use or through device features incorporated to ensure the gap is maintained. In some embodiments, it is advantageous to rotate or oscillate/vibrate the tissue cutter during or following tissue excision to prevent, minimize, or disrupt char formation.

In some embodiments, RF is any frequency or combination of frequencies within the electromagnetic spectrum which is/are associated with radio waves. When an RF current, voltage, and/or power is supplied from an RF cathode, the current then propagates through tissue, and/or any other RF conductive media between the RF cathode and RF anode.

In some embodiments, an RF cathode is the electrode from which an RF current leaves; such current is in the direction in which positive electrical charges move. In some embodiments, an RF anode is the electrode from which RF current flows into. In some embodiments, an RF cathode or anode is a single-point electrode, a ring electrode, a plate electrode, a pointed electrode, a blade-shaped electrode, a patch electrode, or any other types of electrodes.

In some embodiments, the device herein, such as the tissue cutter is configured to be used in electrosurgery, with the application of a radio frequency alternating polarity electrical current to tissue as a means to cut. In electrosurgical procedures, the tissue is heated by the RF electric current. In some embodiments, only the tissue to be cut is heated without heating other tissue in its close vicinity. In some embodiments, only part of the tissue to be cut is heated. In some embodiments, such heating of tissue is controlled by the size, shape, and/or geometry of the conductive region of the tissue cutter. In some embodiments, the tissue is heated to a predetermined temperature, or a predetermined range of temperatures. In some embodiments, the tissue to be cut is heated to no less than 60° C., 70° C., 80° C., 90° C., 100° C. or even higher temperatures. In some embodiments, the tissue to be cut is heated to be in the range of 50° C. to 100° C.

RF Energy Sink (RF Anode or RF Return)

In some embodiments, an RF anode acts as a RF current sink for the RF cathode to define the field in which RF energy is transmitted within the body of the mammal. In some embodiments, the device assembly disclosed herein includes an RF energy sink (RF anode, or RF return) to draw RF energy from the RF cathode out of the body, thus defining the field across which RF energy is transmitted. Referring to FIG. 1, in some embodiments, the RF generator 117 generates RF current that is transmitted to the RF cathode 103b via a conductive wire, e.g., a straight wire, a coaxial cable. In some embodiments, the RF cathode transmits RF energy via RF current/voltage through the tissue 107 to the RF anode 113b, and the RF anode receives RF energy and then transmits the energy back to the RF generator via a conductive connection. In some embodiments, the RF anode is positioned in close proximity to the RF cathode or external to, but in contact with, the body, (e.g. a skin patch electrode). In some embodiments, the RF anode is incorporated as a feature of the tissue stabilizer. In some embodiments, the RF anode is on the guidewire, the tissue stabilizer catheter, the tissue cutter catheter or the delivery catheter.

Delivery Catheter

In some embodiments, the delivery catheter is the main housing catheter for all other components of the device assembly (excluding the RF generator and, in some embodiments, the RF energy sink). In some embodiments, the tissue cutter is housed towards the distal end of the delivery catheter and ensures that the tissue cutter remains collapsed prior to deployment. In some embodiments, the delivery catheter additionally permits packing of the excised tissue within its lumen. In some embodiments, the delivery catheter features a pre-bent shape, steerability, or deflectability to facilitate orientation with respect to the interatrial septum.

RF Generator

In some embodiments, an apparatus that generates alternating current, voltage, and/or power in the radiofrequency spectrum, in the range of about 300 kHz to about 3 MHz at a power level in the range of about 5 W to about 300 W. In some embodiments, an apparatus that generates alternating current, voltage, and/or power in the radiofrequency spectrum, in the range of about 9 kHz to about 300 MHz. In some embodiments, the RF generator, stationed outside of the sterile field, is connected to the RF anode and cathode through a sterile connector that crosses into the sterile field and transmits RF energy through wires that connect to the RF anode and cathode. In some embodiments, the RF generator is operated by outputting constant voltage, constant power, and/or constant current. In some embodiments, the RF generator outputs a constant sine wave throughout the duration of tissue cutting. In some embodiments, the RF signal output is interrupted and dampened such that RF energy is applied for a fixed percentage of operation time of the device assembly, in the range of 0.01% to 99.9% of the operation time. In some embodiments, these different RF energy output modes yield varied tissue effects. In some embodiments, it is anticipated that a constant sine wave yields the desired tissue vaporization without thermal injury or char formation. In some embodiments, the RF generator includes batteries to obviate the need for wires crossing into/out of the sterile field. In some embodiments, the RF generator is within or outside the sterile field. In some embodiments, the RF generator monitors the temperature or impedance at or near the distal end of the tissue cutter and adjusts the power, voltage, or current output to ensure continuous tissue cutting. In some embodiments, the RF generator includes a pump to circulate chilled coolant such as saline through the tissue cutter catheter to regulate its temperature and minimize/prevent char formation.

In some embodiments, the RF generator includes a power source, an on/off switch, a processor, a computer memory, a communications element, an electrical connection to the RF cathode, and an electrical connection to the RF anode. In some embodiments, the RF generator is manually controlled. In some embodiments, the RF generator is automatically controlled using a feedback system, e.g. temperature feedback.

In some embodiments, the RF generator includes an operating system configured to perform executable instructions. The operating system is, for example, software, including programs and data, which manages the device's hardware and provides services for execution of applications. In some embodiments, the RF generator includes a storage and/or memory device. The storage and/or memory device is one or more physical apparatuses used to store data or programs on a temporary or permanent basis. In some embodiments, the RF generator includes a display to send visual information to a user. In some embodiments, the RF generator includes an input device to receive information from a user. In some embodiments, the RF generator herein includes one or more non-transitory computer readable storage media encoded with a program including instructions executable by the operating system of an optionally networked digital processing device. In some embodiments, the RF generator herein includes at least one computer program, or use of the same. In some embodiments, a computer program includes a sequence of instructions, executable in the digital processing device's CPU, written to perform a specified task.

Figure 2:
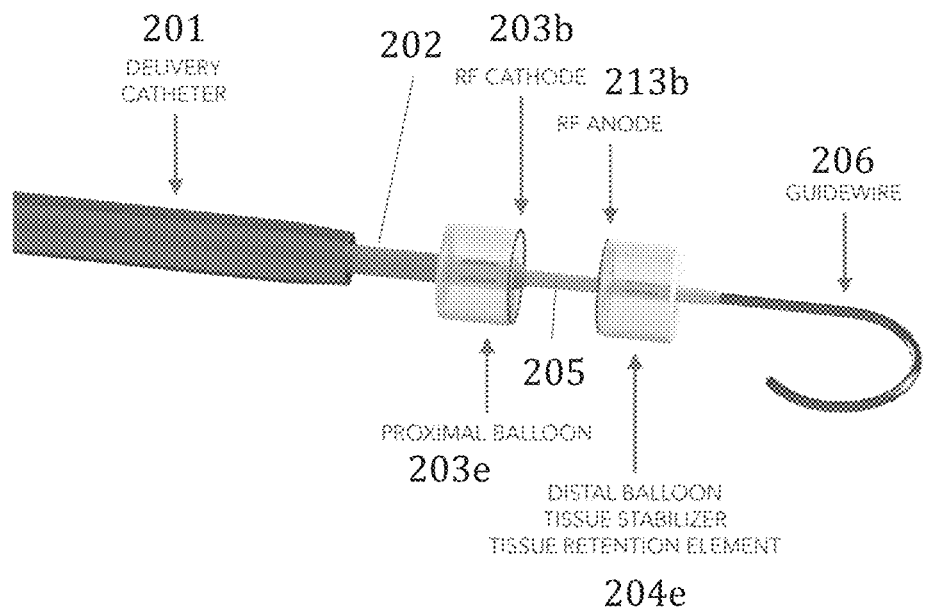
FIG. 2 is an illustration of an exemplary embodiment of the RF energy-based device assemblies for interatrial anastomosis.

Referring to FIG. 2, in some embodiments, the device assemblies include a delivery catheter 201, a tissue cutter catheter 202 to which a tissue cutting balloon 203e is attached that contains a tissue cutter cathode 203b, a tissue stabilizing balloon 204e which is attached at the distal end of a tissue stabilizer catheter 205, and a guidewire 206 which is slidably engaged within the lumen of the tissue stabilizer catheter. In some embodiments, the RF cathode 203b is located on or near the distal end of the tissue cutter, and the RF anode 213b is located on or near the proximal end of the tissue stabilizer. Both the tissue cutter and tissue stabilizer includes at least one expandable or inflatable balloon.

In some embodiments, the methods disclosed herein using the device assemblies includes one or more procedural steps selected from the following steps, but not necessarily in the exact order:
    vascular access is achieved through the femoral vein using standard techniques (e.g., Seldinger method);
    transseptal puncture through the fossa ovalis of the interatrial septum is performed using standard interventional techniques), leaving a guidewire in place;
    the device assembly is introduced, e.g., through the groin, and delivered over the guidewire to the right atrium;
    the tissue stabilizer is introduced over the guidewire and across the interatrial septum to the left atrium; there, it is expanded in diameter by inflation (in the case of a balloon), mechanical actuation or unsheathing of a self-expanding material (alternatively, the tissue cutter is introduced over the guidewire and across the interatrial septum to the left atrium; there, the tissue cutter is unsheathed by pulling its constraining catheter backwards relative to the tissue cutter);
    the tissue cutter is delivered (via delivery catheter) to the right atrium; there, the tissue cutter is unsheathed within the right atrium by pulling its constraining catheter backwards (Alternatively, the tissue stabilizer is delivered (via delivery catheter) to the right atrium; there, it is expanded in diameter by inflation (in the case of a balloon), mechanical actuation, or unsheathing of a self-expanding material);
    after (or in the process of) unsheathing, the tissue cutter is fully expanded;
    the tissue cutter is translated over the guidewire until it is in touching the interatrial septum, thus sandwiching the tissue between the tissue cutter and tissue stabilizer;
    the tissue cutter is energized, sending RF current across the septum (between the RF cathode and anode) to create an aperture whose shape is prescribed by the geometry of the tissue cutter; and
the following steps are performed in any order depending on embodiment:
    the tissue cutter is collapsed;
    the tissue stabilizer is pulled backwards with respect to the delivery catheter, thereby packing the excised tissue within the delivery catheter;
    the tissue stabilizer is collapsed; and
    the device is removed from the body.

Stents

In some embodiments, the tissue cutter disclosed herein includes a stent. In some embodiments, the tissue cutter takes the form of a self-expanding (e.g., shape memory material) stent, which is sharpened along the full length of its distal edge, and self-expands upon deployment from the delivery catheter (catheter 4, not shown) within the right atrium. The tissue cutter is fully insulated with the exception of its distal edge; its proximal end is attached to the tissue cutter catheter and is coupled to the RF generator by a wire that runs within or along the tissue cutter catheter, In some embodiments, the tissue cutter catheter features a central lumen that contains the guidewire, guide catheter, and tissue stabilizer.

In some embodiments, the device is advanced over a guidewire, with the tissue stabilizer being attached to its respective catheter (catheter 2), and delivered across the septum where it is actuated to fully expand. In some embodiments, the delivery catheter (catheter 4) is pulled backwards with respect to the tissue cutter catheter, thereby exposing and expanding the stent and tissue cutter. In some embodiments, the RF anode is incorporated into the tissue stabilizer, which for example, is a ring electrode on the tissue stabilizer catheter (in the left atrium), or a pad placed on the surface of the body of the mammal Once properly positioned, in some embodiments, the tissue cutter is energized by the RF generator, resulting in tissue disruption and excision. In some embodiments, the tissue cutter, excised tissue and tissue stabilizer are collapsed within the delivery catheter (catheter 4) and the device is removed from the body.

In some embodiments, the tissue cutter disclosed herein includes a stent. In some embodiments, as illustrated in FIGS. 3A-3C, the tissue cutter takes the form of a self-expanding (e.g., shape memory material) stent. In some embodiments, the stent pattern is laser-cut onto a shape memory material cylindrical tube. In some embodiments, the stent 303 has approximately diamond pattern shaped cells. In some embodiments, the stent cells are of other shapes, for example, circle, triangle, rectangular, etc. In some embodiments, as illustrated by FIG. 3C, the stent 303 has at least three axisymmetric struts 303*m* that are distally connected by a ring 303*b* at its expanding diameter. The ring 303*b* in some embodiments is within (coaxially closer to the longitudinal axis of the catheter 302 of FIG. 3A) the stent 303 of FIG. 3A, as an alternative to the ring 303*b* shown in FIG. 3B. Alternatively, the embodiment ring of FIG. 3C is used as a stabilizer externally (further from the longitudinal axis of the catheter 302 of FIG. 3A) and coaxially with the embodiment of FIG. 3A. Alternatively, the embodiment of FIG. 3C is used as a tissue cutter with the ring 303*b* being sharpened for cutting the septum, or energized for cutting the septum using RF energy (as a cathode). In some embodiments, as illustrated by FIGS. 3A-3B, the stent tips 303*j* are sharpened at its distal edge and can penetrate through the interatrial septum and act as an anchoring mechanism to position the stent substantially perpendicular to the interatrial septum. In some embodiments, the stent 303 is fully insulated 303*h* with the exception of its distal tips 303*j*, the crowns of the struts 303*k*, the valleys of the struts 303*l* and/or the ring 303*b*. In some embodiments, the proximal end of the stent is attached to the tissue cutter catheter 302 and is coupled to the RF generator by a wire (not shown) that runs within or along the tissue cutter catheter. In some embodiments, the stent is (partially) insulated or comprised of a non-conductive material such as: Parylene; PTFE. In some embodiments, the stent self-expands upon deployment from a catheter (delivery catheter or tissue stabilizer catheter, not shown) within the right atrium or the left atrium, with the expanding diameter facing the interatrial septum. In some embodiments, once properly positioned, the tissue cutter is energized by the RF generator and translates through the interatrial septum, resulting in tissue disruption and excision. In some embodiments, the stent is fully insulated with exception of its distal tips and the sharpened edge, once properly positioned (the distal tips have penetrated through the interatrial septum), the tissue cutter is energized by the RF generator and the tissue cutter is rotated, resulting in tissue disruption and excision. In some embodiments, the self-expanding stent is deployed within the left atrium using a split sheath catheter with a tapered, penetrating tip to facilitate crossing the interatrial septum. In some embodiments, the split sheath is moved distally to unsheath the stent 303 which distal edge faces the interatrial septum. FIG. 3B, in a particular embodiment, shows a metal wire loop 303*b* that is tethered through small holes 303*n* at multiple points in the crowns of the struts 303*k*, thus maintaining a gap between the loop and distal edge of the stent. In this embodiment, the stent 303 is fully insulated with exception of its distal tips 303*j* and the crowns of the struts 303*k*. In some embodiments, the loop 303*b* is sutured, welded, soldered, brazed, glued, threaded, or wrapped through, in, or around the distal edge of the stent. In some embodiments, the loop 303*b* takes the form of a circle, polygon, lasso, or any other geometrical shapes once the stent is fully expanded. In some embodiments, the stent merely acts as a self-expanding scaffold to expand the metal loop to a desired geometry. In some embodiments, the self-expanding stent is a braided stent in a tubular mesh configuration. In some embodiments, the tissue cutter catheter 302 features a central lumen that contains the guidewire, guide catheter, and tissue stabilizer.

In some embodiments, the stent tissue cutter is deployed within the left atrium over a guidewire, with its uninsulated/cutting edge oriented towards the interatrial septum. In some embodiments, the tissue stabilizer is excluded from the transcatheter interatrial septum excision device. As illustrated in FIGS. 4A-4D, the stent tissue cutter 403 is collapsed and housed in a split sheath catheter 408. In some embodiments, catheter 408 comprises a cap 408*a* and a shaft 408*e*. The catheter shaft has a central lumen 408*f* that is slidably engaged with the guidewire 406. The cap 408*a* has a tapered, penetrating tip 408*d* to facilitate catheter 408 in crossing the interatrial septum (over the guidewire) from the right atrium to the left atrium. The cap of catheter 408*a* has a second lumen 408*b* that houses the collapsed stent tissue cutter 403. FIG. 4D shows a detailed view of FIG. 4C. In some embodiments, the stent tissue cutter is partially insulated with insulation 403*h*, leaving its cutting edge 403*b* exposed (oriented to face the septum), and its back end coupled to the RF generator through a wire (not shown). In some embodiments, the stent tissue cutter 403 is attached to tissue cutter catheter 402, having a central lumen, slidably engaged with the shaft 408*e* of catheter 408. In some embodiments, a centralizer 411 having a central lumen mounted to the outer diameter of tissue cutter catheter 402 and the internal diameter of the stent tissue cutter 408*e* is incorporated. In some embodiments, the stent tissue cutter 403 is coupled to the RF generator by a conductive wire that runs within or along tissue cutter catheter 402. In some embodiments, an electrode is placed external to, but in contact with, the body (e.g. a skin patch electrode) to act as the RF anode. In some embodiments, a ring electrode resides on tissue cutter catheter 402 within the right atrium and acts as the RF anode, thereby eliminating the need for an externally-placed RF anode.

In some embodiments, the device assembly 400 is advanced forward to the left atrium such that the cap 408*a* of catheter 408 crosses the septum 407. The tissue cutter catheter 402 and the delivery catheter 401 are held stationary as catheter 408 is advanced forward to unsheath the stent tissue cutter 403 and deploy its cutting edge. In some embodiments, the cutting edge of the stent tissue cutter is brought in contact with the septum 407 by pulling the tissue cutter catheter 402 backwards such that RF energy is delivered. In some embodiments, post-tissue cutting, the stent tissue cutter 403 is collapsed by sliding catheter 408 backwards (proximally) with respect to tissue cutter catheter 402 that is stationary or moved distally to support the stent to collapse in the cap 408*a*. In some embodiments, the excised tissue is packed within the stent 403 itself, followed by the second lumen 408*b* of the cap 408*a* of catheter 408. In some embodiments, the tissue cutter dually acts as a tissue retention element, given that the excised tissue remains within to the tissue cutter post-tissue excision.

In some embodiments, the tissue cutter remains in the right atrium. The device is advanced over a guidewire, with the tissue stabilizer being attached to its respective catheter (catheter 2), and delivered across the septum where it is actuated to fully expand. In some embodiments, the delivery catheter (catheter 4) is pulled backwards with respect to the tissue cutter catheter, thereby exposing and expanding the stent tissue cutter. In some embodiments, the RF anode is incorporated into the tissue stabilizer, which for example, is a ring electrode on the tissue stabilizer catheter (in the left atrium), or a pad placed on the surface of the body of the mammal Once properly positioned, in some embodiments, the tissue cutter is energized by the RF generator, resulting in tissue disruption and excision. In some embodiments, the tissue cutter, excised tissue and tissue stabilizer are collapsed within the delivery catheter and the device is removed from the body.

In some embodiments, the stent tissue cutter has a blunt, rounded, squared, or hexagonal shaped distal edge such that it does not puncture the tissue before RF energy is applied to the septum; it merely engages the tissue along the length of its distal edge prior to energy application.

In some embodiments, the stent tissue cutter is comprised of a shape memory material such as: nickel-titanium; copper-aluminum-nickel; zinc-gold-copper; or a combination thereof.

In some embodiments, the stent is fully insulated or comprised of a non-conductive material. In some embodiments, the tissue cutter includes a flexible, metal loop, e.g., 303b, affixed to the distal end of the stent at one or multiple points. In some embodiments, electric arcing is generated between the flexible metal loop and the tissue thus facilitate tissue cutting, e.g., FIGS. 3A-3B. In some embodiments, the stent merely acts as a self-expanding scaffold to expand the metal loop to a desired geometry. In some embodiments, the stent features pointed tips, e.g., 305, that penetrate the tissue and act as an anchoring mechanism to position the stent substantially perpendicular to the septum. In some embodiments, the metal loop is sutured, welded, soldered, brazed, glued, threaded, or wrapped through, in, or around the distal edge of the stent. In some embodiments the metal loop takes the form of a circle, polygon, or lasso once the stent is fully expanded.

In some embodiments, the metal loop follows the contours of the teeth at the distal edge of the stent. In some embodiments, the metal loop is anchored at discrete points, thus maintaining a gap between the metal loop and stent between anchoring points. In some embodiments, the metal loop is anchored to the distal edge of the stent.

In some embodiments, the transcatheter interatrial septum excision device includes a split catheter. In embodiments shown in FIGS. 4 and 5, the split sheath catheter 408 together with catheter 401 form the delivery catheter whose lumen 408b, together with the lumen of catheter 401, form the delivery lumen; and split sheath catheter 508, together with catheter 501, form the delivery catheter whose lumen 508b, together with the lumen 501a, form the delivery lumen.

In some embodiments, the tissue cutter and tissue stabilizer are both self-expanding stents with an uninsulated edge on each stent acting as the RF cathode 503b and anode 513b, respectively. Referring to FIGS. 5A-5D, catheter 508 comprises a cap 508a and a shaft 508e, the catheter shaft having a central lumen (not shown), slidably engaged with the guidewire (not shown); the cap has a tapered tip 508d to facilitate the catheter in crossing the septum 507 (over the guidewire) from the right atrium to the left atrium; the cap of catheter 508a features a second lumen 508b that houses the collapsed tissue stabilizer 504. In some embodiments, the tissue stabilizer 504 is partially insulated 504h, leaving its uninsulated edge exposed, and is mounted to the distal aspect of the tissue stabilizer catheter 505. In some embodiments, a conductive wire connects the tissue stabilizer to the RF generator, running within the walls of the tissue stabilizer catheter 505. In some embodiments, the stent tissue cutter 503 is at least partially insulated 503h, leaving its uninsulated edge exposed, and is mounted to the distal end of the tissue cutter catheter 502. In some embodiments, a conductive wire connects the tissue cutter to the RF generator, running at least partly within the walls of the tissue cutter catheter 502. In some embodiments, the tissue cutter catheter 502 has a central lumen that is slidably engaged with the tissue stabilizer catheter 505. In some embodiments, a delivery catheter 501 has a central lumen that is slidably engaged with the tissue cutter catheter 502. In some embodiments, a centralizer 511 having a central lumen mounted to the outer diameter of the tissue stabilizer catheter 505 and the internal diameter of the tissue stabilizer 504 is incorporated.

Figure 5A:
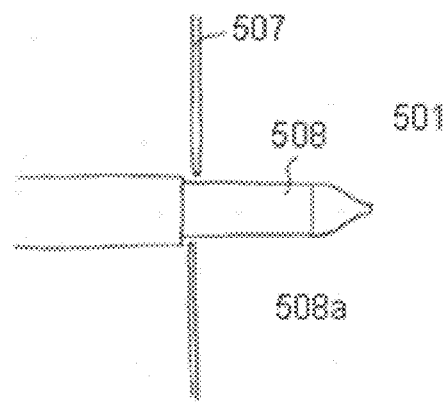
FIGS. 5A-5D show an exemplary embodiment of the RF energy-based device assemblies for interatrial anastomosis.
Figure 5B:
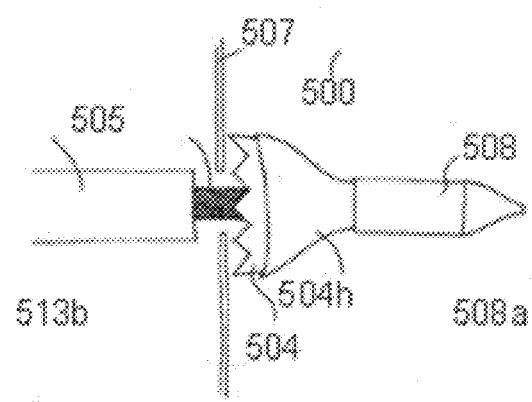
Figure 5C:
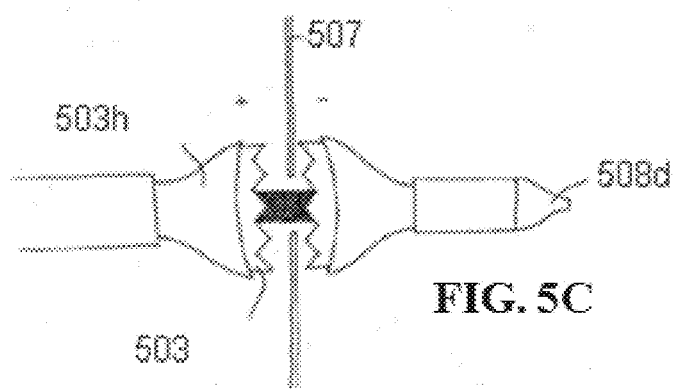
Figure 5D:
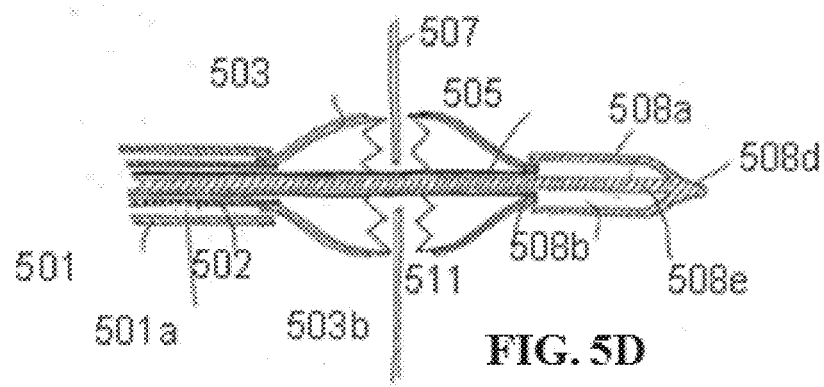

In some embodiments, as shown in FIG. 5A, the device assembly is advanced into the body over a guidewire (not shown) until the entire cap 508a of tissue stabilizer catheter 505 is advanced into the left atrium. In some embodiments, the tissue stabilizer is unsheathed and deployed in the left atrium by advancing catheter 508 forward with respect to the other device components. In some embodiments, the tissue stabilizer catheter 505 is pulled backwards with respect to other device components to bring the tissue stabilizer in contact with the septum, as shown in FIG. 5B. In some embodiments, the delivery catheter 501 is pulled back while other device components of the device assembly 500 are held stationary to unsheath and deploy the stent tissue cutter 503 within the right atrium. In some embodiments, the tissue cutter catheter 502 is advanced forward with respect to the other device components until the stent tissue cutter is in contact with the septum, as in FIGS. 5C-5D. In some embodiments, the tissue stabilizer and stent tissue cutter 'mate/coapt' on opposing sides of the septum to create a sandwiching effect. In some embodiments, energy is then applied by the RF generator to excise tissue and yield an aperture. In some embodiments, the delivery catheter is advanced to resheath the stent tissue cutter, whereas catheter 508 is pulled back to resheath the tissue stabilizer stent 504. In some embodiments, the excised tissue is pierced and retained by the tissue stabilizer catheter 505. In some embodiments, the tissue stabilizer is deployed in the right atrium and the tissue stabilizer catheter is pushed distally to make contact with the septum, whereas the tissue cutter is deployed in the left atrium and the tissue cutter catheter is pulled proximally to achieve apposition with the septum before RF energy is applied.

Struts with Metal/Wire Loop

In some embodiments, as shown in FIGS. 7A-7B, the tissue cutter includes a flexible metal loop 703 that is deployed into its expanded state through a plurality of radially-distributed struts 703d connected to the distal end of the tissue cutter catheter 702; these struts provide structural rigidity and coaxial alignment with respect to the tissue cutter catheter. In some embodiments, the metal loop folds up in a standard fold, coil, a plurality of loops/petals, an accordion, a rolled or straight configuration in its collapsed/initial state pre-deployment. In some embodiments, the metal loop is composed of wire. In some embodiments, the metal loop is cut from a cylindrical tube. In some embodiments, the metal loop comprises of a conductive shape memory metal. In some embodiments, the metal loop is comprised of a conductive non-shape memory metal. In some embodiments, the metal loop is set back (recessed) from the tips of the struts by a fixed distance (e.g. about 0.1 to about 10.0 mm). In some embodiments the metal loop features smaller loops/petals 703g that wrap around the individual struts. In some embodiments, the arc length of the metal loop is fixed. In some embodiments, the ends of the metal loop come together and run along the length of the tissue cutter catheter, such that the metal loop is be actuated as a snare loop.

In some embodiments, the struts of the tissue cutter comprise conductive shape memory material(s), such that when unconstrained (through slidable translation of its constraining catheter 712/701 with respect to the tissue cutter catheter 702), they flare open, thereby expanding the metal loop to a desired conformation, as illustrated in FIG. 7B. In some embodiments, the struts ensure coaxial alignment between the metal loop and tissue cutter catheter 702 and, by extension, with all other catheters within the device assembly (in addition to the guidewire 706). In some embodiments, the struts are pre-bent to assume U-bend configurations when fully expanded, thereby permitting the struts to bend approximately 180° backwards to orient the metal loop to face the interatrial septum (upon delivery to and deployment within the left atrium). In some embodiments, the struts are pre-bent and is configured to expand to a flared cross-section in a plane determined by the radial direction and the proximal-distal direction. (to a larger diameter than its constrained diameter). In some embodiments, the cross-section is of different shapes, such as a bell shape, a conical shape, a U-shape, or any other geometrical shape. In some embodiments, the geometry towards the tips of the struts features a step-up in width to facilitate seating of the metal loop. In some embodiments, the geometry towards the tips of the struts features a step-up in width, with narrowing of width in between to facilitate seating of the metal loop. In some embodiments, the geometry towards the tips of the struts features narrowing of its width, without a step-up in width, to facilitate seating of the metal loop. In some embodiments, the struts of the tissue cutter are not comprised of a shape memory material, but are connected to one another by energy biasing elements, such as springs, which are compressed when collapsed/constrained, but flare the struts outwards radially when unconstrained (by translating its constraining catheter backwards), thereby expanding the non-shape memory metal loop. In some embodiments, the struts are mechanically actuated through an umbrella mechanism, wherein two struts (an actuation strut and an expansion strut) are connected by a hinge point and are connected to an actuation catheter and a tissue cutter catheter, respectively, by another hinge point, such that when the actuation catheter is translated forward in relation to the tissue cutter catheter, the actuation strut rotates the expansion strut outwards radially by its hinge point on the expansion catheter. In some embodiments, this radial expansion expands a metal loop to a desired diameter by the degree in which the actuation catheter is translated. Additionally, in some embodiments, the actuation catheter is replaced by an actuation wire pulley system, whereas translation by the actuation wire expands the expansion strut. In some embodiments, the expansion mechanism is driven by the metal loop, rather than the struts to which the metal loop is attached. In some embodiments, the struts and metal loop are fully insulated or, alternatively, the struts and metal loop are comprised of a non-conductive material and a separate (conductive) metal loop is affixed to the insulated (or non-conductive) metal loop to act as the tissue cutter. In some embodiments, the struts are insulated while the metal loop is uninsulated. In some embodiments, the struts and metal loop are both partially insulated. In some embodiments, a fine mesh or membrane 703f, composed of a textile, polymer, or metal, is incorporated between and/or around the struts of the tissue cutter and connected to the metal loop 703b, as in FIG. 7A, or, alternatively, between and/or around the struts but not connected to the metal loop, or, alternatively, within the plane of the metal loop, or, alternatively, in the plane of the metal loop, but set recessed/set back to help ensure all excised tissue is retained within the device assembly post-cutting. In some embodiments, the metal loop is affixed to the distal tips of the struts; alternatively, the metal loop is set back (recessed) from the tips by a fixed distance (e.g. about 0.1 to about 10.0 mm). In some embodiments, the tissue cutter is deployed within the left atrium and pulled proximally to engage and cut tissue. In some embodiments, a split sheath catheter is used to permit sheathing and unsheathing of the tissue cutter within the left atrium. In some embodiments, the tissue cutter is deployed within the right atrium and advanced distally to engage and cut tissue.

In some embodiments, as illustrated in FIGS. 7A-7B the tissue stabilizer 704 includes one, or a plurality of, self-expanding (shape memory) struts. In some embodiments, the tips of the tissue stabilizer struts 704a are sharpened to permit penetration through the interatrial septum. In some embodiments, the tips of the tissue stabilizer struts are blunt to prevent penetration through the interatrial septum. In some embodiments, the tissue stabilizer 704 expands to assume a diameter that is greater than the expanded diameter of the tissue cutter 703 when fully deployed. In some embodiments, the tissue stabilizer expands to assume a diameter that is less than the expanded diameter of the tissue cutter when fully deployed. In some embodiments, a fine mesh or membrane 704f, composed of a textile, polymer, or metal, is incorporated between and/or around the struts of the tissue stabilizer, as in FIG. 7A, to help ensure all excised tissue is retained within the device assembly post-cutting. In some embodiments, the tissue stabilizer is fully insulated. In some embodiments, the tissue stabilizer is partially insulated, such that the [distal] tips of tissue stabilizer are uninsulated to permit RF energization. In some embodiments, the tissue stabilizer takes the form of a balloon, shape memory mesh, shape memory coil, and self-expanding (e.g., shape memory) cage. In some embodiments, the RF anode is placed on a pad external to the body on the patient's skin. In some embodiments, the RF anode resides proximal to the interatrial septum 707, but distal to the tissue stabilizer 704. In some embodiments, the RF anode resides distal to the interatrial septum, but proximal to the tissue stabilizer. In some embodiments, the tissue stabilizer is deployed within the right atrium and advanced distally to contact and stabilize tissue. In some embodiments, the tissue stabilizer is deployed within the left atrium and pulled proximally to contact and stabilize tissue. In some embodiments, a split sheath catheter, with dilator tip 715 connected to dilator tip catheter 716, is used to permit sheathing and unsheathing of the tissue stabilizer within the left atrium.

Figure 20C:
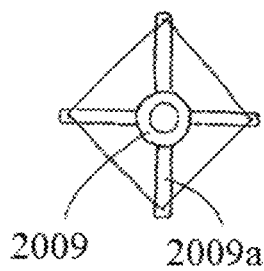
Figure 20D:
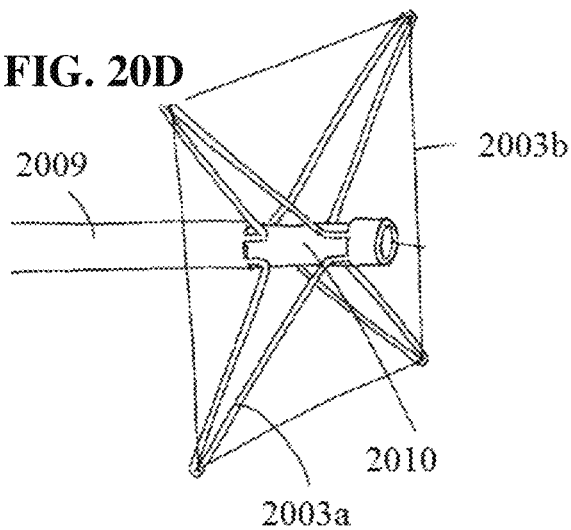

In some embodiments, as shown in FIGS. 20A-20D, the tissue cutter includes a flexible metal loop 2003b mounted to one or more struts 2009a through a series of anchor points 2009b at the distal end of an expansion catheter 2009 that features hinge points at its midpoint and proximal and distal ends of each strut to permit their bending outwards (radially) when compressed axially through translation with respect to an actuation catheter 2010 (attached to the expansion catheter 2009 at its distal end). In some embodiments, the metal loop 2003b expands as the struts are expanded (FIGS. 20B-20D). In some embodiments, the tissue cutter is deployed within the right atrium and advanced distally to engage and cut tissue, or, alternatively, is deployed within the left atrium and pulled proximally to engage and cut tissue. In some embodiments, the struts and/or catheters includes self-expanding metal, non-self-expanding metal, a polymer, or a polymer/metal blend. In some embodiments, the struts are insulated while the metal loop is uninsulated. In some embodiments, the struts and metal loop are both partially insulated. In some embodiments, a distinct tissue stabilizer or tissue stabilizer catheter is not required when the tissue cutter is deployed in the left atrium. In some embodiments, a distinct tissue stabilizer or tissue stabilizer catheter is used when the tissue cutter is deployed in the left atrium.

In some embodiments, as illustrated in FIGS. 7A-7B the device assembly includes a dilator tip 715 to facilitate passage of the device over a guidewire and across the interatrial septum.

Struts

In some embodiments, the tissue cutter includes a flexible, metal loop that is deployed into its expanded state through a series of struts connected to the distal end of the tissue cutter catheter. In some embodiments, the metal loop is folded up in a standard fold, coil, loops, accordion, rolled or straight configuration in its collapsed/initial state pre-deployment. In some embodiments, the metal loop is composed of wire. In some embodiments, the metal loop is cut from a cylindrical tube. In some embodiments, the metal loop is a shape memory metal. In some embodiments, the metal loop is set back (recessed) from the tips of the struts by a fixed distance (e.g. about 0.1 to about 10.0 mm). In some embodiments, the metal loop features smaller loops/petals that wrap around the struts. In some embodiments, the ends of the metal loop meet and run along the length of the tissue cutter catheter, such that the loop is actuated as a snare. In some embodiments, these struts comprise shape memory material(s), such that when unconstrained (through slidable translation of delivery catheter with respect to tissue cutter catheter) they flare open, thereby opening the metal loop to a desired (expanded) conformation. In some embodiments, the struts ensure coaxial alignment between the metal loop and tissue cutter catheter and, by extension, with all other catheters within the device (in addition to the guidewire). In some embodiments, the struts are pre-bent to assume U-bends when fully expanded, thereby permitting the struts to bend approximately 180° backwards and orient the metal loop to face the interatrial septum upon delivery to and deployment within the left atrium.

In some embodiments, the struts are not made of a shape memory material but are connected to one another by energy biasing element such as springs, which are compressed when collapsed/constrained, but flare the struts outward radially when unconstrained (by pulling the delivery catheter backwards), thereby expanding the non-shape memory metal loop.

In some embodiments, these struts are mechanically actuated through an umbrella mechanism, wherein two struts (an actuation strut and an expansion strut) are connected by a hinge point and are connected to an actuation catheter and a tissue cutter catheter, respectively, by another hinge point, such that when the actuation catheter is translated forward in relation to the tissue cutter catheter, the actuation strut rotates the expansion strut outwards radially by its hinge point on the expansion catheter. In some embodiments, this radial expansion expands a metal loop to a desired diameter by the degree in which the actuation catheter is translated. Additionally, in some embodiments, the actuation catheter is replaced by an actuation wire pulley system, whereas translation by the actuation wire expands the expansion strut.

In some embodiments, the metal loop comprises a conductive shape memory material and is connected to the tissue cutter catheter through a series of radially-distributed struts, which provide structural rigidity and coaxial alignment with respect to the tissue cutter catheter. In some embodiments, the expansion mechanism is driven by the metal loop, rather than the struts to which the metal loop is attached. In some embodiments, the struts and metal loop are both comprised of a conductive shape memory material, with the struts being insulated and the metal loop uninsulated. In some embodiments, the struts and metal loop is partially insulated. In some embodiments, the struts and metal loop are fully insulated, or made of non-conductive material and a separate (conductive) metal loop is affixed to the insulated (or non-conductive) metal loop to act as the tissue cutter.

In some embodiments, a fine mesh composed of a textile, polymer, or metal, is incorporated between the struts and connected to the metal loop, or within the plane of the metal loop, or parallel to the tissue plane and/or the metal loop, but set back to help ensure all excised tissue is retained within the device assembly post-cutting. In some embodiments, the metal loop is affixed to the distal tips of the struts; alternatively, the metal loop is set back (recessed) from the tips by a fixed distance (e.g. about 0.1 to about 10.0 mm) to ensure a small, defined gap between the metal loop and tissue once the strut tips engage tissue.

Cages with Metal Loop

In some embodiments, as illustrated in FIGS. 19A-19B, the tissue cutter includes a flexible metal loop 1903b on the face, e.g., distal face or distal face, of a self-expanding (shape memory) cage 1903p, that is deployed within the right atrium, thereby expanding the metal loop. In some embodiments, the metal loop is mounted on the distal face of the cage such that it makes contact with the interatrial septum 1907. In some embodiments, the proximal ends of the cage struts are connected to the distal end of the tissue cutter catheter 1902, which features a central lumen within which an actuation catheter 1914 is slidably engaged. In some embodiments, the central ends of the struts that comprise the cage face are connected to the actuation catheter 1914. In some embodiments, the delivery catheter 1901 features a central lumen and is slidably engaged with the tissue cutter catheter. In some embodiments, the cage is deployed by pulling the delivery catheter proximally and allowing the self-expanding cage to deploy, or through mechanical actuation by sliding the actuation catheter proximally with respect to the tissue cutter catheter. In some embodiments, the RF anode is placed on the tissue retention element 1904, on the tissue retention element catheter 1905, or on a pad placed external to the body on the patient's skin. In some embodiments, the metal loop comprises shape memory material and drives the full expansion of the cage when unconstrained from the delivery catheter. In some embodiments, multiple flexible, electrically-isolated metal loops are mounted to the proximal or distal face of the cage, each having a unique expanded size, ranging from about 2 mm to about 5 mm, upon expansion of the cage, such that tissue is excised by selectively directing RF energy to the metal loop corresponding to the desired aperture size.

In some embodiments, the tissue cutter includes a flexible metal loop on the proximal face (if deployed in the right atrium) or distal face (if deployed in the left atrium) of a self-expanding (shape memory) cage that is placed across the septum over a guidewire. In some embodiments, catheter comprises of a cap and a shaft. In some embodiments, the catheter shaft features a central lumen that is slidably engaged with the guidewire. In some embodiments, the catheter cap features a tapered tip to facilitate the catheter in crossing the septum (over the guidewire) from the right atrium to the left atrium. In some embodiments, the catheter cap features a second lumen that houses the collapsed cage. In some embodiments, the cage is expanded within the left atrium, thereby expanding the metal loop such that it is RF energized to cut tissue. In some embodiments, the metal loop is placed on the proximal face of the cage such that it makes contact with the septum, or is placed around the curved face of the cage such that when the proximal face is in contact with the septum, a small, defined gap is maintained between the metal loop and tissue. In some embodiments, the RF anode takes the form of a ring electrode and is placed proximal to the septum along the tissue cutter catheter or on other device components that reside within the right atrium. In some embodiments, a distinct tissue stabilizer or tissue stabilizer catheter is not required, as these functions are performed by the cage upon which the metal loop is mounted. In some embodiments, a distinct tissue stabilizer or tissue stabilizer catheter is not required when the tissue cutter is deployed in the left atrium.

Coils and Rolls

In some embodiments, as in FIGS. 6A-6B, the tissue cutter takes the form of a self-expanding coil 603a that expands in diameter and shortens (for example along the proximal—distal axis) upon deployment from the delivery catheter 601 within the right atrium. In some embodiments, the coil 603a self-expands as the delivery catheter 601 is pulled backwards while the tissue cutter catheter 602 is held stationary. In some embodiments, the delivery catheter 601 features a lumen that is slidably engaged with tissue cutter catheter 602. In some embodiments, the tissue cutter catheter 602 features a lumen that provides a passageway for the guidewire 606, the coil is mounted to the tissue cutter catheter 602. In some embodiments, the loop of the coil is dimensioned to correct for its off-center positioning within the tissue cutter catheter 602. In some embodiments, the coil is insulated with insulation 603h with the exception of the distal circular coil, such that a closed electrode loop (RF cathode) 603b is formed upon full coil deployment. In some embodiments, the coil is connected to the RF generator at its proximal end, through conductive wire that runs within the walls of the tissue cutter catheter (not shown). In some embodiments, the coil features two magnets 603c that couple once the coil is sufficiently exposed to form a closed polygon or circular loop. Once deployed, in some embodiments, the electrode 603b is advanced towards the interatrial septum 607 and energized, and the excised tissue plug remains to be speared on the guidewire. In some embodiments, the spring-like shape of the self-expanding coil affords the cutter 603 improved pushability to achieve apposition between the electrode and septum.

In some embodiments, a tissue stabilizer (not shown) will be deployed in the left atrium. In some embodiments, the tissue stabilizer catheter is slidably engaged with the lumen of the tissue cutter catheter 602. In some embodiments, the tissue stabilizer catheter features a lumen that provides a passageway for the guidewire 606. Once the guidewire is positioned in the left atrium, the tissue stabilizer catheter can cross the interatrial septum and be deployed in the left atrium; the tissue stabilizer catheter can be retracted back into the tissue cutter catheter. In some embodiments, the tissue cutter 603 can be deployed in the right atrium; both tissue cutter and tissue stabilizer are brought in contact with the interatrial septum, sandwiching the septum in between.

Figure 8:
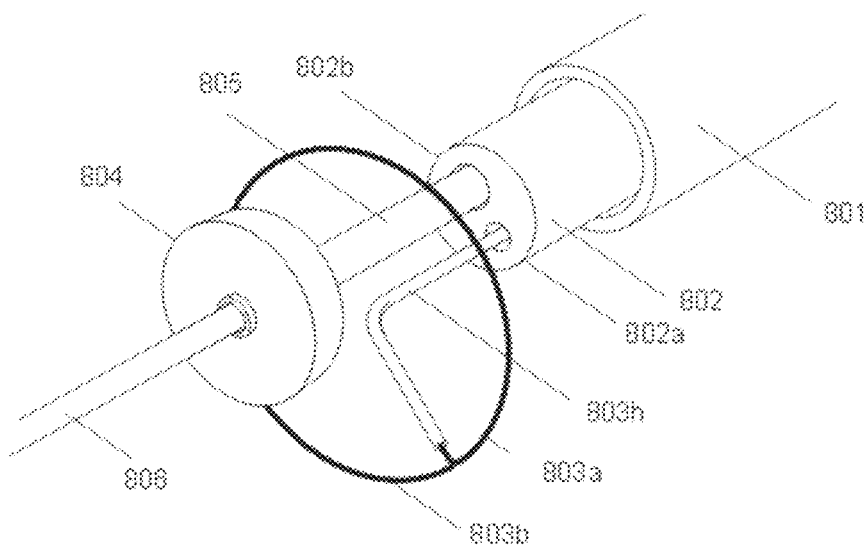
FIG. 8 show an exemplary embodiment of the RF energy-based device assemblies for interatrial anastomosis; in this case, a tissue cutter of the device assemblies.

In some embodiments, as illustrated in FIG. 8, the tissue cutter is a self-expanding coil (shape memory) 803a that initially snakes outwards radially, when it is advanced forward out of the tissue cutter catheter 802 its first lumen 802a, and ultimately forms a closed loop electrode 803b that is brought in contact with the septum. In some embodiments, only the electrode loop is exposed and uninsulated, insulation 803h covers the coil where it is connected to the loop along its length that is slidably engaged within the first lumen of the tissue cutter catheter. In some embodiments, two magnets (not shown) reside at the beginning and end of the exposed, uninsulated coil, which couple to form a closed loop electrode. In some embodiments, the tissue cutter catheter 802 features a double-staged lumen as illustrated in FIG. 8; its second lumen 802b is slidably engaged with the tissue retention element catheter 805 and its first lumen 802a houses the self-expanding coil. In some embodiments, the diameter of the loop is large enough so that it can travel over the tissue retention element, despite its off-center positioning. In some embodiments, the tissue retention element has a smaller diameter than the electrode loop. In some embodiments, the size/diameter of the two lumens of the tissue cutter catheter is similar to each other. In some embodiments, the first lumen is smaller or larger than the second lumen. In some embodiments, the self-expanding coil is dimensioned to correct for its off-center positioning within the tissue cutter catheter 802. In some embodiments, prior to deployment of the coil, any of the previously described tissue retention elements 804 is deployed within the left atrium. In some embodiments, the tissue retention catheter has a lumen that is slidably engaged with the guidewire 806.

In some embodiments, the self-expanding coil is deployed in the right atrium. In some embodiments, the tissue cutter catheter 802 will cross the septum over the guidewire 806 to deploy the tissue retention element in the left atrium. After deploying the tissue retention element, in some embodiments, the tissue cutter catheter is retracted back in the right atrium and the self-expanding coil 803a is deployed by pushing the coil distally. In some embodiments, both tissue retention element and tissue cutter are brought in contact with the septum to achieve apposition, before RF energy is applied. After energization, the tissue plug, in some embodiments, remains speared on the tissue retention catheter 805 and is packed in the delivery catheter 801 after the self-expanding coil is retracted back into the first lumen 802a of the tissue cutter catheter.

In some embodiments, the self-expanding coil is deployed in the left atrium. In some embodiments, the tissue cutter catheter 802 crosses the septum over the guidewire 806 to deploy the tissue retention element in the left atrium. After deploying the tissue retention element, in some embodiments, the self-expanding coil 803a is deployed in the left atrium by pushing the coil distally. In some embodiments, the tissue cutter catheter is retracted back into the right atrium after the loop electrode 803b is deployed. In some embodiments, the electrode loop is brought in contact with the septum to achieve apposition, before RF energy is applied, the tissue retention element remains distal from the electrode loop. In some embodiments, after energization, the tissue plug remains speared on the tissue retention catheter 805 and is packed in the delivery catheter 801 after the self-expanding coil is retracted back into the first lumen 802a of the tissue cutter catheter.

Figure 21:
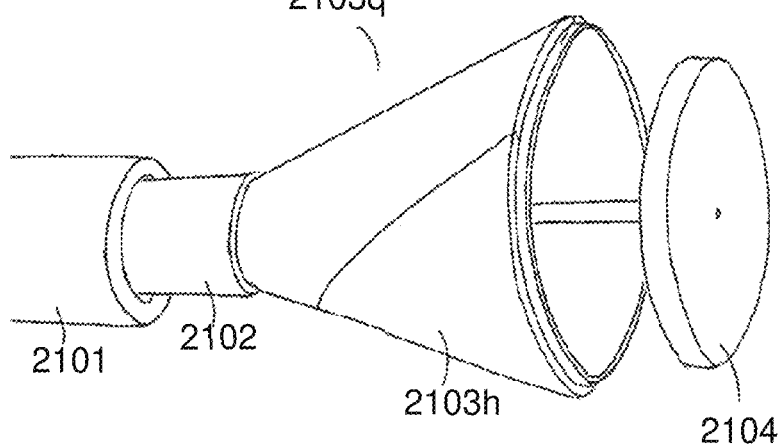
FIG. 21 shows an exemplary embodiment of the RF energy-based device assemblies for interatrial anastomosis; in this case; a tissue cutter of the device assemblies.

In some embodiments, as illustrated in FIG. 21, the tissue cutter takes the form of a rolled sheet 2103q that is fully-insulated 2103h with the exception of at least part of its distal end. In some embodiments, upon deployment from delivery catheter 2101, the sheet unrolls and the distal end expands to assume a larger diameter. In some embodiments, the proximal end of the sheet is attached to a tissue cutter catheter 2102. In some embodiments, the sheet includes a self-expanding (shape memory) metal. In some embodiments, any one of the described tissue retention elements herein 2104 is incorporated to capture and retain excised tissue.

In some embodiments, the tissue cutter takes the form of one or more single-point electrodes connected to one or more self-expanding posts that, when deployed, expand outwards (radially) from the tissue cutter catheter such that a precisely-sized interatrial aperture is created upon RF energization and rotation of the tissue cutter. In some embodiments, the self-expanding post(s) are deployed by pulling the delivery catheter proximally to unsheath the tissue cutter catheter. In some embodiments, the tissue cutter catheter features a central lumen and is slidably engaged with the tissue retention element catheter that crosses the septum to deploy the tissue retention element 2104 within the left atrium.

Figure 22:
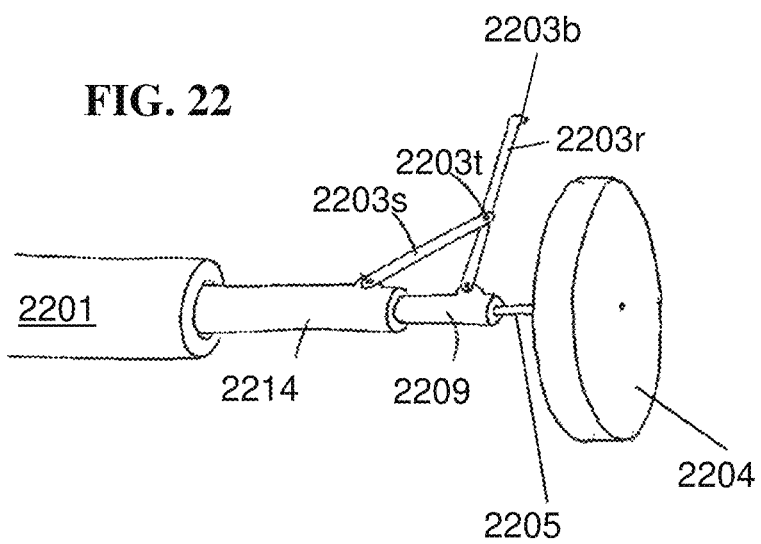
FIG. 22 shows an exemplary embodiment of the RF energy-based device assemblies for interatrial anastomosis; in this case; a tissue cutter of the device assemblies.

In some embodiments, as illustrated in FIG. 22, the tissue cutter takes the form of one or more single-point electrodes 2203b mounted on one or more expansion struts 2203r that is mechanically actuated through an umbrella mechanism, and anchored or supported by an expansion catheter 2209. In some embodiments, two struts—an actuation strut 2203s and the expansion strut—act as a single arm and are connected by a hinge point 2203t; the struts are connected to an actuation catheter 2214 and expansion catheter, respectively, by hinge points. In some embodiments, the actuation catheter is translated in relation to the expansion catheter to rotate the actuation strut the expansion strut outwards (radially) from its hinge point on the expansion catheter. In some embodiments, the expansion strut(s) is self-expanding such that when unsheathed, the strut(s) expands outwards (radially) from the expansion catheter, thereby eliminating the requirement for an actuation catheter and actuation strut(s). In some embodiments, the self-expanding strut(s) is deployed by pulling the delivery catheter 2201 proximally to unsheath the expansion catheter. In some embodiments, the expansion catheter features a central lumen and is slidably engaged with the tissue retention element catheter 2205 that crosses the interatrial septum to deploy the tissue retention element 2204 within the left atrium. Post-expansion, a precisely-sized interatrial aperture is created upon RF energization and rotation of the tissue cutter.

Figure 23A:
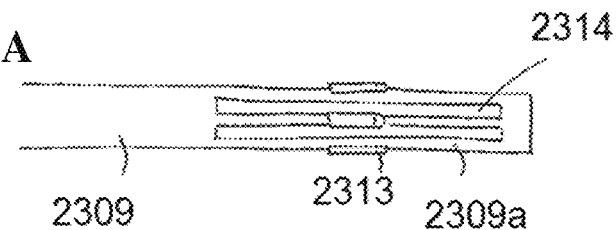
FIGS. 23A-23C show an exemplary embodiment of the RF energy-based device assemblies for interatrial anastomosis; in this case; a tissue cutter of the device assemblies.
Figure 23B:
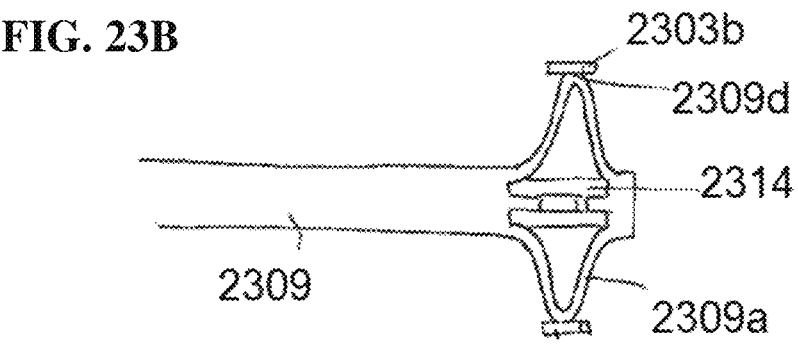
Figure 23C:
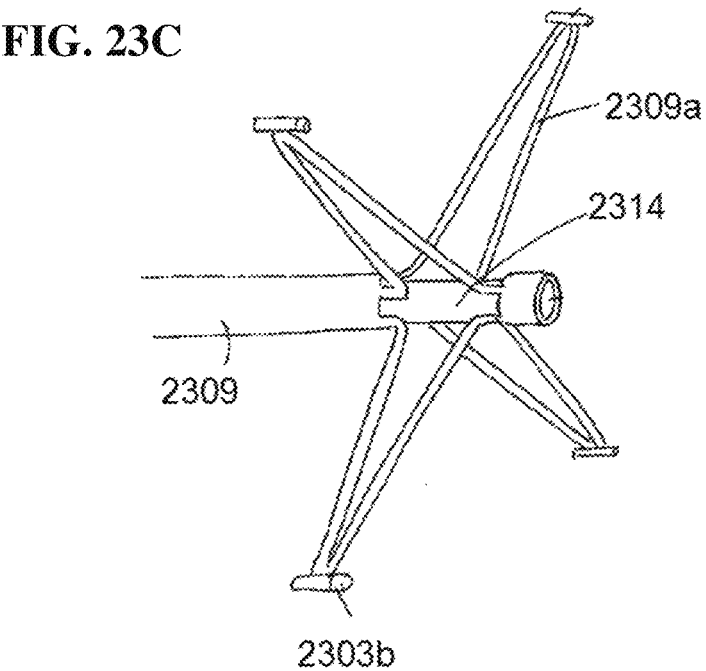
Figure 24:
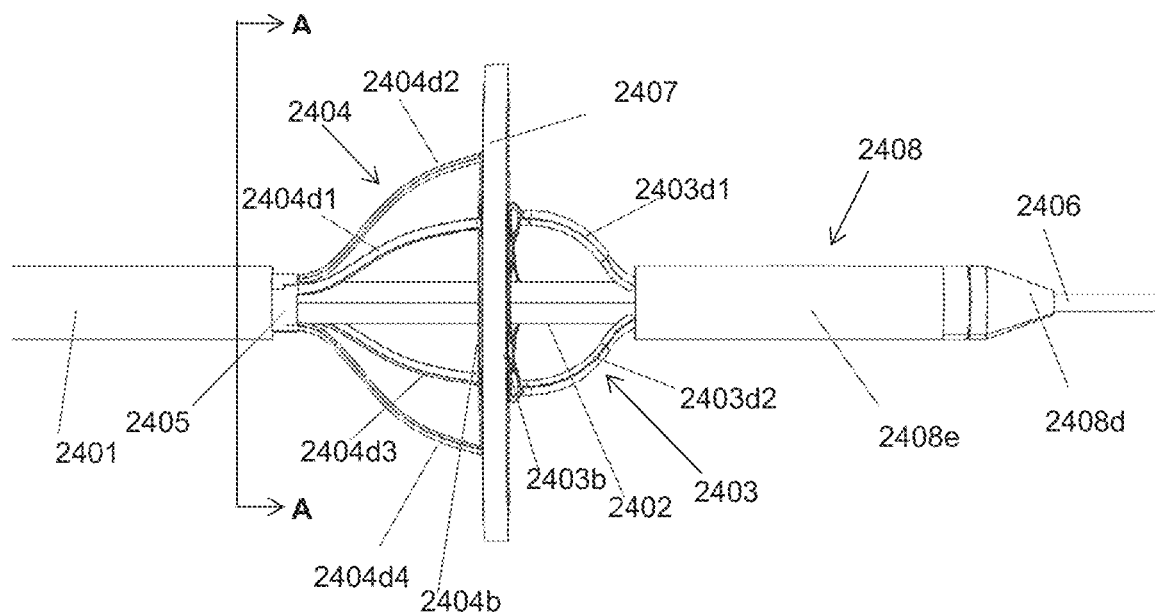
FIGS. 24A-24B shows an exemplary side profile and perspective view of an embodiment of another RF energy-based device assembly for interatrial anastomosis.
FIG. 24C shows an exemplary end view of the embodiment of the RF energy-based device assembly for interatrial anastomosis of FIG. 24A.
Figure 24:
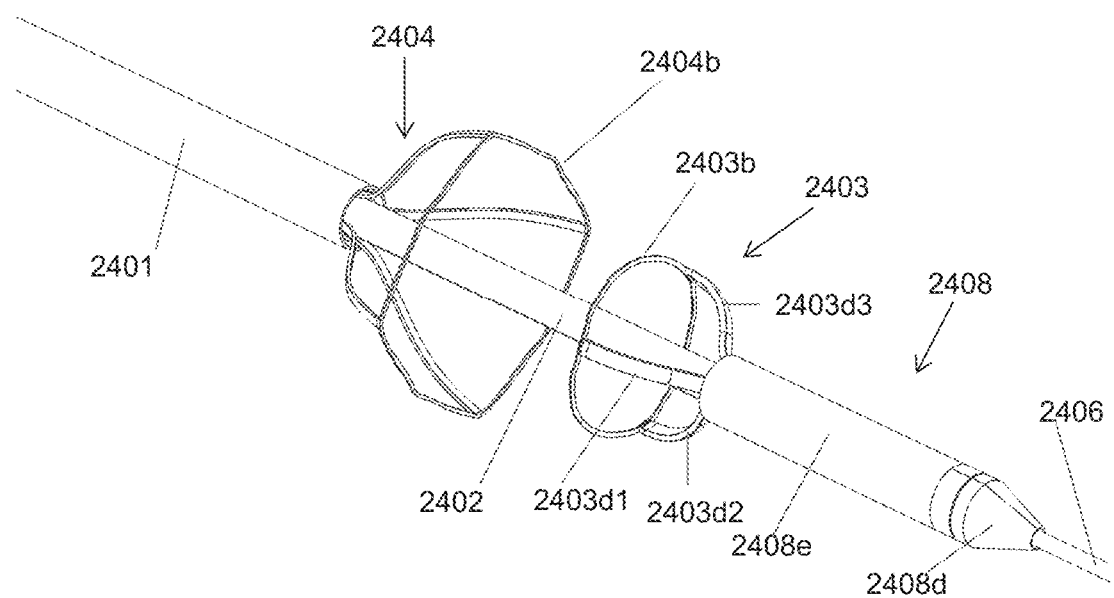

In some embodiments, as illustrated in FIGS. 23A-23C, the tissue cutter 2303 takes the form of one or more struts 2309a that expand to assume a bent configuration at a series of hinge points 2309b at the distal end of an expansion catheter 2309. In some embodiments, one or more electrodes 2303b are fixated or otherwise attached at the hinge point(s) of the strut(s). In some embodiments, the struts are located towards the distal end of the expansion catheter 2309. In some embodiments, the hinge point is located at the midpoint and/or proximal and distal ends of each strut; these hinge points allow the struts to bend outwards radially as the actuation catheter 2314 is translated with respect to the expansion catheter. In some embodiments, post-expansion, the electrodes are brought in contact with the interatrial septum; a precisely-sized interatrial aperture is subsequently created upon RF energization and rotation of the tissue cutter. In some embodiments, the tissue cutter is positioned within the right atrium and a tissue retention element [not shown, positioned within the left atrium] captures and retains the excised tissue. In some embodiments, the tissue cutter is positioned within the left atrium and oriented such that the electrodes face the interatrial septum; post-tissue cutting, the tissue cutter captures and retains the excised tissue, thereby doubling as a tissue retention element. In these embodiments, the struts are comprised of self-expanding metal, non-self-expanding metal, a polymer, or a polymer/metal blend In still further embodiments, referring now to FIGS. 24A-24B, the device assembly includes a delivery catheter 2401, an electrode catheter 2402 to which a partially insulated electrode 2403 having a cathode 2403b is attached, and comprising electrode strut portions 2403d1, d2, d3, a tissue stabilizer catheter 2405 to which an insulated tissue stabilizer 2404 having stabilizing ring 2404b is attached, and comprising tissue stabilizer strut portions 2404d1, d2, d3, d4, and a distal dilator catheter (not shown) to which a distal dilator 2408 comprising a dilator tip 2408d and dilator shaft 2408e are attached. The inner lumen of the distal dilator catheter is slidably engaged with and translatable over any off-the-shelf guidewire 2406 having a size range between 0.014" to 0.035" in diameter. In embodiments such as those shown in FIGS. 24A-28K, the anode of the device is included as a back patch in electrical communication with the RF generator, and thus to the RF cathode of the tissue cutter. Alternatively, the tissue stabilizer may include an anode portion, such for example the ring 2404b, or another portion of the stabilizer or of the device.

Figure 24C:
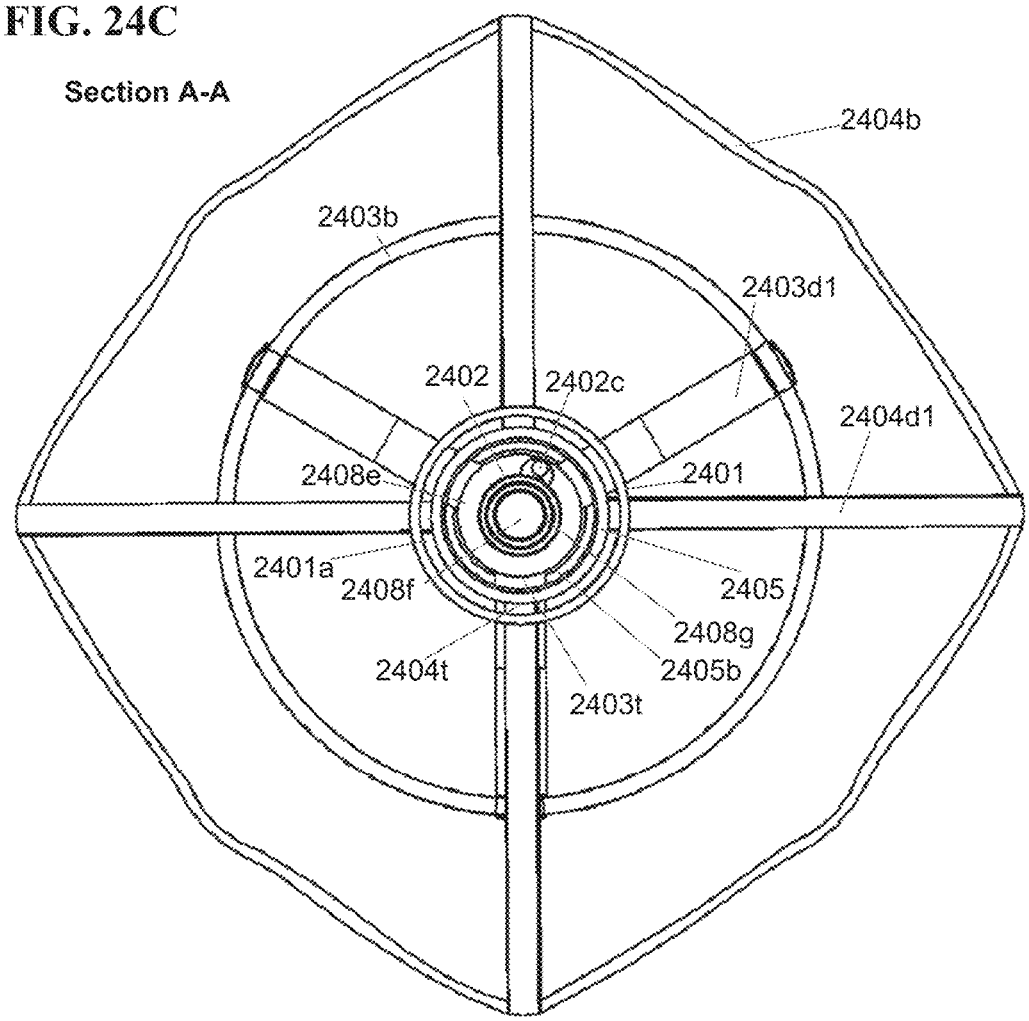

As shown in FIG. 24C, the distal device assembly, viewed in cross section from the proximal end towards the distal end of the device, encompasses: 1) a distal dilator lumen 2408f to permit translation over a guidewire with dilator catheter 2408g, 2) a distal dilator catheter 2408, 3) an electrode catheter 2402, 4) an electrode attachment portion 2403t adjoining the electrode catheter, 5) an embedded insulated power line 2402c, 6) a tissue stabilizer attachment portion 2404t, 7) a distal dilator shaft 2408e, 8) a delivery catheter 2401 within the delivery catheter lumen 2401a, 9) an electrode strut portion 2403d1, 10) an electrode cutting portion 2403b, 11) a tissue stabilizer strut portion 2404d1, 12) a tissue stabilizer stabilizing portion or ring 2404b, and 13) a tissue stabilizer catheter 2405 within the tissue stabilizer catheter lumen 2405b.

In some embodiments, the electrode serves as the RF cathode. A grounding pad placed on the surface of the body serves as the RF anode. In some embodiments, the RF anode is incorporated into the tissue stabilizer at its attachment portion in the form of an uninsulated section or, alternatively, an uninsulated metal-based radiopaque marker ring or band (e.g. platinum, platinum-iridium, gold, nickel-titanium (nitinol), and/or palladium). In some embodiments, the RF anode is alternatively incorporated into the distal tip of the delivery catheter in the form of a metal-based radiopaque marker ring, band, or ink (e.g. platinum, platinum-iridium, gold, nitinol, and/or palladium).

Electrode Assembly
Electrode—Design

Figure 25A:
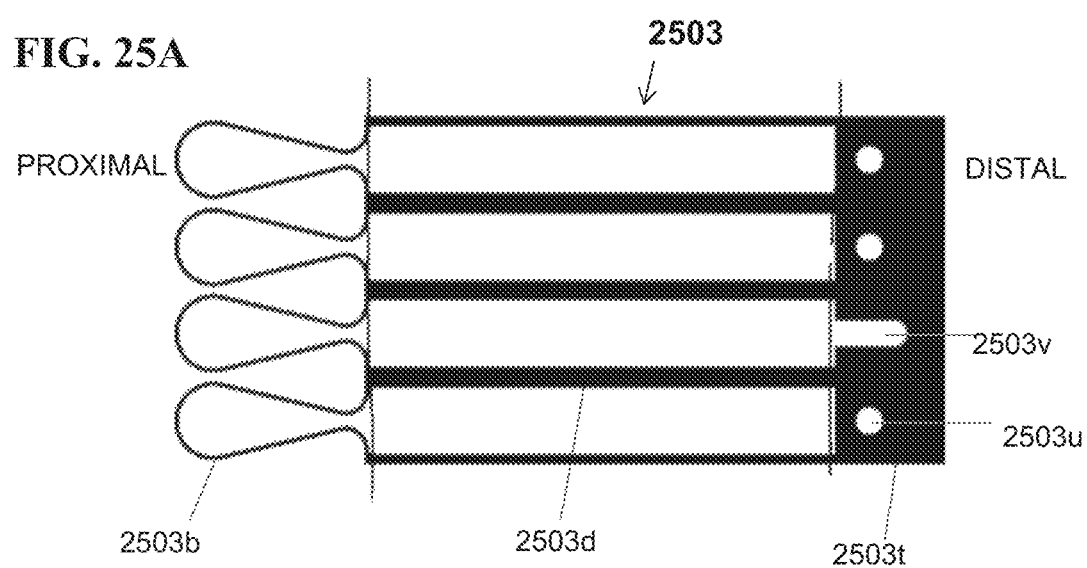
FIG. 25A shows an exemplary embodiment of the RF cautery electrode element of FIG. 24A.
Figure 25B:
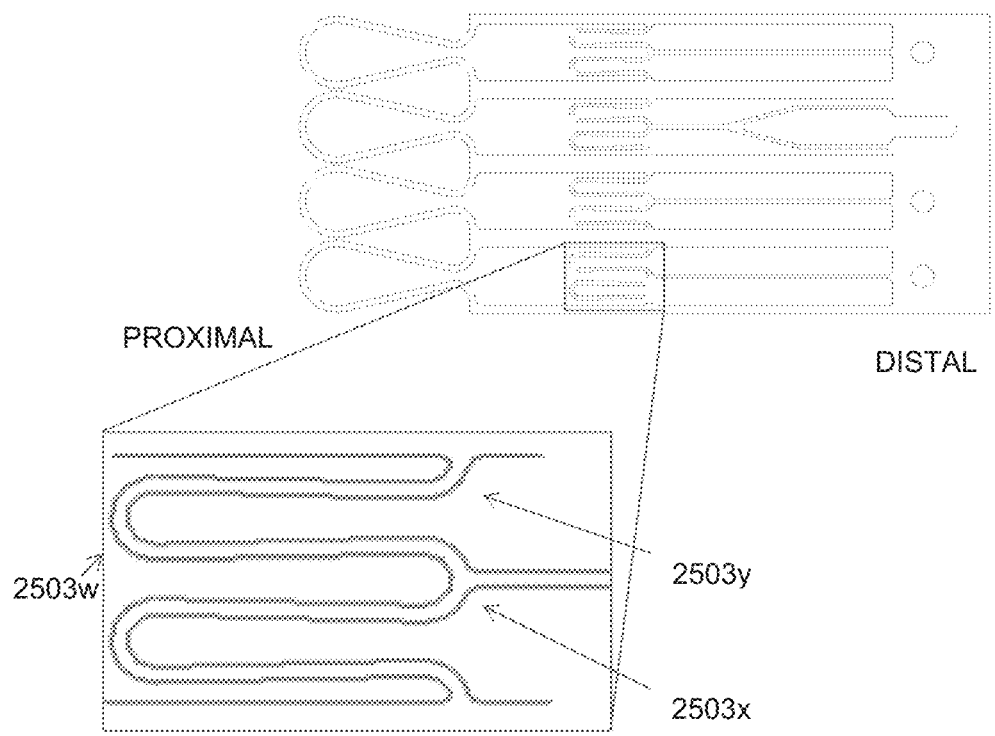
FIG. 25B shows an exemplary embodiment of the RF cautery electrode element of FIG. 24A, wherein the electrode features a secondary cell architecture to increase structural rigidity in its expanded state.
Figure 26:
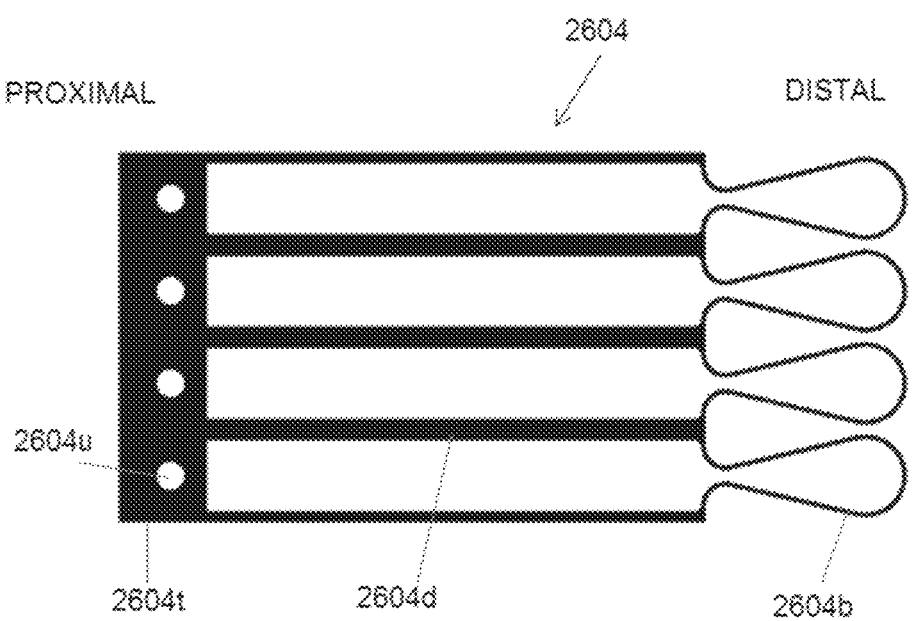
FIG. 26 shows an exemplary embodiment of the tissue stabilizer element of FIG. 24A.
Figure 27A:
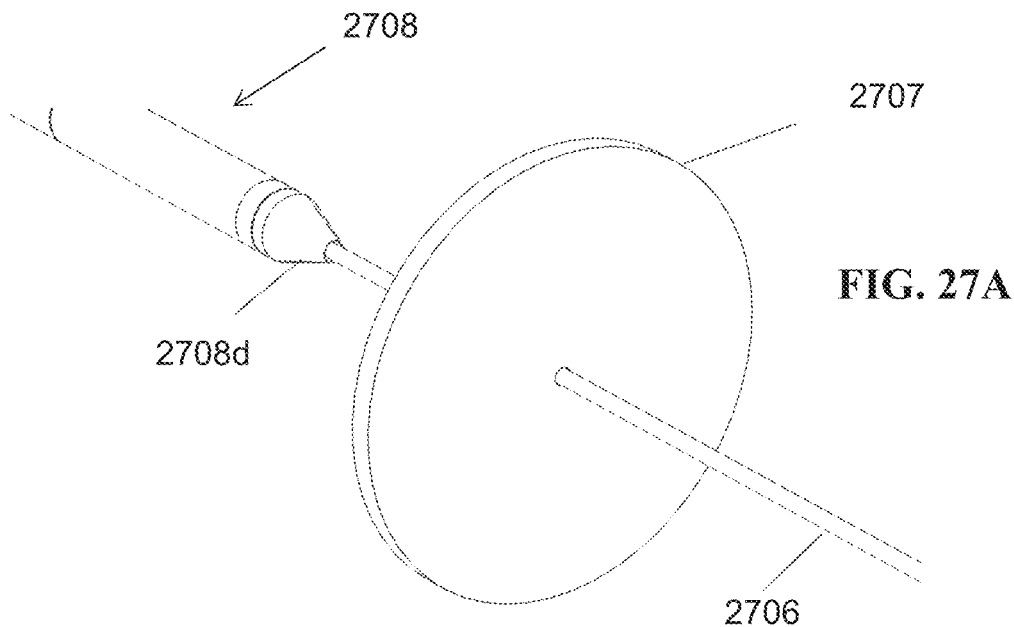
FIGS. 27A-27F show an exemplary embodiment of the RF energy-based device assembly of FIG. 24A and the sequential deployment method and operation for interatrial anastomosis.
Figure 27B:
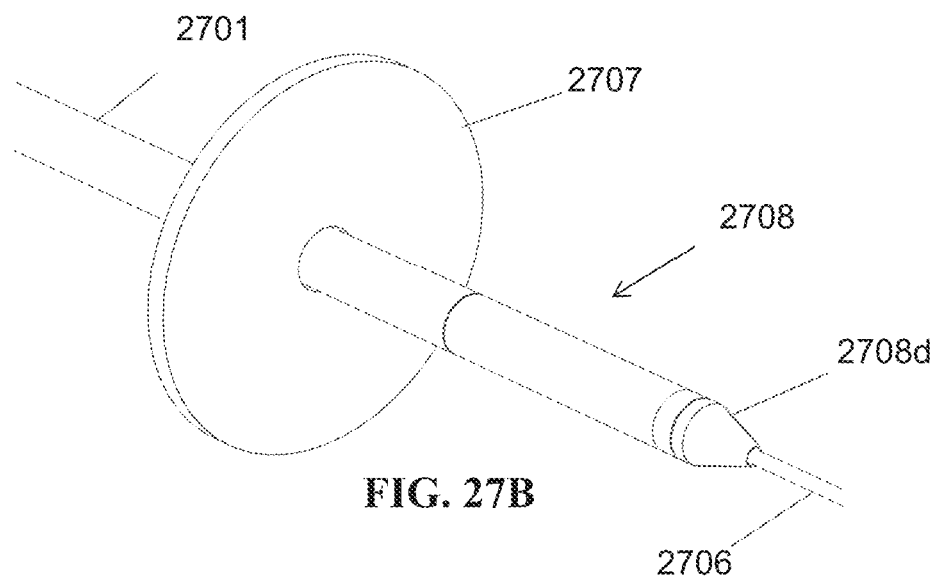
Figure 27C:
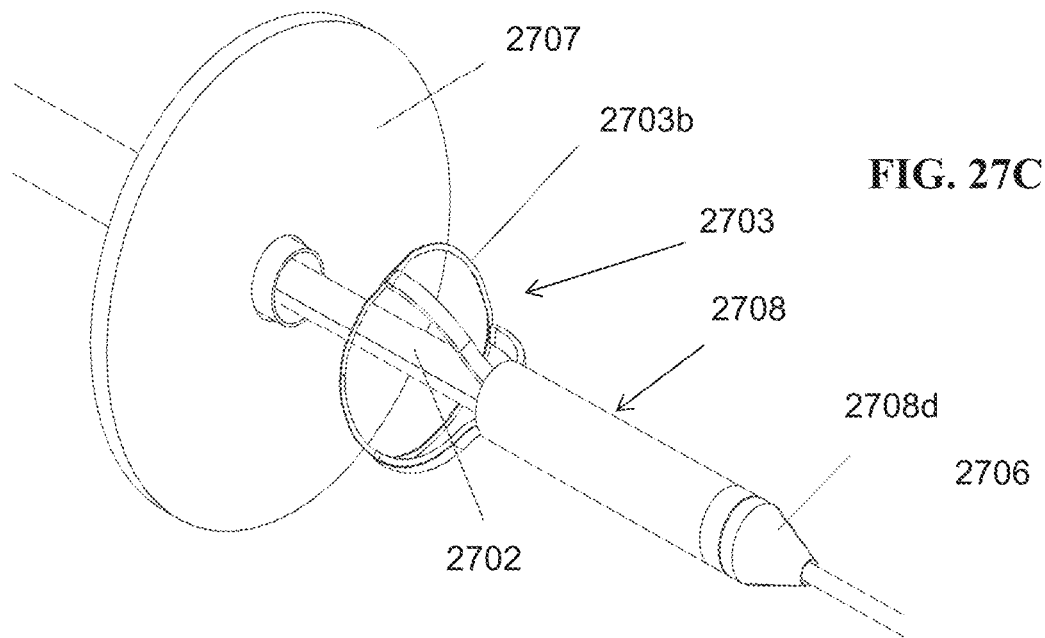
Figure 27D:
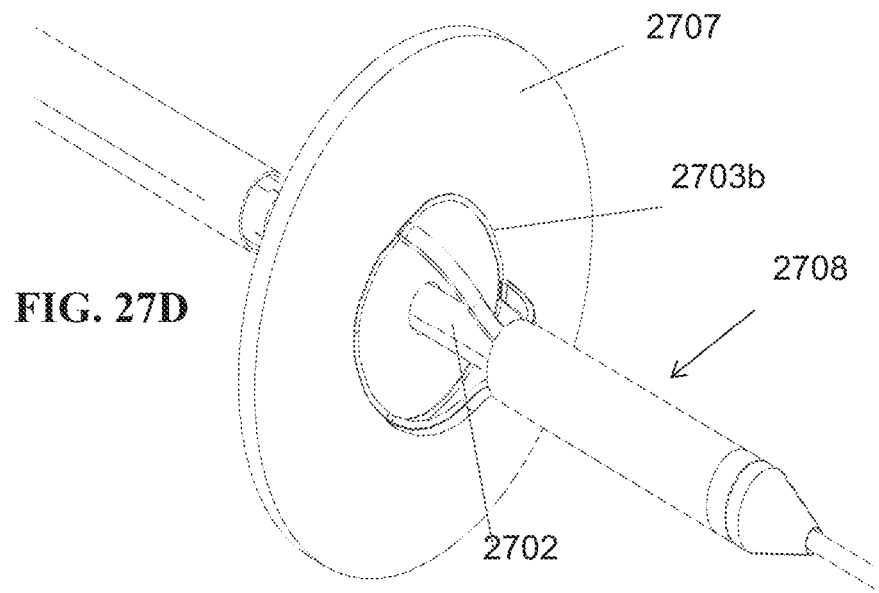
Figure 27E:
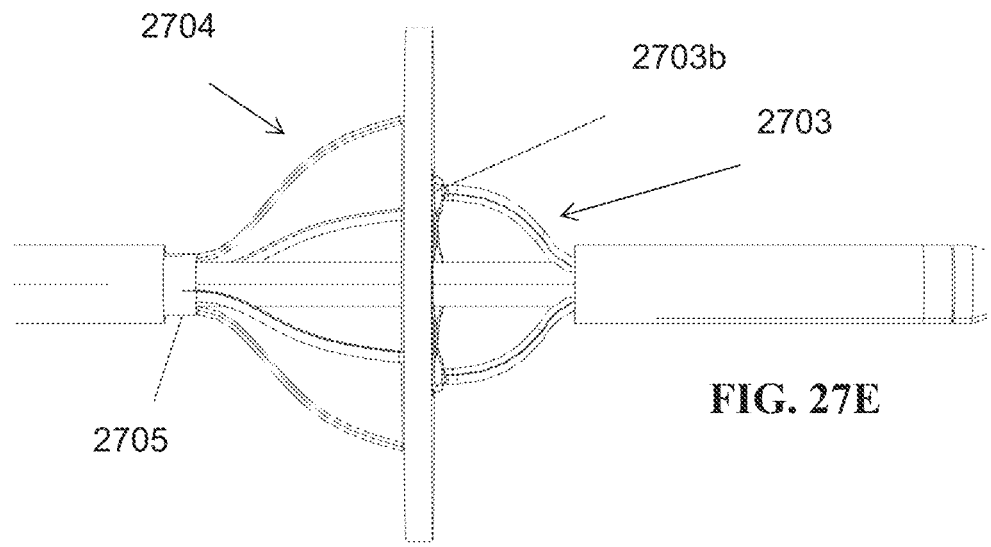
Figure 27F:
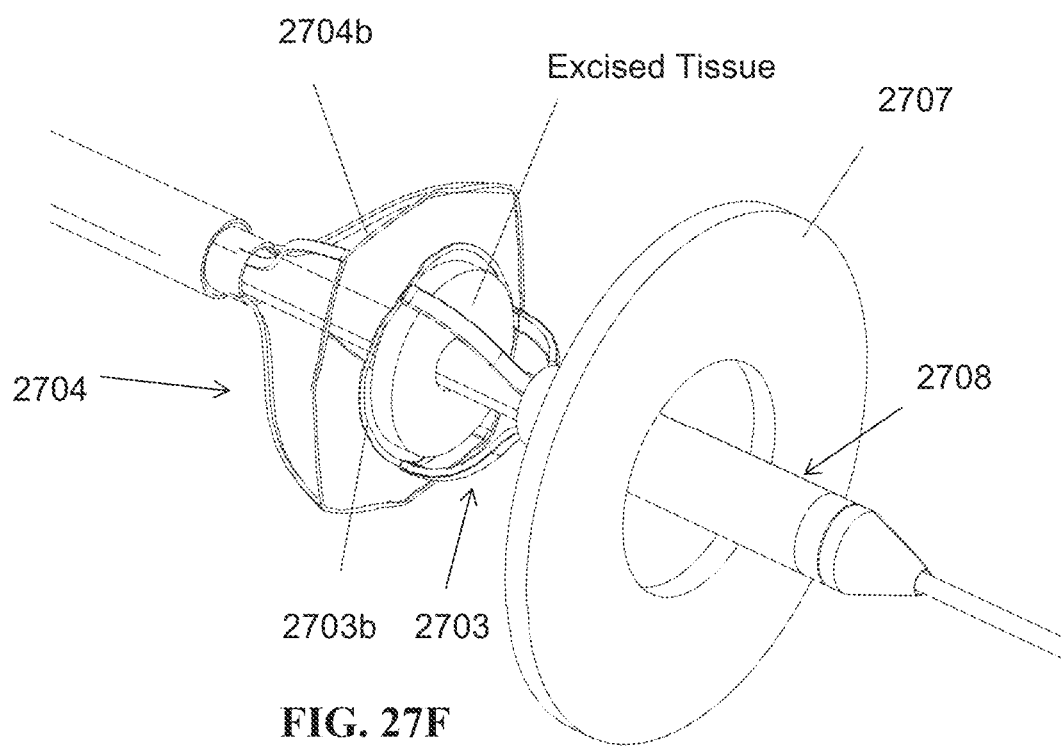
Figure 28A:
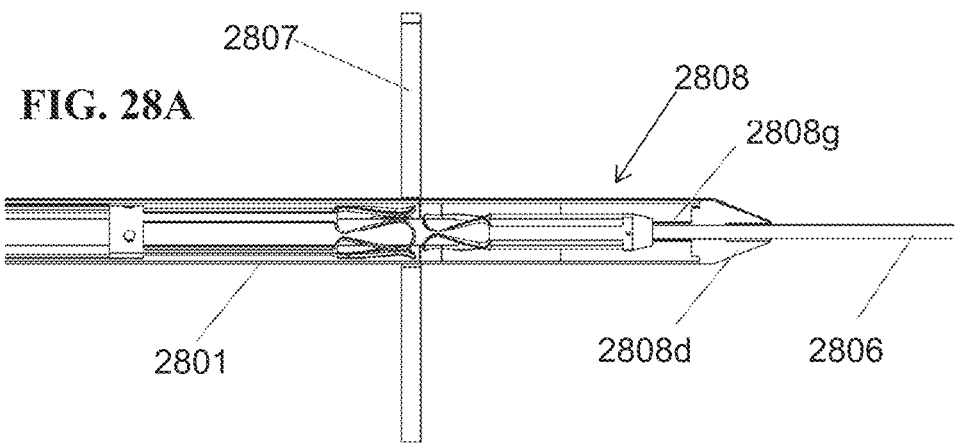
FIGS. 28A-28K show an exemplary embodiment of the RF energy-based device assembly of FIG. 24A and the sequential deployment method, operation method, excised tissue capture and device retraction for interatrial anastomosis.
Figure 28B:
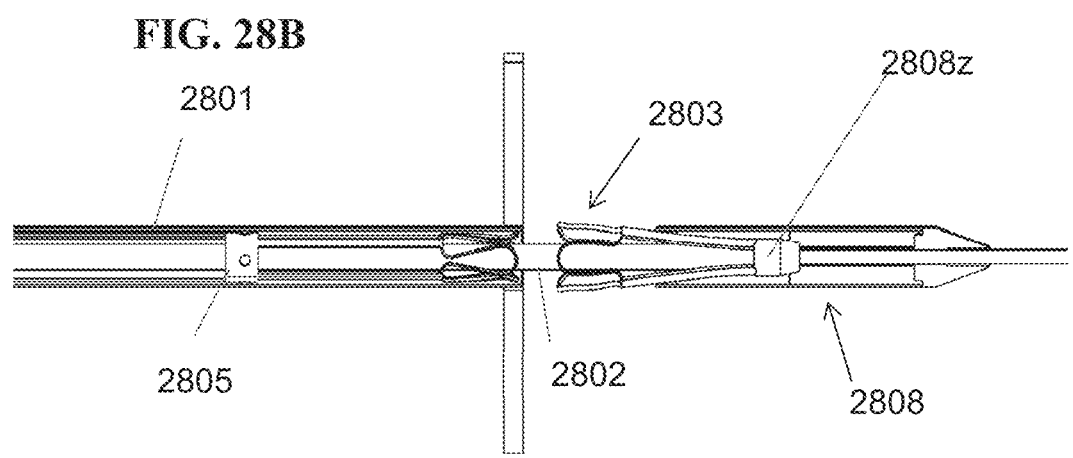
Figure 28C:
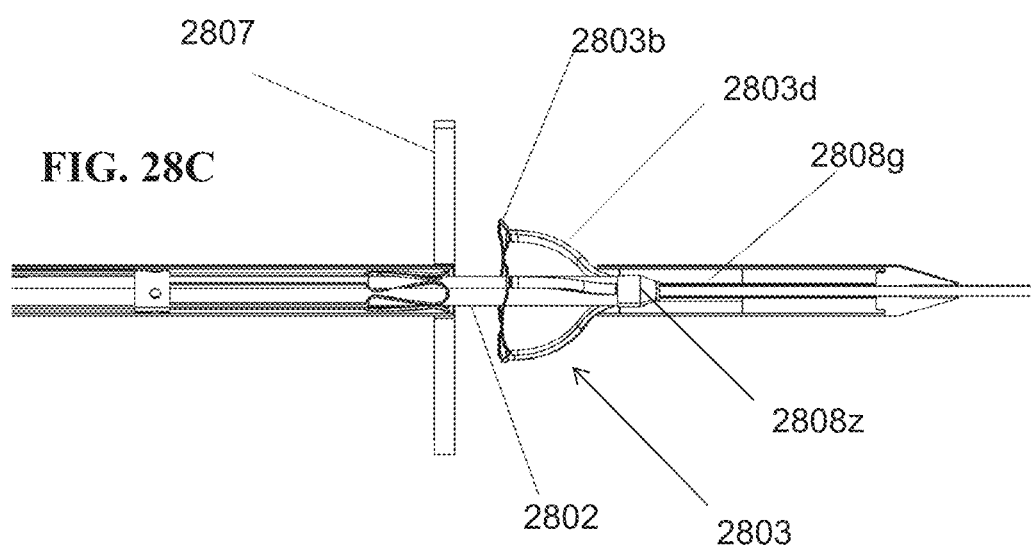
Figure 28D:
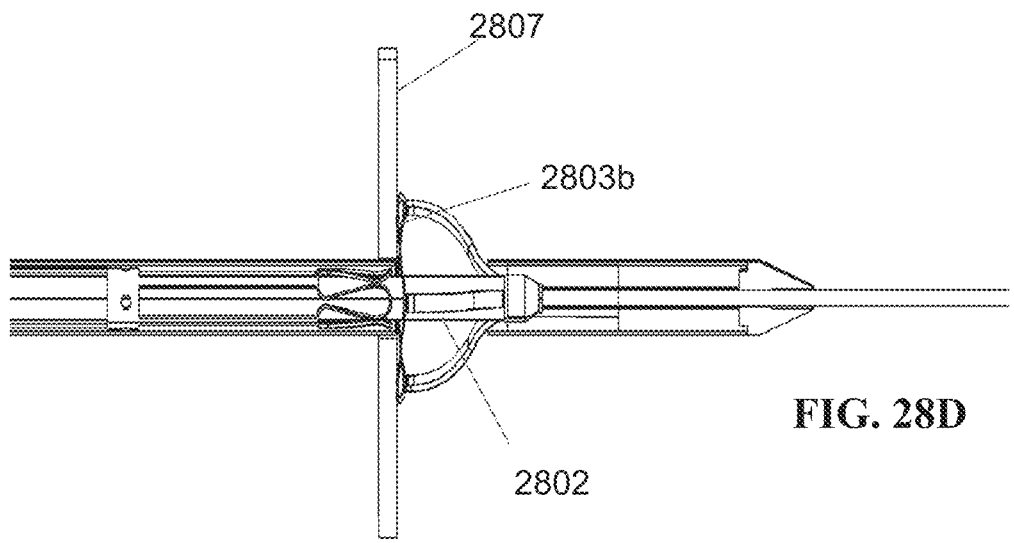
Figure 28E:
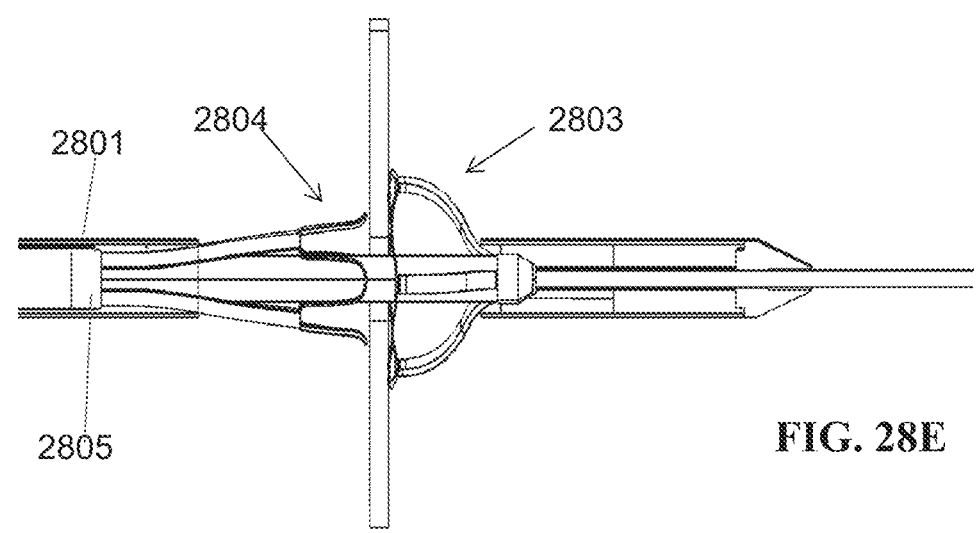
Figure 28F:
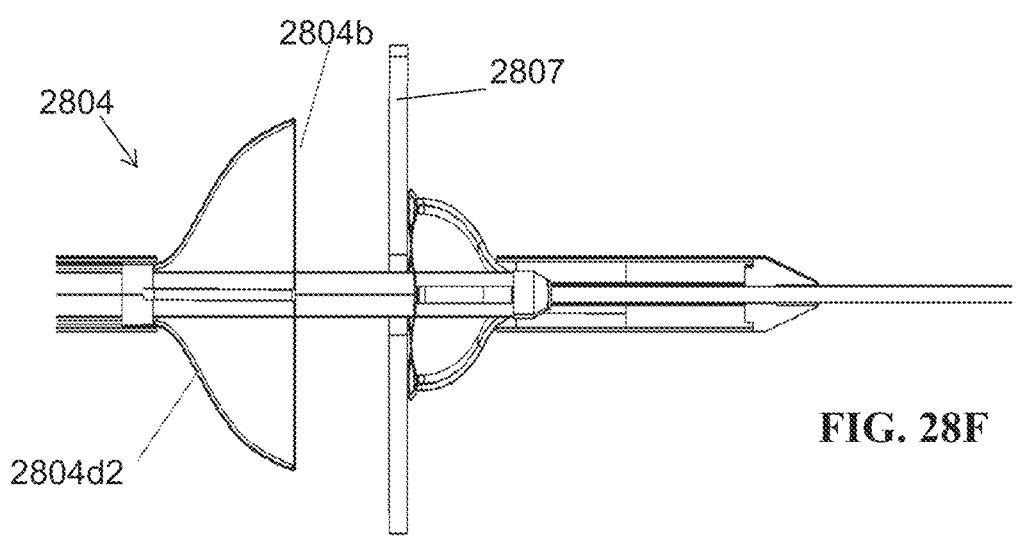
Figure 28G:
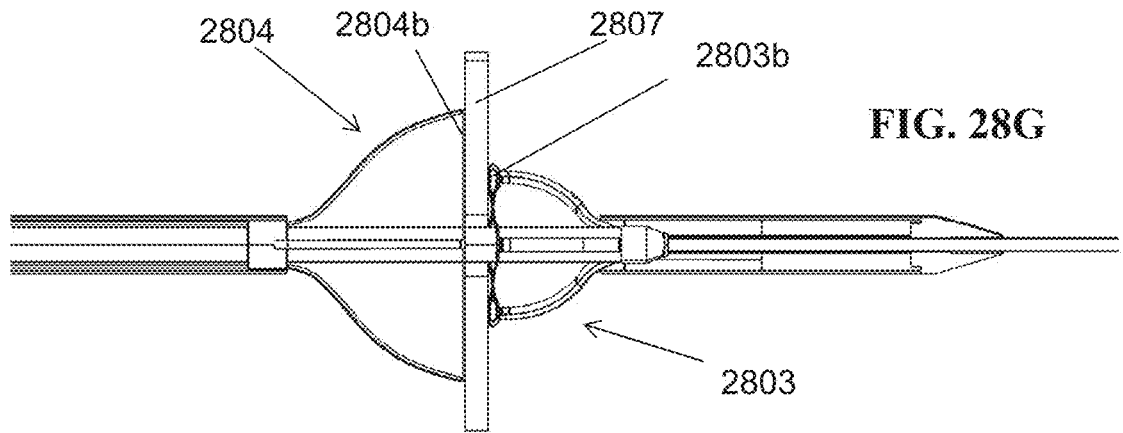
Figure 28H:
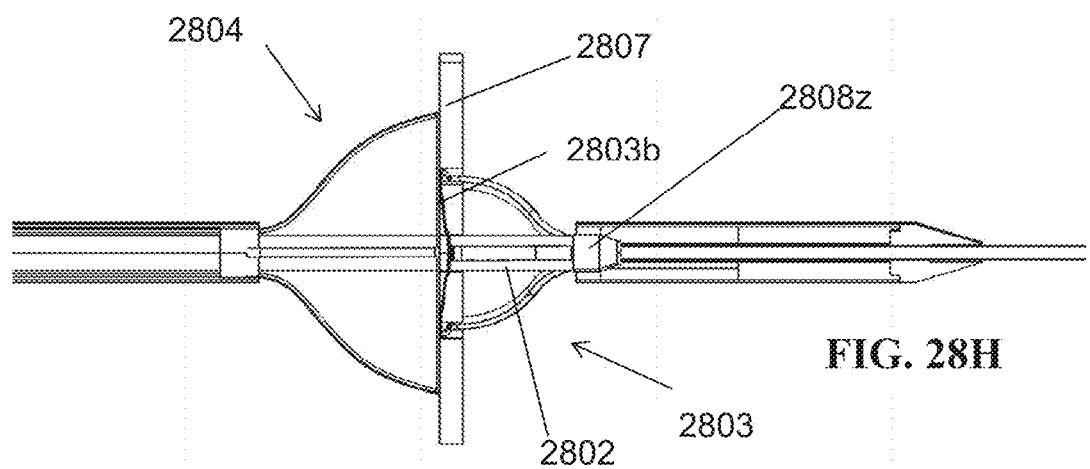
Figure 28I:
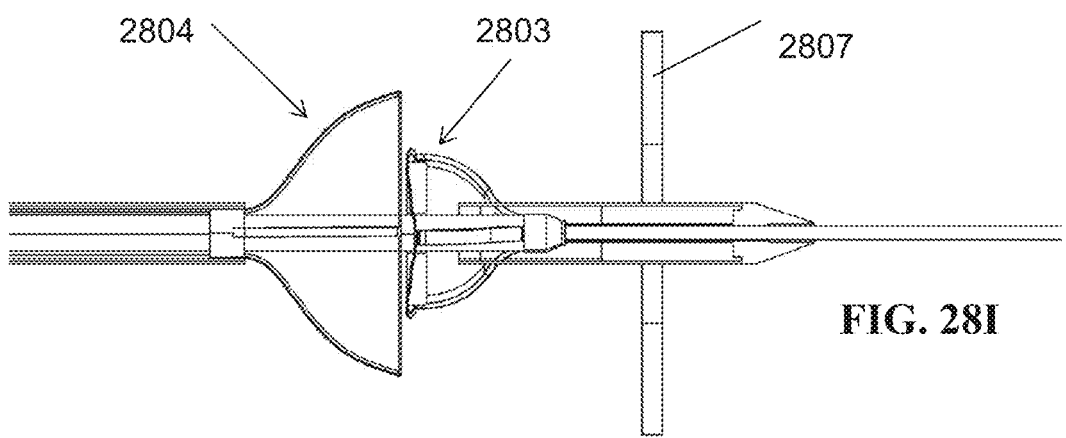
Figure 28J:
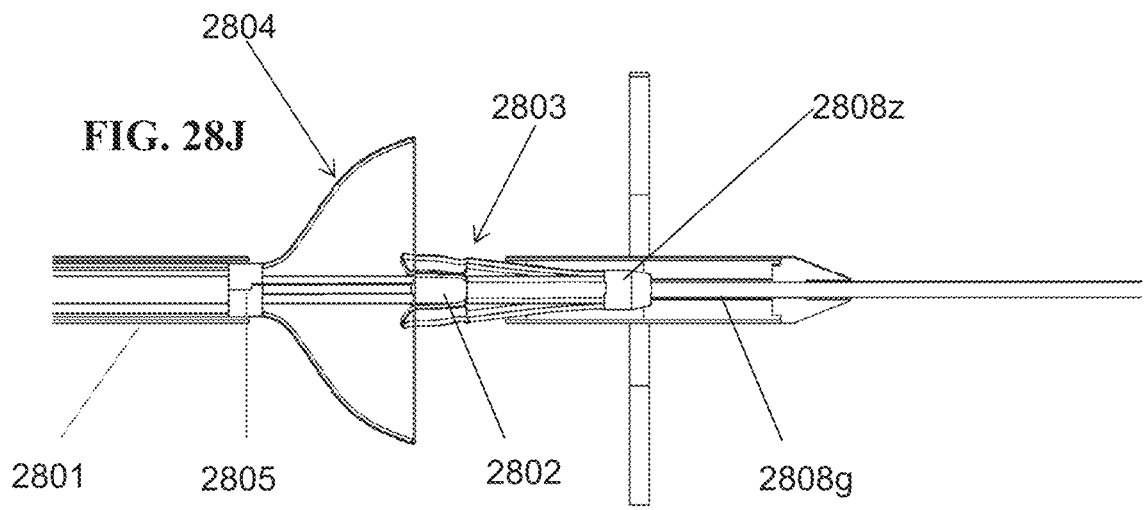
Figure 28K:
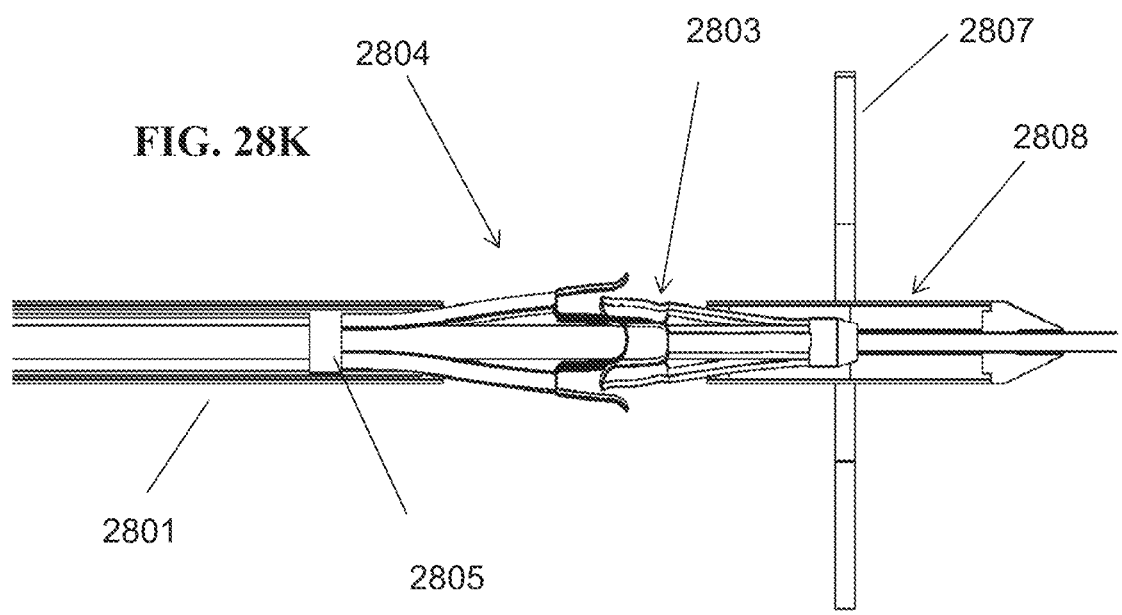

As shown in FIGS. 25A-25B, the electrode 2503 takes the form of a single-part stent comprised of a superelastic shape memory alloy (also known as pseudoelastic behavior materials), such as nickel-titanium/nitinol (alternative alloys include copper-aluminum, copper-aluminum-nickel, copper-aluminum-beryllium, and copper-zinc-aluminum); the electrode is laser cut from tubing having wall thickness between 0.05 mm to 0.30 mm and diameter between 1.0 mm to 1.8 mm, having a specific laser cut pattern (FIG. 25A) and heat set into a specific expanded form (as seen in FIGS. 24A and 24B—re: 2403), which allows for one end of the component to expand to assume a larger dimension between 4.0 mm and 12.0 mm in diameter when unconstrained while the other end maintains the dimension of the tubing from which is was cut to provide a rigid body to which its corresponding catheter (e.g.: 2808z) is attached. The electrode is primarily laser cut from a single tube and typically has no discrete parts; however, the primary cell architecture of the electrode is described in three primary portions (shown in FIG. 25A): (1) a cutting portion 2503*b*, (2) a strut portion 2503*d*, and (3) an attachment portion 2503*t*.

(1) The cutting portion 2503*b* assumes a flat/planar, ring-like configuration when unconstrained, having an expanded dimension between 4.0 mm and 12.0 mm in diameter. The cutting portion is brought into contact with the left atrial face of the septum and generates plasma on its proximal face when energized with radiofrequency (RF) energy. The cutting portion in some embodiments, when energized by the RF energy-conducting struts produces a layer of plasma on its proximal face (face in contact with the septum 2407). The size of the cutting portion being small results in this effect; such sizes i.e. widths and diameters (when multiplied resulting in surface areas), are described below and elsewhere herein. In some embodiments, the cutting portion features a series of attachment points to the struts and strain-relief sections shaped to permit folding and unfolding of the electrode in a predictable manner without plastically yielding, deforming, or breaking. The attachment points of the cutting portion to the struts have variably-decreasing thickness from 0.140 mm to 0.065 mm, rounded intersections, and connect to the struts at a 90° angle to ensure a durable connection between cutting portion and struts to prevent breakage during expansion and collapse of the electrode. The strain-relief sections of the cutting portion are dimensioned to maximize their bend radius (0.02 mm to 1.40 mm) when constrained to minimize flexure during expansion. The cutting portion is between 0.05 mm to 0.25 mm in width to withstand thermal damage during RF energization and cutting, such that the electrode maintains structural integrity to permit collapse post-cutting. The cutting portion in some embodiments alternatively expands to assume a non-circular cross-sectional profile, such as an oval, triangle, square, hexagon, octagon, or other polygon. Nevertheless, the cutting portion in embodiments herein folds radially and circumferentially inwards upon collapsing the electrode, thereby securely grasping the excised tissue within its lumen. The cutting portion in some embodiments is electrically uninsulated or, alternatively, electrically insulated on its distal face only.

(2) The strut portion 2503*d* permits expansion and collapse of the electrode, provides axial and circumferential strength when unconstrained and during RF energization and cutting, and transmits RF energy from the attachment portion to the cutting portion. The struts permit expansion and collapse of the electrode by unconstraining or constraining it through translation and/or rotation of the distal dilator such that the struts collapse the cutting portion as they collapse within the distal dilator. The struts in some embodiments are radially distributed in a plurality between 2-20 mm, each having a width between 0.2 mm to 2.5 mm and a thickness similarly of width between 0.2 mm to 2.5 mm. The struts are rigid to withstand inadvertent collapse of the electrode as it is brought into contact with the left atrial face of the septum and placed under tension during RF energization and cutting. The thicknesses and widths noted herein combined with the material choice, in this example, nitinol, result in sufficient rigidity. Other materials noted herein at the similar dimensions alternatively are sufficiently rigid. The struts are sufficiently flexible to permit intentional collapse by the distal dilator upon intentional translation and/or rotation with respect to the electrode. Similarly, the thicknesses and widths combined with the material choice, in this example, nitinol, result in sufficient flexibility. Other materials noted herein at the similar dimensions alternatively are sufficiently flexible. The struts are connected by one or more expandable, circumferential rings to add rigidity to the electrode in its deployed state. In some embodiments provided herein where the cutter is energy-based, not mechanically based (sharpened blades), the struts are electrically insulated to prevent current leakage such that all RF energy transmitted to the attachment portion is conducted to the cutting portion, with the exception of the proximal edge of the struts, to facilitate plasma generation during RF energization and cutting.

(3) The attachment portion 2503*t* permits coupling of the electrode to its corresponding catheter (e.g.: 2408*g*) and power line (e.g.: 2402*c*), and provides coaxial alignment of the electrode with all other device/system components. The attachment portion in the embodiment in FIG. 25, at least, includes of a recessed cut-out 2503*v* at the distal end of the electrode to facilitate the low-profile attachment of a power line. The power line is electrically coupled to the attachment portion of the electrode by means of soldering, thermal linking with a laser or welder, brazing, or mechanically swaging to provide a durable and consistent electrical connection between the electrode and power line to ensure that all RF energy transmitted through the power line gets conducted to the attachment portion and remainder of the electrode, accordingly. The attachment portion in some embodiments features one or a plurality of cut-outs at its distal end 2503*u*, having an expanded dimension between 0.5 mm to 2.0 mm in diameter to facilitate reflowing of glue or plastic to permit durable attachment of the electrode to its respective catheter. The rigid nature of the attachment portion permits central alignment of the electrode with its corresponding catheter, which effectively aligns the electrode assembly with all other device/system components, thereby ensuring coaxial alignment of the electrode with the tissue stabilizer and delivery catheter. The attachment portion, with power line electrically coupled, is electrically insulated to prevent current leakage, such that all RF energy is transmitted to the cutting portion of the electrode. The power line is comprised of a copper-based wire (e.g. copper, copper clad steel) and may feature a coating of insulation (e.g. polyimide, polyamide-imide). The gauge of the wire comprising the power line is between 40 AWG and 20 AWG.

As shown in FIG. 25B, the electrode may feature a secondary cell architecture to increase structural rigidity in its expanded state. While the electrode is primarily laser cut from a single tube and typically has no discrete parts, this secondary cell architecture is referred to as comprising a connected array of U-shaped portions (2503*w*), Y-shaped portions (2503*x*), and r-shaped portions (2503*y*) interwoven into the primary cell architecture. The r-shaped portions are connected to the struts of the primary cell architecture. The U-shaped portions are not directly connected to the primary cell architecture. The Y-shaped portions, at their base or apex have an arm extending out. A complete array, in some embodiments, include or comprise the sections r, U^n, Y, U^n, and an r connected in series, wherein n is any integer. Additional embodiments may feature (r, U^n, Y, U^n, r)^m completed array sections repeating m times between posts. A Y-portion that is cylindrically aligned with the recessed cut-out 2503*v* at the distal end of the electrode may have an additional U-section at its distal end that bridges the Y-portion to either side of the recessed cut-out 2503*v* at the attachment section. The connected array of U-, Y-, and r-shaped portions may connect to the struts anywhere along its length in order to tune the position of the increased structural rigidity on the electrode. In some embodiments, the secondary cell architecture comprises a plurality of the connected array of U-, Y-, and r-shaped portions down the length of the strut section. Additionally in these embodiments, the Y-shaped portion may connect to another Y-portion or all the way to the attachment portion of the electrode. It is important that in each potential array permutation that the connecting arm section of each Y-portion be the closest part of the array to the electrode attachment section. This design ensures that when collapsing the electrode with the dilator catheter the secondary architectures are closed as well to prevent them from getting caught on the dilator catheter as it translates over the electrode. In an alternative embodiment, the secondary architecture's arrays have no Y-sections, but the arrays are heat set to be angled further radially inward when fully opened to ensure that the secondary arrays fully collapse upon collapse of the tissue stabilizer by the delivery catheter. The secondary cell architecture is intended to increase the parts resistance to deformation from shear force, compression, and tensile forces during actuation without affecting the power requirements to initiate plasma cutting by the electrode as the secondary cell architecture is intended to be fully insulated. The arc length of each of the connected arrays of the secondary cell architecture comprises a length that it does not physically limit the degree to which the electrode may expand and collapse. In some embodiments, the arc length of an array is of varied length, shorter, or longer the closer it is to the electrode cutting section to ensure that the array has an arc length that allows for the stent to fully open while still supplying added stability. Given that the electrode is laser cut from the same starting pattern and its heat setting, the folding and opening of the secondary cell architecture is designed to not impinge on the primary cell architecture in any way as they expand and collapse. The secondary cell architecture improves the mechanics of the electrode and serves as an embolic protection mechanism—the cells effectively decrease the pore size between electrode struts for emboli to flow through and into the systemic vasculature.

Electrode—Electrical Insulation

The electrical insulation applied to the electrode includes a dielectric coating, applied with thickness between 5 μm and 30 μm, and provides a dielectric strength to resist dielectric breakdown during RF energization and cutting. The insulation on the electrode is flexible so as not to compromise electrode flexibility.

The electrical insulation applied to the electrode, in some embodiments, includes or comprises a chemical vapor deposited poly(p-xylylene) polymer such (e.g. parylene C, parylene N), polyurethane (PU), polytetrafluoroethylene (PTFE), expanded PTFE (ePTFE), polyimide (PI), polyester, polyethylene terephthalate (PET), silicone, or a copolymer of any of the aforementioned materials.

Electrode—Catheter

The catheter attached to the electrode 2402 is a dual-lumen catheter. The primary lumen may feature a PTFE liner to facilitate lubricious translation and/or rotation with respect to the distal dilator catheter. Reinforcement of the primary lumen may, in some embodiments, includes or comprises a woven or braided material having a greater stiffness such as nylon or stainless steel to improve catheter pushability and flexibility. The secondary lumen may feature a PI lining with the power line constrained within to electrically isolate the power line from all other device/system components and body. A polymer jacket is, in some embodiments, incorporated to cover both lumens, having a high durometer from 10D to 90D (Shore value) to maximize catheter pushability while maintaining flexibility, and reflowed to impart a circular cross-sectional profile to the electrode catheter.

The electrode is securely attached to the electrode catheter by reflowing the outer polymer jacket, through the cut-outs of the attachment portion of the electrode, to the inner polymer lining, thereby encapsulating and electrically isolating the power line.

The electrode catheter may alternatively be a single lumen catheter.

The electrode catheter features a metal-based radiopaque marker that may take the form of a ring, band, or ink (e.g. platinum, platinum-iridium, gold, nitinol, palladium) at its distal tip permit fluoroscopic visualization.

Electrode—Embolic Protection

The electrode may feature a filter or membrane between or around its struts to capture potential particulate and emboli generated during or post-RF energization and cutting. The filter or membrane may, in some embodiments, includes or comprises dip-coated PU having pore size between 0.001 mm to 1.000 mm to permit the capture of particulate while permitting blood flow across the membrane. The filter or membrane may alternatively, in some embodiments, includes or comprises a woven or braided PET, PTFE, ePTFE, or ePTFE membrane "clamshelled" around the struts having pore size between 0.001 mm to 1.000 mm. The filter or membrane may alternatively comprise a woven or braided nitinol mesh having pore size between 0.001 mm to 1.000 mm.

Tissue Stabilizer Assembly

Tissue Stabilizer—Design

The tissue stabilizer 2604 takes the form of a single-part stent comprised of a superelastic shape memory alloy such as nitinol (alternative alloys include copper-aluminum, copper-aluminum-nickel, copper-aluminum-beryllium, and copper-zinc-aluminum); the tissue stabilizer is laser cut from tubing having wall thickness between 0.05 mm to 0.30 mm and diameter between 1.5 mm to 2.5 mm, having a specific laser cut pattern (FIG. 26) and heat set into a specific expanded form (as seen in FIGS. 24A-24B—re: 2404), which allows for one end of the component to expand to assume a larger dimension between 5.0 mm and 18.0 mm in diameter when unconstrained while the other end maintains the dimension of the tubing from which is was cut to provide a rigid body to which its corresponding catheter is attached.

The tissue stabilizer is laser cut from a single tube and typically has no discrete parts; however, the primary cell architecture of the tissue stabilizer is, in some embodiments, comprised of three portions (shown in FIG. 26): (1) a stabilizing portion or ring 2604b, (2) a strut portion 2604d, and (3) an attachment portion 2604t.

(1) The stabilizing portion or ring 2604b assumes a flat/planar, ring-like configuration when unconstrained, having an expanded dimension between 5.0 mm and 18.0 mm in diameter. The stabilizing portion is brought into contact with the right atrial face of the septum to tension of the septum during RF energization and cutting. The stabilizing portion, in some embodiments, features a series of attachment points to the struts and strain-relief sections shaped to permit folding and unfolding of the tissue stabilizer in a predictable manner without plastically yielding, deforming, or breaking. The attachment points of the stabilizing portion to the struts in the embodiment of FIG. 26, at least, have variably-decreasing thickness from 0.140 mm to 0.065 mm, rounded intersections, and connect to the struts at a 90° angle to ensure a durable connection between stabilizing portion and struts to prevent breakage during expansion and collapse of the tissue stabilizer. The strain-relief sections of the stabilizing portion are dimensioned to maximize their bend radius (0.02 mm to 1.40 mm) when constrained to minimize flexure during expansion. The stabilizing portion is between 0.05 mm to 0.25 mm in width and/or thickness to withstand thermal damage as it tensions the septum during RF energization and cutting by the electrode, such that the tissue stabilizer maintains structural integrity to permit collapse post-cutting. The stabilizing portion alternatively, in some embodiments, expand to assume a non-circular cross-sectional profile, such as an oval, triangle, square, hexagon, octagon, or other polygon. The stabilizing portion folds inwards and circumferentially upon collapsing the tissue stabilizer, thereby securely grasping the electrode and excised tissue within its lumen. The stabilizing portion is fully electrically uninsulated. (2) The strut portion 2604d permits expansion and collapse of the tissue stabilizer, provides axial and circumferential strength when unconstrained and during RF energization and cutting, and encapsulates the electrode and excised tissue post-cutting, thereby prohibiting the electrode from contacting any unintended intracardiac structures. The struts permit expansion and collapse of the tissue stabilizer by unconstraining or constraining it through translation and/or rotation with respect to the delivery catheter such that the struts collapse the stabilizing portion as they collapse within the delivery catheter. The struts are radially distributed in a plurality between 2-20 mm, each having a width between 0.2 mm to 2.5 mm and thickness of between 0.2 mm to 2.5 mm. The struts are sufficiently rigid to withstand inadvertent collapse of the tissue stabilizer as it is brought into contact with the right atrial face of the septum and placed under tension during RF energization and cutting. The thicknesses and widths noted herein combined with the material choice, in this example, nitinol, result in sufficient rigidity. Other materials noted herein at the similar dimensions alternatively are sufficiently rigid. The struts are sufficiently flexible to permit collapse by the delivery catheter upon translation and/or rotation with respect to the tissue stabilizer. The thicknesses and widths noted herein combined with the material choice, in this example, nitinol, result in sufficient flexibility. Other materials noted herein at the similar dimensions alternatively are sufficiently flexible. When the stabilizer is not used as an anode or cathode, the struts are fully electrically insulated to prevent current arcing during RF energization and cutting, and during collapse over the electrode post-cutting. In such embodiments an external patch is attached to the patient, for example to their skin (e.g. their back), and be electrically coupled to the RF generator, as described herein.

(3) The attachment portion 2604t, in some embodiments, permits coaxial alignment of the tissue stabilizer to its corresponding catheter and all other device/system components. The attachment portion, in some embodiments, features one or a plurality of cut-outs at its proximal end 2604u, having an expanded dimension between 0.5 mm to 2.0 mm in diameter, to facilitate reflowing of glue or plastic to permit durable attachment of the tissue stabilizer to its respective catheter. The rigid nature of the attachment portion, in some embodiments, permits central alignment of the tissue stabilizer with its corresponding catheter, which effectively aligns the tissue stabilizer assembly with all other device/system components, thereby ensuring coaxial alignment of the tissue stabilizer with the electrode and delivery catheter. The attachment portion, in some embodiments, is fully electrically insulated to prevent current arcing from the electrode during RF energization and cutting.

The tissue stabilizer, in some embodiments, features a secondary cell architecture to increase structural rigidity in its expanded state. While the tissue stabilizer is generally laser cut from a single tube and typically has no discrete parts, this secondary cell architecture is referred to comprising a connected array of U-, Y-, and r-shaped portions interwoven into the primary cell architecture. The r-shaped portions are connected to the struts of the primary cell architecture. The U-shaped portions are not directly connected to the primary cell architecture. The Y-shaped portions, at their base or apex have an arm extending out. A complete array may, in some embodiments, include or comprise the sections r, U^n, Y, U^n, and an r connected in series wherein n is any integer. Additional embodiments may feature (r, U^n, Y, U^n, r)^m completed array sections repeating m times between posts. The connected array of U-, Y-, and r-shaped portions may connect to the struts anywhere along its length in order to tune the positioning of increased structural rigidity on the tissue stabilizer. In different embodiments, the secondary cell architecture can, in some embodiments, include or comprise of a plurality of the connected array of U-, Y-, and r-shaped portions down the length of the strut section. In these embodiments, the Y-shaped portion may connect to another Y-portion or all the way to the attachment portion of the primary cell architecture. It is important that in each array that the connecting arm section of each Y-portion be the closest part of the array to the tissue stabilizer attachment section. This design ensures that when collapsing the tissue stabilizer with the delivery catheter the secondary architectures are closed as well to prevent them from getting caught on the delivery catheter as it translates over the tissue stabilizer. In an alternative embodiment, the secondary architecture's arrays have no Y-sections, but the arrays are heat set to be angled further radially inward when fully opened to ensure that the secondary arrays fully collapse upon collapse of the tissue stabilizer by the delivery catheter. The secondary cell architecture is intended to increase the resistance to deformation from shear force, compression, and tensile forces during actuation. The arc length of each of the connected arrays of the secondary cell architectures is long enough such that it does not physically limit the degree in which the tissue stabilizer can fully open and close. In some embodiments, the arc length of an array is of varied length, shorter, or longer the closer it is to the tissue stabilizer stabilizing section opening end to ensure that the array has sufficient arc length to allow for the part to fully open while still increasing stability of the part. Since it is all cut from the same starting pattern, the folding and opening of the secondary cell architecture is intended to not impinge on the primary cell architecture in any way as they expand and collapse.

The secondary cell architecture improves the mechanics of the tissue stabilizer and serves as a small emboli protection mechanism—it effectively decreases the pore size between the tissue stabilizer struts for emboli to flow through to and into the systemic vasculature.

The tissue stabilizer, in some embodiments, is used to swallow the excised tissue and electrode by translating the distal end of the device into the delivery catheter, such that the delivery catheter initially collapses the tissue stabilizer, which in turn causes the struts and secondary cell architecture of the tissue stabilizer to apply radial compression on the electrode, which in turn applies radial compression on the excised tissue, thereby permitting all three components to be swallowed by the delivery catheter in a single motion.

In some embodiments, the electrode and tissue stabilizer become 'mated' after cutting by the engagement of a series of hooks or tabs. These hooks or tabs may be incorporated circumferentially along the strut portion of the tissue stabilizer such that when the electrode is translated into the mouth of the tissue stabilizer the hooks/tabs are engaged by the electrode cutting portion. After engagement, the cut tissue is retained within the mated cage. By mechanically coupling the electrode and tissue stabilizer, the entire system may be efficiently made to collapse by advancing of the delivery catheter. In an alternative of this embodiment, the tabs are incorporated into the electrode and mated with a structure on the tissue stabilizer to achieve a similar coupling. In some embodiments, the coupled system is collapsed through translation of the distal dilator catheter.

Tissue Stabilizer—Electrical Insulation

The electrical insulation applied to the tissue stabilizer comprises, in some embodiments, a dielectric coating, applied with thickness between 5 µm and 30 µm, and provides dielectric strength to resist dielectric breakdown during RF energization and cutting. The insulation on the electrode is flexible so as not to compromise electrode flexibility.

The electrical insulation applied to the tissue stabilizer may, in some embodiments, include or comprise a chemical vapor deposited poly(p-xylylene) polymer such (e.g. parylene C, parylene N), PU, PTFE, ePTFE, PI, polyester, PET, silicone, or a copolymer of any of the aforementioned materials.

Tissue Stabilizer—Catheter

The catheter 2405, attached to the tissue stabilizer, in some embodiments, is a single lumen catheter. Its lumen may feature a PTFE liner to facilitate lubricious translation and/or rotation with respect to the electrode catheter. A polyether block amide (PEBA) jacket is incorporated to reinforce the lumen, having a high durometer from 10D to 90D (Shore value) to maximize catheter pushability and flexibility, and reflowed to impart a circular cross-sectional profile to the tissue stabilizer catheter.

The tissue stabilizer, in some embodiments, is securely attached to the tissue stabilizer catheter by reflowing an outer polymer jacket, through the cut-outs of the attachment portion of the tissue stabilizer, to the inner polymer lining of the tissue stabilizer catheter, thereby encapsulating the attachment portion of the tissue stabilizer.

The tissue stabilizer catheter may alternatively take the form of a dual lumen catheter. In such embodiments, the second lumen would house a conductive wire to serve as a return path for RF energy transmitted to an RF anode located on the tissue stabilizer. This conductive wire is comprised of a copper-based wire (e.g. copper, copper clad steel) and may feature a coating of insulation (e.g. PI, polyamide-imide). The gauge of the conductive wire is between 40 AWG and 20 AWG.

The tissue stabilizer catheter, in some embodiments, features a metal-based radiopaque marker that may take the form of a ring, band, or ink (e.g. platinum, platinum-iridium, gold, nitinol, palladium) at its distal tip permit fluoroscopic visualization.

Tissue Stabilizer—Embolic Protection

The tissue stabilizer, in some embodiments, features a filter or membrane between or around its struts to capture potential particulate and emboli generated during or post-RF energization and cutting. The filter or membrane, in some embodiments, include or comprise dip-coated PU having pore size between 0.001 mm to 1.000 mm to permit the capture of particulate while permitting blood flow across the membrane. The filter or membrane may alternatively comprise a woven or braided PET, PTFE, ePTFE, or ePTFE membrane clamshelled around the struts having pore size between 0.001 mm to 1.000 mm. The filter or membrane may alternatively comprise a woven or braided nitinol mesh having pore size between 0.001 mm to 1.000 mm Distal Dilator Assembly Distal Dilator—Design The distal dilator 2408 is comprised of two portions: (1) a dilator shaft 2408e and (2) a dilator tip 2408d.

(1) The dilator shaft 2408e, composed of a polymer having a high durometer (10D to 90D in Shore value) to facilitate collapsing of the electrode. The dilator shaft is, in some embodiments, transparent to permit visualization of the electrode in its collapsed state prior to insertion of the device/system into the body. The dilator shaft is, in some embodiments, composed of PET, PEBA, polyether ether ketone (PEEK), PTFE, silicone, polystyrene (PS), PU, latex, or a copolymer thereof. The dilator shaft may alternatively feature radially-distributed cut-outs towards its proximal end, thereby permitting a transition to a larger size to accommodate for the collapse and packing of the electrode and excised tissue post-cutting. The dilator shaft may alternatively feature an embedded overlapping, incongruous ring composed of an alloy (e.g. nitinol, stainless steel), towards its proximal end, thereby permitting a transition to a larger size to accommodate for the collapse and packing of the electrode and excised tissue post-cutting. The dilator shaft may alternatively feature a length of flexible material at its proximal end (e.g. silicone, polyurethane, or PEBAX), thereby permitting a transition to a larger dimension to permit collapse and packing of the electrode with excised tissue post-cutting. The dilator is, in some embodiments, doped with a radiopaque polymer or feature an embedded radiopaque metal band to permit visualization under fluoroscopic imaging.

(2) The dilator tip 2408d is attached to the dilator shaft and is atraumatic in profile to minimize any inadvertent damage or puncture within the left atrium. The dilator tip, in some embodiments, features a taper between 1° and 45° to facilitate device crossing of the septum to the left atrium. The dilator shaft, in some embodiments, comprises PET, PEBA, PEEK, PTFE, silicone, PS, PU, latex, or a copolymer or a combination thereof. The dilator tip, in some embodiments, features a metal-based radiopaque marker that may take the form of a ring, band, or ink (e.g. platinum, platinum-iridium, gold, nitinol, palladium) at its distal tip permit fluoroscopic visualization. The dilator shaft and tip may alternatively be fabricated as a single part and composed of polypropylene, PET, PEBA, PEEK, PTFE, silicone, PS, PU, latex, barium sulfate (or sulphate), or a copolymer or combination thereof. The distal dilator, in some embodiments, mates with the distal end of the delivery catheter. The distal dilator may alternatively reside and be freely translatable within and beyond the delivery catheter.

Distal Dilator—Catheter

The catheter attached to the distal dilator, in some embodiments, is a single lumen, thin-walled PI catheter. The distal dilator catheter may feature a PTFE liner to facilitate lubricious translation and/or rotation with respect to the guidewire 2406. The distal dilator, in some embodiments, is securely attached to the distal dilator catheter by plastic reflow, overmolding, or glue.

Device/System Delivery Catheter

Delivery Catheter—Design

The delivery catheter 2401, in some embodiments, is a steerable catheter having a single primary lumen and channels for pull wires. Its lumen 2401a features a PTFE liner to facilitate lubricious translation and/or rotation with respect to the tissue stabilizer catheter. A PEBAX jacket and woven or braided stainless steel of high durometer and per inch cross (PIC) count, respectively, is, in some embodiments, used to reinforce the lumen and maximize catheter pushability and flexibility. The delivery catheter may feature a predefined distal curve shape. The delivery catheter is, in some embodiments, steerable or deflectable (uni-directional, bi-directional, 4-way or omnidirectional) via one or more pull wires embedded along the length of its shaft. The delivery catheter may have a bend radius between 45° and 270°. The delivery catheter, in some embodiments, features a metal-based radiopaque marker ring or band (e.g. platinum, platinum-iridium, gold, nitinol, and/or palladium) at its distal tip to permit fluoroscopic visualization. The radiopaque marker ring or band additionally provides a hoop strength that facilitates collapsing of the tissue stabilizer post-cutting. The delivery catheter, in some embodiments, features radiopaque marker ink at its distal tip to permit fluoroscopic visualization.

In embodiments wherein the RF anode is incorporated into the distal tip of the delivery catheter or is incorporated into a portion of the tissue stabilizer such as the stabilizing ring 2404b, the delivery catheter comprises a conductive wire to serve as a return path for RF energy transmitted to the RF anode. This conductive wire is comprised of a copper-based wire (e.g. copper, copper clad steel) and may feature a coating of insulation (e.g. polyimide, polyamide-imide). The gauge of the conductive wire is between 40 AWG and 20 AWG.

Device/System Handle
Component Deployment and Positioning

The handle of the device features an actuator to permit translation and/or rotation of the distal dilator catheter, the electrode catheter, and the tissue stabilizer catheter, in addition to steering of the delivery catheter. The distal dilator catheter and electrode catheter, in some embodiments, translates a maximum distance of 60 mm beyond the distal tip of the delivery catheter. The maximum translatable distance between the distal dilator catheter and electrode catheter, in some embodiments, is limited to the minimum translation required to deploy the electrode. The tissue stabilizer catheter, in some embodiments, translates between approximately 20 mm to 20 mm proximally and distally with respect to the tip of the delivery catheter. The electrode, in some embodiments, is deployed by either translating, and/or rotating, the distal dilator catheter forward, or translating and/or rotating the electrode catheter backwards. Deployment and collapsing of the electrode is, in some embodiments, performed by actuation of a screw/rotation mechanism or a simple translation mechanism. The device handle features, in some embodiments, a safety stop that must be disengaged prior to translating and/or rotating the electrode catheter with respect to the distal dilator catheter; the intention of the stop feature is to prevent undesired or premature deployment of the electrode prior to RF energization and cutting. Alternatively, in some embodiments, the mechanism by which the handle is used to actuate electrode deployment simultaneously couples the power line with the RF generator, thereby inhibiting RF energization of the electrode until the electrode has been deployed.

RF Energization and Cutting

RF energization and cutting is, in some embodiments, completely manual to provide the end user with control over the onset, duration, and cessation of RF energization, in addition to tactile input and feedback regarding translation of the electrode pre- and post-cutting and tensioning of the septum with the tissue stabilizer pre-cutting. In some embodiments, an ERBE 250D RF generator unit is used to deliver 150W of monopolar RF energy in a 1-second pulse. In some embodiments, a grounding pad is placed on an exterior skin surface of the patient.

Automation of one or more procedural steps is, in some embodiments, accomplished by incorporating buttons, knobs, or actuators into the handle.

As RF energy is transmitted, the RF generator is, in some embodiments, configured to measure and detect changes in impedance, temperature, current output, or a fixed time duration to provide the end user with an indication of cut completion.

Device Actuation

In some embodiments, as depicted in FIGS. 27A-F, the device is inserted and advanced over a guidewire 2706, placed through the femoral vein using standard transseptal puncture methods, and delivered to the right atrium. In embodiments wherein the delivery of the catheter is steerable or deflectable, the device is oriented to assume a position that is approximately perpendicular to the septum to minimize tissue distortion, maximize centralization of device positioning with respect to the guidewire, and improve device apposition such that the distal dilator tip 2708d of the distal dilator catheter 2708 is in the appropriate proximity with respect to the interatrial septum 2707 (A). The guidewire 2706, then the distal dilator tip 2708d is advanced across the interatrial septum such that the distal dilator catheter 2708 is positioned within the left atrium (B) with the remaining half of the delivery catheter 2701 residing within the right atrium. The distal dilator catheter 2708 is moved distally with respect to all other device/system components to unsheath and deploy the electrode 2703, support struts, electrode cathode 2703b, and expose the electrode catheter 2702 (C). Alternatively, it is also possible to deploy the electrode 2703 by pulling electrode catheter 2702 proximally with respect to distal dilator catheter 2708. The electrode catheter 2702 is withdrawn proximally such that the cutting portion of the electrode 2703b is brought into contact with the left atrial face of the septum 2707 (D). The tissue stabilizer catheter 2705 is advanced distally with respect to all other device/system components to unsheath and deploy the tissue stabilizer 2704, support struts, and the stabilizing portion/stabilizer ring 2704b within the right atrium; post-deployment, it is further advanced such that the stabilizing portion of the tissue stabilizer is brought into contact with the right atrial face of the septum (opposing the electrode) (E). Alternatively, the delivery lumen is withdrawn proximally relative to the tissue stabilizer 2704 to unsheath and deploy the tissue stabilizer 2704, support struts, and the stabilizing portion/stabilizer ring 2704b within the right atrium; post-deployment, the tissue stabilizer is advanced distally such that the stabilizing portion of the tissue stabilizer is brought into contact with the right atrial face of the septum (opposing the electrode) (E). Thus, it is also possible to deploy tissue stabilizer 2704 by retracting the delivery catheter 2701 with respect to tissue stabilizer catheter 2705. Once the electrode and tissue stabilizer have been positioned on opposing faces of the septum, the electrode is simultaneously energized using an RF generator and withdrawn proximally to excise a coin of tissue from the septum (F).

Post-tissue cutting, the electrode 2703 and tissue stabilizer 2704 remain mated in an overlapped state with the electrode 2703 and the coin of excised tissue nested within the stabilizer contact ring 2704b and struts of the tissue stabilizer 2704, thereby forming a cage within which the excised tissue is enclosed. The cage containing the captured electrode and excised tissue is subsequently withdrawn proximally into the right atrium and collapsed into the delivery catheter 2701 with the excised tissue.

The excised tissue is, in some embodiments, withdrawn towards the attachment portion of the tissue stabilizer within the tissue stabilizer catheter 2705, prior to the collapse of the tissue stabilizer 2704 and electrode 2703.

In an alternative embodiment, the tissue stabilizer 2704 and electrode 2703 do not mate post-cutting; they collapse into the delivery catheter 2701 and distal dilator 2708, respectively.

The excised tissue may remain primarily within the electrode 2703 and is secured first by retracting the distal dilator catheter 2708 with respect to the electrode in order to collapse the electrode around the excised tissue. Subsequently, the delivery catheter 2701 is advanced (or all other device/system components retracted with respect to the delivery catheter) to 'swallow' the collapsed electrode and excised tissue prior to removal of the device from the body.

In some embodiments, as depicted in FIGS. 28A-K, the device is inserted and advanced over a guidewire 2806, and delivered to the right atrium. In embodiments wherein the delivery of the catheter is steerable or deflectable, the device is oriented to assume a position that is approximately perpendicular to the septum to minimize tissue distortion, maximize centralization of device positioning with respect to the guidewire, and improve device apposition such that the distal dilator tip 2808d of the distal dilator catheter 2808 is in the appropriate proximity with respect to the interatrial septum 2807. The guidewire 2806, then the distal dilator tip 2808d and distal dilator 2808, comprising a cutting element fixator 2808z and distal dilator catheter 2808g, is advanced across the interatrial septum such that the distal dilator is positioned within the left atrium (A). The distal dilator catheter 2808 is advanced distally with respect to all other device/system components to unsheath and deploy the electrode 2803 and support struts, and expose the electrode catheter 2802 (B). Alternatively, it is also possible to deploy the electrode 2803 by pulling electrode catheter 2802 proximally with respect to distal dilator catheter 2708. The electrode 2803, support struts (e.g.: 2803d3) and electrode cathode 2803b, fully expand and lock in place (C). The electrode catheter 2802, cutting element fixator 2808z and distal dilator catheter 2808g are withdrawn proximally such that the cutting portion 2803b of the electrode 2803 is brought into contact with the left atrial face of the septum 2807 (D). The tissue stabilizer catheter 2805 is moved proximally with respect to all other device/system components to unsheath and deploy the tissue stabilizer 2804, support struts, and stabilizing portion of the tissue stabilizer within the right atrium (E); The tissue stabilizer 2804, support struts (e.g.: 2804d2), and stabilizing ring 2804b (which may or may not be an anode, depending on the embodiment) of the tissue stabilizer fully expand and lock in place (F). Post-deployment, tissue stabilizer catheter 2805 is advanced (distally) pushing the tissue stabilizer 2804 such that the stabilizing ring 2804b of the tissue stabilizer is brought into contact with the right atrial face of the septum 2807 (opposing the electrode) (G). Alternatively, the delivery lumen is withdrawn proximally relative to the tissue stabilizer 2804 to unsheath and deploy the tissue stabilizer 2704, support struts, and the stabilizing portion/stabilizer ring 2804b within the right atrium; post-deployment, the tissue stabilizer is advanced distally such that the stabilizing portion of the tissue stabilizer is brought into contact with the right atrial face of the septum (opposing the electrode). Thus, it is also possible to deploy tissue stabilizer 2804 by retracting the delivery catheter 2801 with respect to tissue stabilizer catheter 2805. Once the electrode 2803 and tissue stabilizer 2804 have been positioned on opposing faces of the septum 2807, the electrode is simultaneously energized using an RF generator, causing the electrode 2803 to cut a coin of tissue forming an anastomosis in the atrial septum (H). The excised tissue coin, electrode 2803, tissue stabilizer 2804 and a portion of the distal catheter 2808 are retracted proximally into the right atrium (I). The electrode catheter 2802, cutting element fixator 2808z and distal dilator catheter 2808g are advanced distally such that the excised tissue coin is collapsed within the struts of the electrode 2803 (J). The excised tissue coin and end of the electrode 2803 are then captured within a cage formed by the tissue stabilizer struts (e.g.: 2804d1, d2, d3, d4) and the stabilizing portion of the tissue stabilizer (e.g.: 2804b) and withdrawn proximally, first, into tissue stabilizer catheter 2805, then into the delivery catheter 2801, before completely withdrawing the device from the septum and atrium (K). The reassembled device is then ultimately removed from the body.

In an alternative embodiment, the tissue stabilizer 2804 and electrode 2803 do not mate post-cutting; they collapse into the delivery catheter 2801 and distal dilator 2808, respectively.

The excised tissue may remain primarily within the electrode 2803 and is secured first by retracting the distal dilator catheter 2808 with respect to the electrode in order to collapse the electrode around the excised tissue. Subsequently, the delivery catheter 2801 is advanced (or all other device/system components retracted with respect to the delivery catheter) to 'swallow' the collapsed electrode and excised tissue prior to removal of the device from the body.

Balloons

In some embodiments, as illustrated in FIGS. 10A-10D, the tissue cutter includes a flexible metal loop 1003b mounted to a balloon 1003e at or near the distal end of the tissue cutter catheter 1002. In some embodiments, the metal loop is affixed to or near the distal end of a cylindrical balloon that is expanded in the right atrium. In some embodiments, the metal loop is positioned on the distal face of the balloon (FIG. 10A) or alternatively, along the curved face of the balloon (FIG. 10B) such that when the distal face of the balloon is brought in contact with the septum 1007, a small, defined gap is maintained between the tissue and metal loop. In some embodiments, the tissue cutter and tissue cutter catheter 1002 feature a central lumen 1002a to permit translation of the tissue stabilizer catheter 1005 and tissue stabilizer 1004. In some embodiments, the tissue stabilizer catheter 1005 features a central lumen that is slidably engaged with the guidewire 1006. In some embodiments, tissue stabilizer 1004 is a balloon that takes any of the forms described herein. In some embodiments, the RF anode is incorporated into the tissue stabilizer, the tissue stabilizer catheter, or an external electrode (e.g. skin patch). In some embodiments, the tissue cutter catheter 1002 and tissue cutter 1003 are housed within the delivery catheter 1001 prior to deployment of the tissue cutter and following tissue excision.

Figure 11:
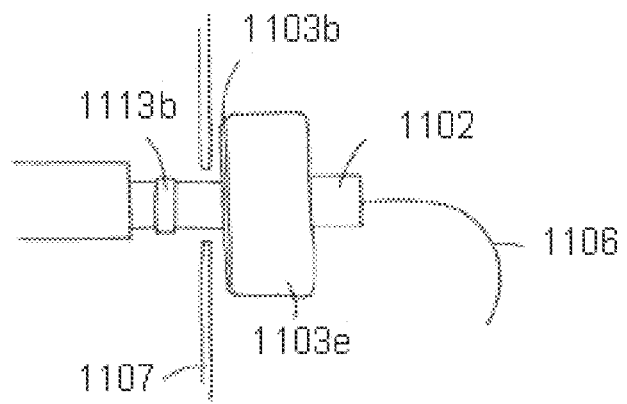
FIG. 11 show an exemplary embodiment of the RF energy-based device assemblies for interatrial anastomosis.

In some embodiments, as illustrated in FIG. 11, the tissue cutter includes a flexible metal loop 1103b on the proximal face of a cylindrical balloon 1103e that is placed across the septum, in the left atrium, over a guidewire 1106. In some embodiments, the balloon is expanded within the left atrium, thereby expanding the metal loop such that it is RF energized to cut tissue. In some embodiments, the metal loop 1103b is placed on the proximal face of the balloon such that it makes contact with the septum 1107, or is placed around the curved face of the cylindrical balloon (not shown) such that when the proximal face is in contact with the septum, a small, defined gap is maintained between the metal loop and tissue. In some embodiments, the RF anode 1113b is placed proximal to the septum along the tissue cutter catheter 1102 or on other device components residing within the right atrium. In some embodiments, a distinct tissue stabilizer or tissue stabilizer catheter is not required, as these functions are performed by the balloon 1103e upon which the metal loop 1103b is mounted. In these embodiments, the balloon is pulled proximally to achieve apposition between the metal loop and septum.

In some embodiments, the metal loop 1103b is expanded to any size with a maximal diameter ranging from about 2 mm to about 15 mm by expanding the balloon 1103e to the corresponding diameter. In some embodiments, the maximal diameter is in a plane transverse to the distal-proximal axis.

In some embodiments, the balloon includes one or more of a cylindrical shape, conical shape, reverse conical shape, at least part of a pyramid shape, a dumbbell shape, a sphere shape, a dome shape, at least part of a football shape, and at least part of a spindle shape.

In some embodiments, multiple flexible metal loops is mounted to or near the proximal or distal face of the balloon (depending on where to deploy the tissue cutter), each having a unique expanded size, ranging from about 2 mm to about 15 mm, upon expansion of the balloon to the corresponding diameter, such that tissue is excised by selectively directing RF energy to the metal loop corresponding to the desired aperture size.

Figure 12A:
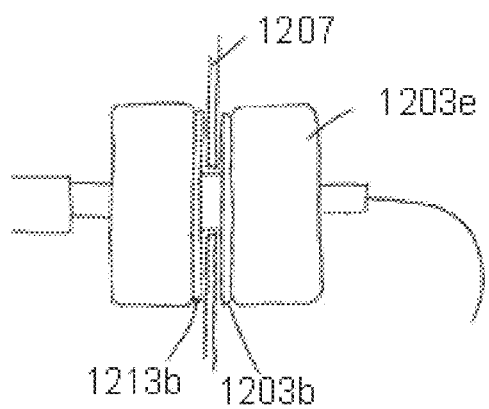
FIGS. 12A-12B show an exemplary embodiment of the RF energy-based device assemblies for interatrial anastomosis.
Figure 12B:
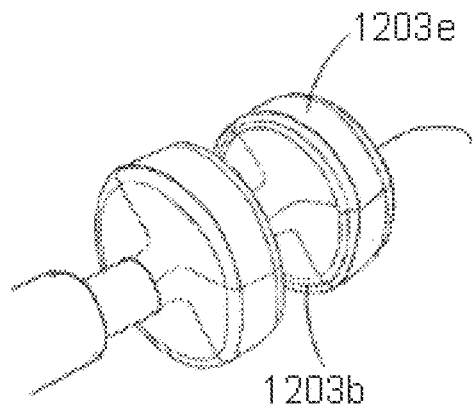

In some embodiments, the RF cathode and anode are mounted on the same balloon, as illustrated in FIGS. 12A-12B. In some embodiments, the balloon 1203e is dumbbell in shape (two cylindrical 'discs' connected by a narrow 'neck') and advanced (deflated, within the delivery catheter) across the septum 1207, such that its neck resides in-plane within the septum. In some embodiments, the RF cathode 1203b and anode 1213b take the form of flexible metal loops mounted on the inner face (septum-facing sides) of each disc; the metal loops make contact with the septum once the balloon is fully inflated. In some embodiments, the metal loops are mounted along the curved face of each disc such that a small, defined gap is maintained between the metal loops and septum. In some embodiments, a distinct tissue stabilizer is not required as the dumbbell-shaped balloon suffices. In some embodiments, a guide catheter is not required, as the inflated dumbbell shape will interact with the septum to ensure that the metal loops are positioned parallel to the septum 1207. In some embodiments, the RF cathode is placed on the proximal disc in the right atrium and the RF anode is placed on the distal disc in the left atrium. In other embodiments, the RF cathode is placed on the distal disc in the left atrium and the RF anode is placed on the proximal disc in the right atrium.

Figure 13A:
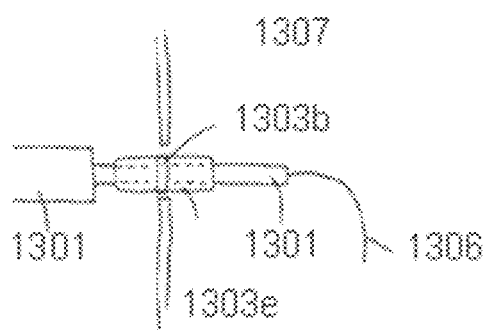
FIGS. 13A-13B show an exemplary embodiment of the RF energy-based device assemblies for interatrial anastomosis.
Figure 13B:
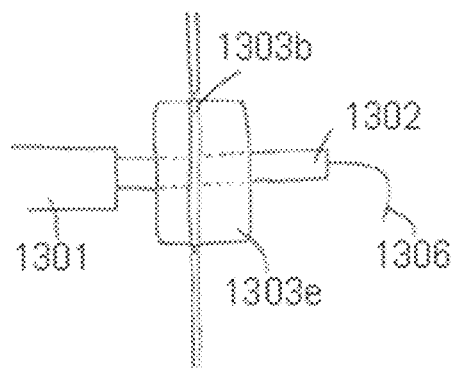

In some embodiments, as illustrated in FIGS. 13A-13B, the tissue cutter is a flexible metal loop 1303b mounted around the midpoint of the curved face of a cylindrical balloon 1303e. In some embodiments, the balloon 1303e is mounted to a tissue cutter catheter 1302 that features a central lumen and is slidably engaged with the guidewire 1306. In some embodiments, the balloon 1303e (FIG. 13A) is advanced (deflated, out of the delivery catheter 1301) across the septum 1307 such that the metal loop 1303b resides in-plane within the septum. In some embodiments, the delivery catheter 1301 is pulled back to unsheath the balloon 1303e; the balloon 1303e is inflated to dilate the tissue and RF energization is applied to the metal loop 1303b, thereby vaporizing the tissue radially to create an aperture. In some embodiments, RF energization is applied to the metal loop 1303b pre-balloon inflation; the RF energization and balloon inflation are alternated stepwise until the balloon 1303e is fully inflated. In some embodiments, RF energization is applied to the metal loop 1303b as the balloon 1303e transitions from its deflated to fully-inflated state. In some embodiments, the outer edges of the balloon 1303e flare out and assume a larger diameter upon expansion to facilitate and secure positioning of the balloon 1303e across and on each side of the septum.

Shape Memory Meshes

In some embodiments, the tissue cutter is a conductive metal loop affixed to a self-expanding (with shape memory material, e.g. Nitinol) cylindrical mesh and mounted to the distal face (septum facing side) of the mesh, or around the curved face of the cylindrical mesh and set back (recessed) from the distal face by a fixed distance in the range of about 0.1 mm to about 10.0 mm. In some embodiments, the mesh features a central lumen that is slidably engaged with the tissue stabilizer catheter. The mesh is mounted to the tissue cutter catheter and housed in a collapsed state within the delivery catheter. In some embodiments, any of the described tissue stabilizer herein can used with these embodiments. In some embodiments, the RF anode is placed on the tissue stabilizer, the tissue stabilizer catheter (in the form of a ring electrode), or external to, but in contact with, the body (e.g. a skin patch electrode).

Following transseptal puncture and delivery/deployment of the tissue stabilizer, in some embodiments, the cylindrical mesh is deployed in the right atrium by pulling the delivery catheter backwards, thereby exposing the metal loop. In some embodiments, the mesh is brought into contact with the septum prior to RF energization.

Figure 9A:
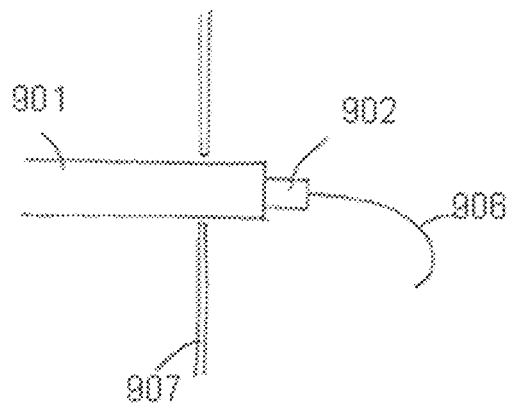
FIGS. 9A-9C show an exemplary embodiment of the RF energy-based device assemblies for interatrial anastomosis; in this case, a tissue cutter of the device assemblies.
Figure 9B:
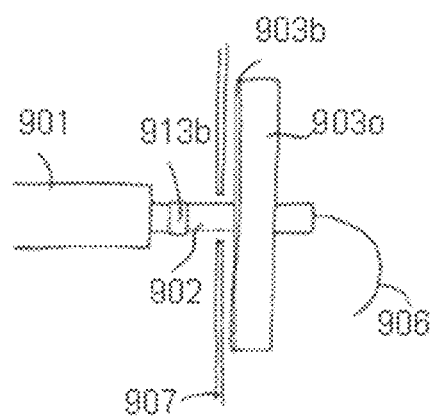
Figure 9C:
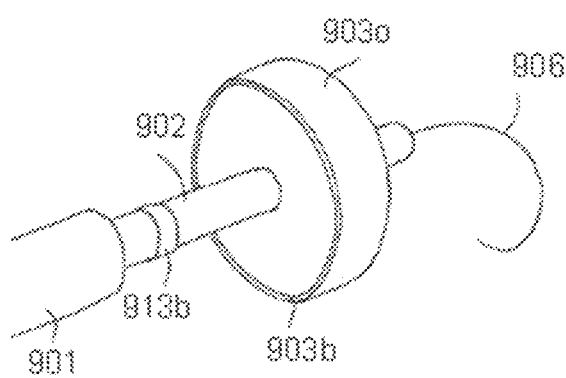
Figure 10A:
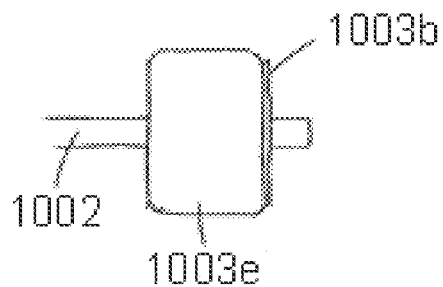
FIGS. 10A-10D show an exemplary embodiment of the RF energy-based device assemblies for interatrial anastomosis.
Figure 10B:
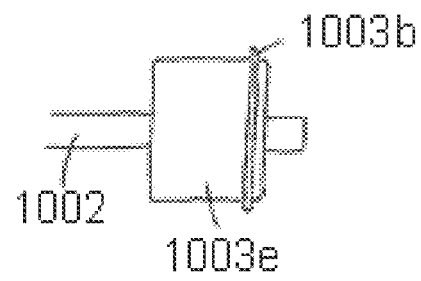
Figure 10C:
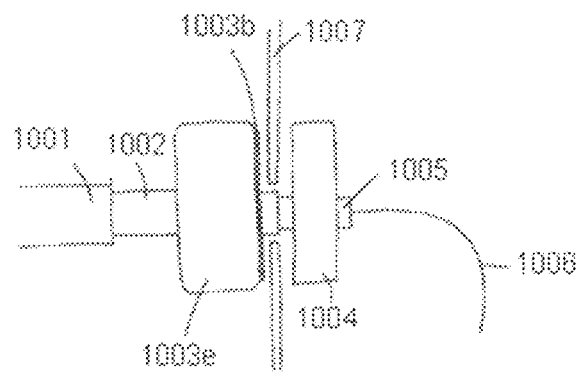
Figure 10D:
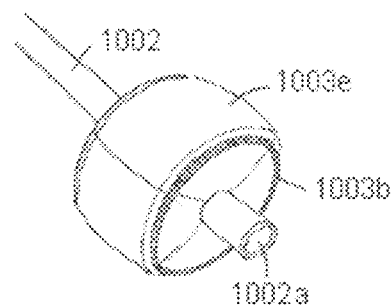

In some embodiments, as illustrated in FIGS. 9A-9C, the tissue cutter is a conductive metal loop 903b affixed to a self-expanding (shape memory) cylindrical mesh 903o and mounted to its proximal face (septum facing side), or around the curved face of the mesh and set back (recessed) from the proximal face by a fixed distance (0.1-10.0 mm). In some embodiments, the mesh is mounted to the tissue cutter catheter 902; both featuring a central lumen that is slidably engaged with the guidewire 906. In some embodiments, the mesh 903o is housed in a collapsed state within the delivery catheter 901. In order to deploy the mesh 903o within the left atrium, the delivery catheter, in some embodiments, crosses the septum 907 to the left atrium. In some embodiments, the delivery catheter 901 is pulled backwards to deploy the mesh 903o. In some embodiments the delivery catheter is further pulled backwards within the right atrium to expose the ring electrode RF anode 913b that resides on the tissue catheter 902. In some embodiments, the tissue cutter catheter 902 is pulled backwards to bring the mesh 903c in contact with the septum 907. Post-tissue cutting, in some embodiments, the excised tissue and mesh 903o are packed within the delivery catheter 901. In some embodiments, the RF anode is external to, but in contact with, the body (e.g. a skin patch electrode).

In some embodiments, the mesh includes one or more of a cylindrical shape, conical shape, reverse conical shape, at least part of a pyramid shape, a dumbbell shape, a sphere shape, a dome shape, at least part of a football shape, and at least part of a spindle shape.

Figure 18A:
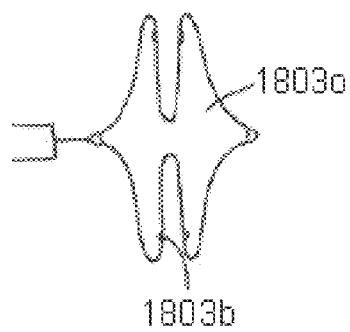
FIGS. 18A-18C show an exemplary embodiment of the RF energy-based device assemblies for interatrial anastomosis; in this case, the tissue cutter of the device assemblies.
Figure 18B:
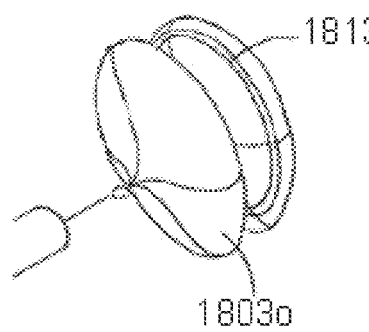
Figure 18C:
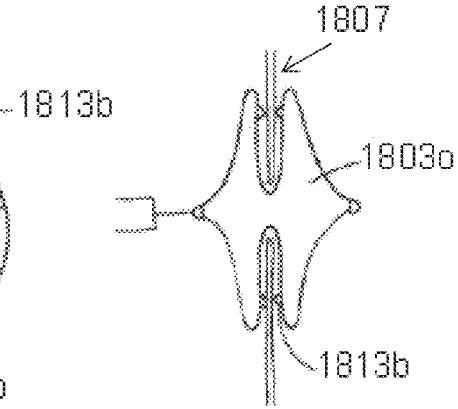

In some embodiments, as illustrated in FIGS. 18A-18C, a self-expanding (shape memory) mesh 1803o in the shape of a dumbbell is composed of two electrically-isolated discs (or bulbs) and attached to the end of a wire. In some embodiments, flexible metal loops are mounted on the inward faces (septum-facing sides) of each mesh disc, or alternatively, on around curved face of each disc (set back with respect to the face contacting the septum). In some embodiments, the discs are constrained within a delivery catheter and unconstrained to permit expansion on either side of the septum 1807. In some embodiments, the metal loops act as the RF cathode 1803*b* and anode 1813*b*. In some embodiments, the RF cathode resides on the distal disc and the RF anode resides on the proximal disc; in other embodiments, the RF cathode resides on the proximal disc and the RF anode resides on the distal disc. In some embodiments, the discs serve to ensure and maintain parallel alignment of the metal loops with septum and firmly engage the tissue during and post-cutting. In some embodiments, the discs are mounted on a catheter (not shown) which features a central lumen is slidably engaged with a guidewire; a separate delivery catheter houses the collapsed discs and its respective catheter. In some embodiments, only one metal loop (RF cathode) is mounted on either disc with the RF anode residing on the delivery catheter or external to, but in contact with, the body (e.g. a skin patch electrode).

In some embodiments, expansion of the self-expanding (shape memory) mesh is actuated by constraining the mesh from a housing catheter through translation, a forward screwing motion, removal of a retaining pin, motor control, or incorporation of magnets.

In some embodiments, the metal loop is expanded to any size with a maximal diameter ranging from about 2 mm to about 15 mm by expanding the mesh to the corresponding diameter. In some embodiments, the maximal diameter is within a plane transverse to the proximal-distal axis.

In some embodiments, multiple flexible, electrically-isolated metal loops are mounted to the proximal or distal face of the self-expanding (shape memory) mesh, each having a unique expanded size, ranging from about 2 mm to about 15 mm, upon expansion of the mesh to the corresponding diameter, such that tissue is excised by selectively directing RF energy to the metal loop corresponding to the desired aperture size.

In some embodiments, the self-expanding (shape memory) mesh is fully insulated with the exception of a small, exposed circular surface area. In some embodiments, this exposed circular surface area acts as an electrical conductor and performs the functions of the metal loop by serving as a source or return for RF current. In some embodiments, a tissue cutter with partly conductive self-expanding mesh(es) does not require any metal loop(s).

Guillotines

Figure 14A:
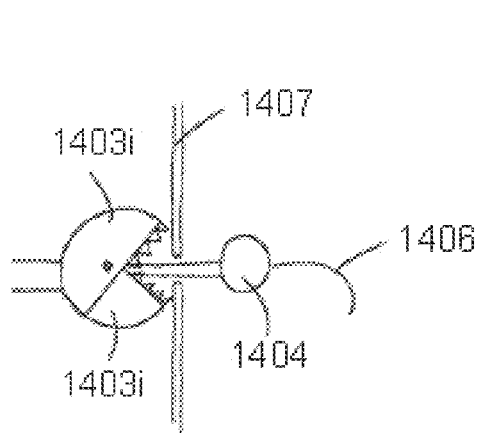
FIGS. 14A-14B show an exemplary embodiment of the RF energy-based device assemblies for interatrial anastomosis.
Figure 14B:
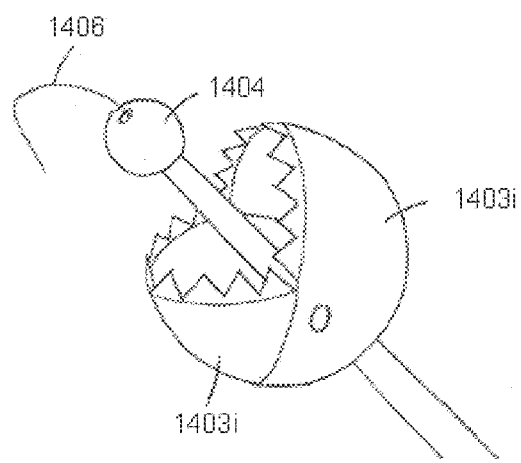

In some embodiments, as illustrated in FIGS. 14A-14B, the tissue cutter takes the form of mechanically-actuated jaws that open and close through the actuation of a wire pulley system that closes the jaws 1403*i* when pulled taut and opens when released (no pulling). In this embodiment, each jaw is connected to the RF generator through conductive wire, with one jaw acting as the RF cathode and the other jaw as the RF anode. In this embodiment, the jaws 1403*i* are advanced over a guidewire 1406 to the septum 1407, and actuated to bite and coapt with the septum; RF energization is subsequently applied to create an aperture. In some embodiments, the excised tissue is retained within the jaws 1403*i* of the tissue cutter, which is retrieved by delivery catheter, therefore acting as a tissue retention element. In some embodiments, a secondary tissue stabilizer 1404 is introduced within the left atrium to tent the tissue into the mouth of the jaws 1403*i*.

In some embodiments, as illustrated in FIGS. 15A-15D, the RF cathode 1503*b* and anode 1513*b* take the form of semicircular conductive metal strips that line the distal edge of the delivery catheter 1501 or tissue cutter catheter 1502 such that as the tissue stabilizer 1504 pulls the septum 1507 into the delivery catheter 1501 or tissue cutter catheter 1502, the metal strips 1503*b* and 1513*b* are RF energized, and an aperture is created within the septum 1507; the excised tissue is packed into the delivery catheter 1501 or tissue cutter catheter 1502 by the tissue stabilizer 1504. In some embodiments, the metal strips are set back (recessed) from the distal edge of the delivery catheter 1501 or tissue cutter catheter 1502 to ensure a small, defined gap between the metal strips 1503*b* and 1513*b* and the septum 1507. In some embodiments, the tissue stabilizer 1504 expands to a diameter that is less than the inner diameter of the delivery catheter 1501 or tissue cutter catheter 1502.

In some embodiments, as illustrated in FIGS. 16A-16B, the tissue cutter takes the form of a non-expandable ring 1603*b* along the edge of the delivery catheter 1601 or tissue cutter catheter 1602. In some embodiments, the tissue stabilizer 1604 acts as the RF anode. In some embodiments, once the tissue stabilizer 1604 is positioned within the left atrium, the tissue stabilizer is pulled proximally into the delivery catheter 1601 or tissue cutter catheter 1602; RF energy is then applied to create aperture within the septum 1607.

Additional Cutting Element Expansion Mechanisms

Figure 17A:
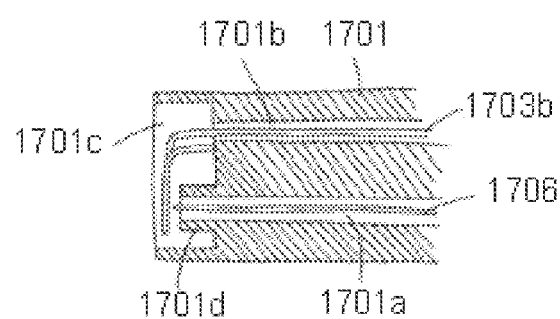
FIGS. 17A-17D show an exemplary embodiment of the RF energy-based device assemblies for interatrial anastomosis.
Figure 17C:
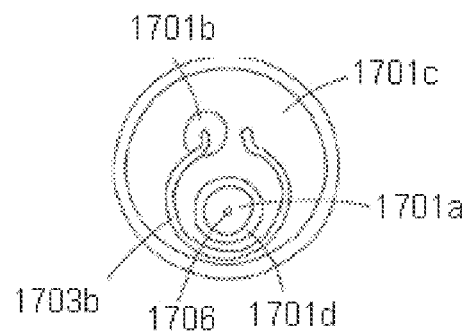
Figure 17B:
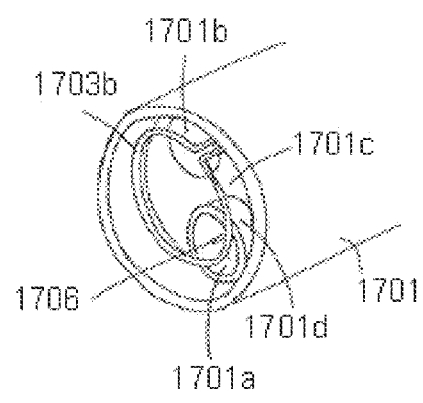
Figure 17D:
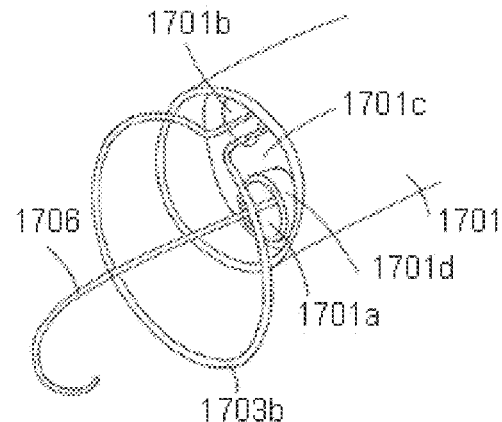

In some embodiments, the tissue cutter includes a flexible conductive loop that expands to adopt a horseshoe conformation upon deployment. As illustrated in FIGS. 17A-17D, the delivery catheter 1701 features two off-center lumens 1701*a* and 1701*b* and a recessed area 1701*c* at its distal end. In some embodiments, the guidewire 1706 resides within the first lumen 1701*a*. In some embodiments, the second lumen 1701*b* houses one end of the metal loop 1703*b* in its collapsed state and permits forward translation of the metal loop for full expansion (FIG. 17D). In some embodiments, the other side of the metal loop is fixed in the recessed area of the delivery catheter 1701. In some embodiments, the fully expanded metal loop is maintained coaxial to the guidewire. In some embodiments, the metal loop wraps around the extruded tube 1701*d* of the second lumen in its unexpanded state so that the guidewire resides internal to the circumference of the metal loop. The tissue retention element is deployed by running a separate tissue retention element catheter over the guidewire, through lumen 1701*a*, into the left atrium.

In some embodiments, the tissue cutter includes a stainless steel, cobalt chromium, or other type of plastically deformable conductive material in the form of a ring or stent-like structure that increases in diameter through balloon expansion.

Additional Device Features

In some embodiments, the device assemblies herein include the incorporation of oscillation/vibration, or actuation using a motor or piezoelectric circuit. In some embodiments, similarly, rotation is incorporated to minimize or prevent tissue adhesion as the tissue cutter is energized and cuts tissue.

In some embodiments, the guidewire acts as the anode, which eliminates the necessity of having an additional catheter that comprises an electrode shaped ring.

In some embodiments, the expandable tissue stabilizer features an array of individual ferromagnetic strips radially distributed to form an array (facing the septum). In some embodiments, the tissue cutter catheter has a disc magnet positioned in between the tissue cutter and the interatrial septum, which is undersized to the inner diameter of the delivery catheter, coaxially arranged around the tissue cutter catheter its distal tip. In some embodiments, the disc magnet is coaxially arranged around a separate catheter that is slidably engaged within the tissue cutter catheter and that has an inner lumen, the tissue stabilizer catheter is coaxial and slidable within this separate catheter. Upon deployment of the tissue stabilizer across the septum into the left atrium, in some embodiments, the disc magnet is advanced forward to make contact with the septum such that the septum becomes locked between the magnetic disc and the ferromagnetic array (thereby securing and stabilizing the septum). RF energy is applied to the tissue cutter to cut an aperture and the excised tissue is packed within the delivery catheter while being locked in between the magnetic disc and the tissue stabilizer. In some embodiments, the tissue cutter and magnetic disc are deployed in the left atrium, whereas the tissue stabilizer is deployed in the right atrium and both magnetic disc and the ferromagnetic array are facing the septum.

In some embodiments, suction is applied by a separate suctioning catheter and suction cup to the proximal side of the septum (within the right atrium) to stabilize the tissue during tissue cutting and excision. In some embodiments, the suctioning catheter is slidably engaged within the tissue cutter catheter and has a central lumen through which the tissue stabilizer catheter passes. In some embodiments, suction is applied so that the cup and septum coapt. Post-tissue cutting, in some embodiments, applied suction draws the excised tissue within the tissue cutter catheter, thereby ensuring tissue capture and retention. In some embodiments, a tissue stabilizer is used on the distal side of the septum (within the left atrium) to stabilize the tissue when suction is being applied, and during tissue cutting and excision. In some embodiments, the cup includes materials such as rubber, silicone, or other polymers.

In some embodiments, various catheters disclosed herein include one or more materials of polymer, metal, or metal/polymeric braided/coiled reinforcement to permit pushability for device insertion/introduction into the body.

In some embodiments, various catheters disclosed herein have a porthole to permit rapid wire exchange during device insertion/introduction into the body. In some embodiments, the delivery catheter contains one or more radiopaque markers to facilitate navigation and delivery to the heart (right atrium, left atrium, interatrial septum). In some embodiments, the distal tip of the delivery catheter is reinforced with a rigid or shape memory material to facilitate unsheathing/resheathing of the tissue cutter. In some embodiments, the delivery catheter ranges from 5-24Fr. In some embodiments, a temperature sensor is included at the distal end of the tissue cutter catheter to monitor the temperature of the area where tissue cutting is taking place to ensure that temperatures stay within a predetermined range. In some embodiments, an audio or visual feedback/warning system is incorporated into a catheter handle to notify users/operators of deviations from the predetermined range.

In some embodiments, an impedance sensor is included to monitor impedance between the RF cathode and anode to confirm completion of tissue excision, or to provide direct feedback to the RF generator for modulation of voltage based on a measured increase in tissue impedance. In some embodiments, the impedance sensor is includes one or more components of the device assemblies disclosed herein.

In some embodiments, the tissue stabilizer is used to direct ultrasound energy radially outwards and then axially towards the septum to permit ultrasound-mediated cutting of the septum. In some embodiments, the tissue stabilizer is used to align reflective strips and direct laser energy radially outwards and then axially towards the septum to permit laser-mediated cutting of the septum.

In some embodiments, the tissue cutter catheter features an internal circuit between the RF generator and the tissue cutter that limits the amount of current transmitted to the tissue cutter to a predetermined threshold; in some embodiments, an audio or visual feedback/warning system is incorporated into a catheter handle to notify users of excess input energy usage. In some embodiments, the internal circuit on the tissue cutter catheter or other components of the assembly prevents current transmission if the input energy is below a desired threshold; an audio or visual feedback/warning system is incorporated into a catheter handle, or the RF generator, to warn users of insufficient input energy usage.

In some embodiments, the tissue cutter catheter features a saline irrigation channel to flush saline throughout the catheter; saline or other solution is circulated through the distal tip and out the proximal end or, alternatively, through the distal end. In some embodiments, the saline irrigation system is a stand-alone unit, manually operated with a syringe, or integrated into the RF generator.

In some embodiments, one or more electrodes or conductive elements disclosed herein are coated with Polytetrafluoroethylene (PTFE) to minimize char buildup.

Plasma-Based Methods

In some embodiments, the tissue cutter is insulated with the exception of a 1-100 µm edge that transmits 15-200 µJ of current at 0.5 k-4.0 kV at 1-60 Hz pulses from the RF generator to ionize the tissue surrounding the conductive edge of the tissue cutter to produce a thin layer of plasma for tissue excision.

Enablement/Data Summary

Embodiments of the invention disclosed herein were fabricated and tested in a series of benchtop tests, acute animal studies with same-day sacrifice, and chronic animal studies through which pigs were allowed to survive for up to 5 months to assess durability of the interatrial aperture created using the device. One such embodiment was used to create an approximately 8 mm-diameter interatrial aperture in two live male Yorkshire cross pigs. The procedures were successfully performed under fluoroscopic and intracardiac echo guidance. No complications were encountered. 30-day follow up with fluoroscopy and intracardiac echo confirmed ongoing patency of the interatrial apertures with no evidence of regrowth.

For these tests, the electrode comprised a single-part nitinol stent with a circular cutting portion having an expanded outer diameter of 8 mm, width of 0.0635 mm, and 4 struts. The electrode was coated with a 11 µm-thick film of parylene C on all surfaces excluding the cutting portion. The electrode was coupled to a 32 AWG copper wire and attached to a 5Fr stainless steel reinforced polyimide catheter. The electrode resided in a collapsed state within an 8Fr distal dilator shaft prior to deployment. The tissue stabilizer comprised a single-part nitinol stent with a stabilizing portion having an expanded diameter of 11 mm, 4 struts, and an attachment portion that was attached to a 6Fr catheter. The tissue stabilizer was housed in a collapsed state within a steerable delivery catheter having an 8.5-9.0Fr inner diameter and 12Fr outer diameter. The device was inserted through a 14Fr vascular access sheath in the femoral vein over a 0.024" transseptal guidewire. An ERBE 250D RF generator unit was used to deliver 150W of monopolar RF energy in a 1-second pulse. A grounding pad was placed on the pigs' backside.

While preferred embodiments disclosed herein have been shown and described herein, it will be obvious to those skilled in the art that such embodiments are provided by way of example only. Numerous variations, changes, and substitutions will now occur to those skilled in the art without departing from the disclosure herein. It should be understood that various alternatives to the embodiments of the device assemblies described herein may be employed in practicing the device assemblies herein. It is intended that the following claims define the scope of the device assemblies herein and that methods and structures within the scope of these claims and their equivalents be covered thereby.

What is claimed is:

1. A device, comprising:
a first catheter defining a first lumen, the first catheter comprising a distalmost circumferential edge comprising a first electrode, a second electrode, and a non-conductive portion separating the first electrode and the second electrode, wherein one or more of the first electrode and the second electrode are exposed within a recess of the distalmost edge; and
a second catheter slidable within the first lumen, the second catheter comprising a tissue stabilizer configured to pull tissue into the first lumen.

2. The device of claim 1, wherein the distalmost edge is blunt.

3. The device of claim 1, wherein one or more of the first electrode and the second electrode comprise a semi-circular shape.

4. The device of claim 1, wherein the first catheter is configured to engage a right atrial side of an interatrial septum.

5. The device of claim 1, wherein the non-conductive portion of the distalmost edge comprises a first non-conductive portion opposing a second non-conductive portion.

6. The device of claim 1, wherein the first electrode and the second electrode are configured to cut an interatrial septum to create an interatrial pressure relief opening.

7. The device of claim 6, wherein the interatrial pressure relief opening comprises a size configured to slow a natural healing process of the tissue.

8. The device of claim 1, wherein the first catheter comprises an open-ended cylindrical shape.

9. The device of claim 1, wherein a diameter of the tissue stabilizer is less than a diameter of the first catheter to permit tenting of an interatrial septum such that an aperture created by the device is larger than the diameter of the first catheter.

10. The device of claim 1, wherein the tissue stabilizer is configured to expand.

11. The device of claim 1, wherein the tissue stabilizer is configured to expand after passing through an interatrial septum.

12. The device of claim 11, wherein the tissue stabilizer is configured to collapse when withdrawn into the first lumen to capture an excised tissue.

13. The device of claim 1, wherein the first catheter comprises a first diameter and the tissue stabilizer comprises an expanded diameter less than the first diameter.

14. The device of claim 1, further comprising a radio frequency (RF) generator coupled to the first electrode and the second electrode.

15. The device of claim 14, wherein the RF generator is configured to generate an RF signal comprising a frequency between about 300 kHz and about 3 MHz and a power between about 1 W and about 500 W.

16. A device, comprising:
a first catheter defining a first lumen, the first catheter comprising a distalmost edge comprising a first electrode exposed within a recess of the distalmost edge; and
a second catheter slidable within the first lumen, the second catheter comprising a tissue stabilizer comprising a second electrode, the tissue stabilizer configured to pull tissue into the first lumen.

17. The device of claim 16, wherein the first distal edge and the tissue stabilizer are blunt.

18. The device of claim 16, wherein the second catheter comprises a dilator configured to facilitate passage through an interatrial septum.

19. The device of claim 16, wherein the tissue stabilizer comprises one or more of a tine, a wire, and a strut.

20. The device of claim 16, wherein the tissue stabilizer is configured to extend distal to the first catheter when deployed within a left atrium.

21. The device of claim 16, wherein the tissue stabilizer is configured to capture an excised tissue within the first lumen.

* * * * *